(12) United States Patent
Schambony et al.

(10) Patent No.: US 7,714,044 B2
(45) Date of Patent: May 11, 2010

(54) USE OF 4-CYANO-NAPHTHALENE-1, 8-DICARBOXIMIDE DERIVATIVES AND RELATED COMPOUNDS TO PROTECT ORGANIC MATERIAL FROM THE DAMAGING EFFECTS OF LIGHT

(75) Inventors: Simon Schambony, Ludwigshafen (DE); Alban Glaser, Mannheim (DE); Ruediger Sens, Ludwigshafen (DE); Arno Boehm, Mannheim (DE); Helmut Reichelt, Neustadt (DE)

(73) Assignee: BASF Akitengesellschaft, Ludwigshafen (DE)

( * ) Notice: Subject to any disclaimer, the term of this patent is extended or adjusted under 35 U.S.C. 154(b) by 0 days.

(21) Appl. No.: 10/579,441

(22) PCT Filed: Nov. 12, 2004

(86) PCT No.: PCT/EP2004/012873
§ 371 (c)(1),
(2), (4) Date: May 15, 2006

(87) PCT Pub. No.: WO2005/047265
PCT Pub. Date: May 26, 2005

(65) Prior Publication Data
US 2007/0100033 A1     May 3, 2007

Related U.S. Application Data

(63) Continuation-in-part of application No. 10/770,603, filed on Feb. 4, 2004.

(30) Foreign Application Priority Data
Nov. 14, 2003  (DE)  ................ 103 53 328

(51) Int. Cl.
*C08K 5/34*    (2006.01)
(52) U.S. Cl. ............... 524/89; 546/79; 546/98
(58) Field of Classification Search ........... 524/100, 524/89; 546/79, 98
See application file for complete search history.

(56) References Cited

U.S. PATENT DOCUMENTS
2007/0117887 A1*   5/2007   Naik et al. .......... 524/89

FOREIGN PATENT DOCUMENTS

| EP | 0 263 705 | | 4/1988 |
|---|---|---|---|
| EP | 0 335 595 | | 10/1989 |
| EP | 0 682 145 | | 11/1995 |
| FR | 1344883 | * | 10/1963 |
| GB | 1 003 083 | | 9/1965 |
| JP | 39-009280 | | 6/1964 |
| JP | 39-011770 | | 6/1964 |
| JP | 49-057048 | | 6/1974 |
| JP | 01 024852 | | 1/1989 |
| JP | 3-020353 | | 1/1991 |
| JP | 7247978 | | 9/1995 |
| JP | 7-310095 | | 11/1995 |
| JP | 9-318983 | | 12/1997 |

OTHER PUBLICATIONS

Jedlinski, Z.J. et al., "New Poly bis (benzimidazobenzisoquinolinones)", Macromolecules, vol. 16, No. 4, pp. 522-526, 1983.

Yamazaki et al., "Syntheses of polymers using 1, 4, 5-naphthalenetricarboxylic anhydride. V. Synthesis of polyamide-imides from 1, 4, 5-naphthalenetricarboxylic anhydride. 3.", Nippon Kagaku Kaishi, vol. 12, pp. 2401-2405, 1973.

"1H-Benz[de]isoquinoline-6-carboxamide, 2, 3-dihydro-2-(4-methoxyphenyl)-N, N-dimethyl-3, 3-dioxo-", Interbioscreen Compound Library, XP002320325, 2003.

1H-Benz[de]isoquinoline-6-carboxamide, 2, 3-dihydro-N-methyl-3, 3-dioxo-N-(phenylmethyl)-2-[3-(trifluoromethyl) phenyl]-(9CI) (CA Index Name), XP002320326, 2001.

1H-Benz[de] isoquinoline-6-carboxamide, 2,3-dihydro-N-methyl-1,3-dioxo-N-(phenylmethyl)-2-3[3-(trifluoromethyl) phenyl] Enamine Screeing Library, 2002:269530, 2004.

* cited by examiner

*Primary Examiner*—Peter D Mulcahy
(74) *Attorney, Agent, or Firm*—Oblon, Spivak, McClelland, Maier & Neustadt, L.L.P.

(57) ABSTRACT

A description is given of the use of naphthalene-1,8-dicarboxylic monoimides of the formula (I), in which $R^1$ is hydrogen, alkyl, alkenyl, cycloalkyl, cycloalkenyl, heterocycloalkyl, aryl or heteroaryl and $R^2$ is a radical containing at least one π electron system containing a carbon atom and at least one further atom selected from carbon, oxygen, and nitrogen, with the proviso that the radical contains at least one atom other than carbon; to protect organic material from the damaging effects of light, of compositions which comprise at least one naphthalene-1,8-dicarboxylic monoimide of the formula (I) in an amount which provides protection from the damaging effects of light, and at least one organic material, and of new naphthalene-1,8-dicarboxylic monoimides (I).

28 Claims, 1 Drawing Sheet

USE OF 4-CYANO-NAPHTHALENE-1, 8-DICARBOXIMIDE DERIVATIVES AND RELATED COMPOUNDS TO PROTECT ORGANIC MATERIAL FROM THE DAMAGING EFFECTS OF LIGHT

The present invention relates to the use of naphthalene-1,8-dicarboxylic monoimides for protecting organic material against the damaging effects of light, to compositions which comprise at least one organic material and at least one naphthalene-1,8-dicarboxylic monoimide of the formula I in an amount providing protection from the damaging effects of light, and to new naphthalene-1,8-dicarboxylic monoimides.

Living and inanimate organic material such as human or animal skin, human or animal hair, paper, foods, perfumes, cosmetics, plastics, polymer dispersions, paints, photographic emulsions, photographic layers, etc., is frequently sensitive to the damaging effects of light, and particularly to the ultraviolet (UV) radiation fraction which is present in daylight. The damage may be due to the UVA fraction of the UV radiation, i.e., the region from above 320 to 400 nm, the UVB fraction of UV radiation, i.e. the region from 280 to 320 nm, and the even shorter-wave fractions of UV radiation. There is therefore a substantial and ongoing demand for new substances which provide effective protection against such damaging effects. In this application the substances employed are increasingly having to meet a complex profile of requirements tailored to the specific nature of the organic material to be protected, the circumstances under which protection is required, and the desired protective effect.

It is known that the mechanical, chemical and/or esthetic properties of organic material, particularly of plastics, may be impaired under the effect of light. This impairment is normally manifested as yellowing, discoloration, cracking or embrittlement in the material. One important field of use for light stabilizers is therefore the protection of plastics. Plastic containers and plastic films find widespread use as packaging materials, for example. For reasons of esthetics, plastics featuring high light transmission in the visible wavelength range from 400 to 750 nm are increasingly gaining importance as packaging materials. See-through plastics with or without slight coloration, however, are generally transparent to the UV fractions of daylight, with the consequence that, under light, both the packaging material and the packaged products suffer aging. Depending on the specific packaged contents, the adverse alteration to the contents may be manifested, for example, in a change in appearance, such as yellowing and discoloration, in a change in taste and/or odor, and/or in the breakdown of ingredients. In the case of foods, perfumes, and cosmetics, the shelf life and keeping properties may be sharply reduced. The stabilizers that are added to packaging plastic ought therefore to provide satisfactory protection both to the plastic itself and to the packaged product in respect of light-induced aging processes. Plastics are also in widespread use in combination with glass in composite materials which are transparent in the visible wavelength range. Composite systems of this kind find use in automotive and architectural glazing, for example. Automobile windows of this kind are increasingly being required to absorb radiation in the wavelength range below 400 nm, in order to protect the interior of the auto and its occupants against UV radiation, for example.

GB 1,003,083 describes 4-alkoxynaphthalene-1,8-dicarboxylic monoimides and their use as optical brighteners for textiles. The textiles may consist of natural or synthetic fibers, including polyamides, polyesters, polyurethanes, polyvinyl chloride, polyvinylidene chloride, polyacrylonitrile or polyvinyl alcohols.

EP 0682145 describes a method of improving the sun protection factor in textiles, wherein the textile fiber is treated with a composition comprising at least one optical brightener which absorbs in the wavelength range of 280-400 nm. Alongside a host of further compounds, suitable optical brighteners specified include (by way of a formula), naphthalene-1,8-dicarboxylic monoimides that carry in position(s) 4 and/or 5 a $C_1$-$C_4$ alkoxy, $SO_3M$ (where definitions of M include H, Na, K, Ca, Mg, ammonium or mono-, di-, tri- or tetra-$C_1$-$C_4$-alkylammonium) or NHCO—$C_1$-$C_4$ alkyl group. The only specific 4-substituted compound disclosed is the 4-methoxy compound. There are no working examples for this class of compound.

EP 0263705 describes the use of naphthalenetetracarboxylic acid or its derivatives as light stabilizers in thermoplastic polyester resin compositions, in which additional components that can be used include naphthalene monoimides. The imide group of the monoimides can be in the 1,8, 2,3 or 3,4 positions of the naphthalene ring. Additionally the naphthalene ring either is unsubstituted or can carry up to 6 further substituents, selected from halo, hydroxyl, amino, nitro, cyano, sulfonic acid or metal salts thereof, optionally substituted alkyl, optionally substituted alkenyl, optionally substituted aralkyl, and optionally substituted alkylaralkyl. Preferably the naphthalene ring of the naphthalene monoimides does not carry any further substituents.

EP 0335595 describes thermoplastic polyester compositions comprising as UV absorbers a diimide compound plus, if desired, a naphthalene monoimide. The imide group of the monoimide can be located in the 1,2, 1,8 or 2,3 positions of the naphthalene ring. The naphthalene ring may carry up to 6 further substituents, selected from halo, carboxyl or an ester thereof, hydroxyl, —O—C(=O)CH$_3$, amino, nitro, cyano, sulfonic acid or a metal salt thereof, optionally substituted alkoxy, optionally substituted aliphatic groups, and optionally substituted aromatic groups.

JP1024852 describes the use of substituted or unsubstituted naphthalenedicarboxylic and -tetracarboxylic acids or their esters, imides, and anhydrides as light stabilizers for polyamide resins. The polyamide resins can be used as packaging material for foods.

JP-7247978 describes brightener compositions for synthetic fibers, comprising a mixture of 4-substituted naphthalene-1,8-dicarboxylic monoimides and, if desired, alkyl-naphthalenesulfonates. The mixture comprises naphthalenecarboxylic monoimides in which the substituent in position 4 is a lower alkoxy or unsubstituted phenoxy or benzyloxy group and compounds in which the substituent in position 4 is an alkylthio, phenylthio or benzylthio group. The imide nitrogen atom can in each case be substituted by a hydrogen atom or by an alkyl or hydroxyl group. A significant disadvantage of the lower-alkoxy-substituted and/or unsubstituted-phenoxy-substituted naphthalene-1,8-dicarboxylic monoimides described is their low compatibility with plastics.

The prior art light stabilizers have a series of disadvantages. One substantial disadvantage is the period of the protective effect, which is often too short, since the known light stabilizers often have an inadequate UV stability. Another disadvantage is that many known light stabilizers have a clearly perceptible intrinsic color in the visible wavelength range, with the consequence that a plastic stabilized with these light stabilizers appears to have a pale yellow coloration. Furthermore, many light stabilizers are unable to filter out the longwave fraction of the UVA radiation. Many light stabilizers exhibit low solubility in the application medium. The resulting crystallization of the light stabilizer may make the polymer opaque. Further disadvantages are the frequently poor synthetic obtainability of the light stabilizers, their inadequate formulating properties, their low sublimation resistance and/or their low migration fastness. There is therefore still a need for stabilizers and stabilizer compositions which have improved performance properties and/or are easier to prepare.

It is an object of the present invention, therefore, to provide stabilizers which are suitable as UV absorbers for protecting organic material such as plastics, polymer dispersions, paints, photographic emulsions, photographic layers, paper, human or animal skin, human or animal hair, foods, etc. for a relatively long period of time. The stabilizers should preferably absorb with high extinction in the UVA region, and particularly also in the longwave UVA region above 360 nm, ought to be photostable and/or thermally stable, and ought to have little or no intrinsic color in the visible wavelength range.

Figure 1:
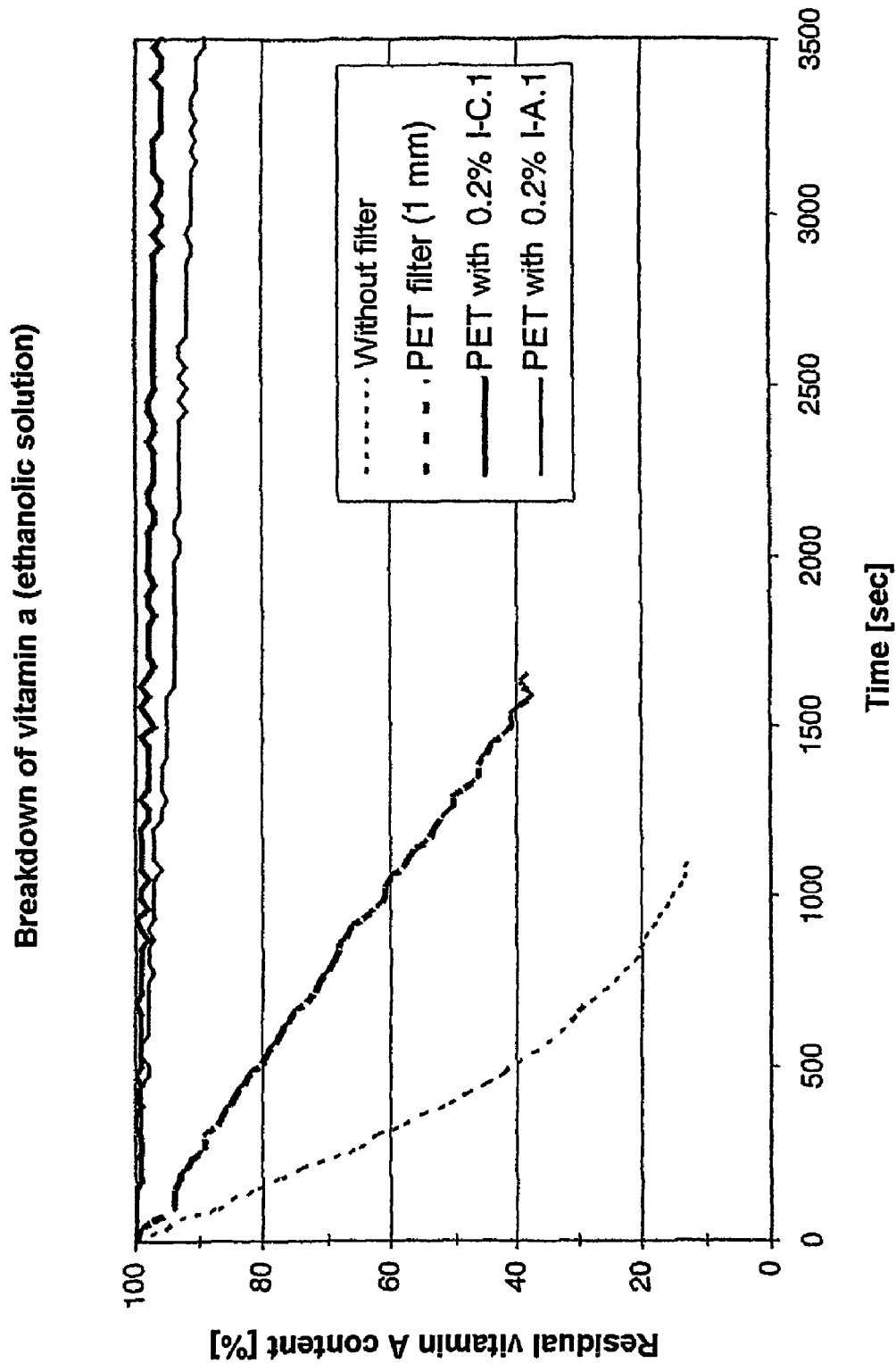
FIG. 1 shows the filter effect of the compounds I used in accordance with the invention, as a graph. Since the emissions spectrum of a xenon lamp is similar to that of the sun, FIG. 1 forcefully demonstrates the filter effect of the naphthalene-1,8-dicarboxylic monoimides I used in accordance with the invention. Without the protection of naphthalene-1, 8-dicarboxylic monoimides I a vitamin A solution is rapidly broken down by light. In contrast, there is only slight breakdown of the vitamin A solution under the effect of light if the vitamin A solution is protected by a naphthalene-1,8-dicarboxylic monoimide I used in accordance with the invention.

Surprisingly it has now been found that the use of naphthalene-1,8-dicarboxylic monoimides of the formula I

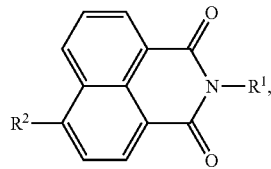

(I)

in which
$R^1$ is hydrogen, alkyl, alkenyl, cycloalkyl, cycloalkenyl, heterocycloalkyl, aryl or heteroaryl and
$R^2$ is a radical containing at least one π electron system containing a carbon atom and at least one further atom selected from carbon, oxygen, and nitrogen, with the proviso that the radical contains at least one atom other than carbon
protects organic material against the damaging effects of light.

The present invention accordingly provides for the use of naphthalene-1,8-dicarboxylic monoimides of the formula I for protecting organic material against the damaging effects of light.

The present invention further provides composition comprising at least one organic material and at least one naphthalene-1,8-dicarboxylic monoimide of the formula I in an amount providing protection against the damaging effects of light.

The present invention additionally provides a method of protecting organic material against the damaging effects of light, which involves adding to said material at least one naphthalene-1,8-dicarboxylic monoimide of the formula I.

The present invention also provides compounds of the formula I

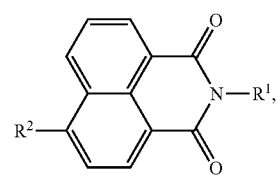

(I)

where
$R^1$ is hydrogen, alkenyl, cycloalkyl, cycloalkenyl, heterocycloalkyl, aryl or heteroaryl, preferably $C_5$-$C_8$ cycloalkyl or phenyl, the two last-mentioned radicals each being unsubstituted or carrying one, two, three, four or five $C_1$-$C_4$ alkyl groups, and
$R^2$ is cyano, —C(O)NR$^5$R$^{5a}$ or phenyloxy which carries one, two, three, four or five $C_1$-$C_{12}$ alkyl groups; and
$R^5$ and $R^{5a}$ are each independently of one another hydrogen, $C_1$-$C_{18}$ alkyl, aryl or heteroaryl, aryl and heteroaryl each being unsubstituted or carrying one or more substituents selected preferably from $C_1$-$C_6$ alkyl, $C_1$-$C_6$ alkoxy, hydroxyl, carboxyl, and cyano.

The term "protection" is to be interpreted widely in the context of the present invention. It embraces on the one hand the stabilization of an organic material with respect to the damaging effects of light in order to prevent and/or retard light-initiated degradation processes in the organic material. For this purpose an agent which protects against light is added to the organic material. On the other hand the aforementioned term, in the context of the present invention, further embraces the indirect protection of materials, where a material containing an agent that protects against light surrounds at least partly another organic material which is not protected against the effects of light, so as to reduce the damaging effects of light for the organic material behind which is not protected against light.

For the purpose of elucidating the present invention the expression "alkyl" embraces straight-chain and branched alkyl. Alkyl is preferably straight-chain or branched $C_1$-$C_{30}$ alkyl, particularly $C_1$-$C_{20}$ alkyl, and especially $C_1$-$C_{12}$ alkyl. Examples of alkyl groups are, in particular, methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, 1,1,3,3-tetramethylbutyl, nonyl, decyl, n-undecyl, n-dodecyl, n-tridecyl, iso-tridecyl, n-tetradecyl, n-hexadecyl, n-octadecyl and n-eicosyl.

Alkyl also embraces an alkyl whose carbon chain can be interrupted by one or more nonadjacent groups selected from —O—, —S—, —NR$^3$—, —CO— and/or —SO$_2$—; i.e., the termini of the alkyl group are formed by carbon atoms.

The above remarks apply equally to alkoxy and to alkylamino.

Alkenyl refers in the sense of the present invention to straight-chain and branched alkenyl groups, which depending on chain length may carry one or more double bonds. They are preferably $C_2$-$C_{20}$, more preferably $C_2$-$C_{10}$, alkenyl groups, such as vinyl, allyl or methallyl. "Alkenyl" also embraces substituted alkenyl groups, which can carry, for example, 1, 2, 3, 4 or 5 substituents. Examples of suitable substituents include cycloalkyl, heterocycloalkyl, aryl, heteroaryl, nitro, cyano, halo, amino, and mono- and di($C_1$-$C_{20}$ alkyl)amino.

Cycloalkyl for the purposes of the present invention embraces both substituted and unsubstituted cycloalkyl groups, preferably $C_3$-$C_8$ cycloalkyl groups such as cyclopropyl, cyclobutyl, cyclopentyl, cyclohexyl, cycloheptyl or cyclooctyl, and especially $C_5$-$C_8$ cycloalkyl. When substituted the cycloalkyl groups may carry one or more—for example, one, two, three, four or five—$C_1$-$C_6$-alkyl groups.

$C_5$-$C_8$ cycloalkyl, which is unsubstituted or may carry one or more $C_1$-$C_6$-alkyl groups, is, for example, cyclopentyl, 2- and 3-methylcyclopentyl, 2- and 3-ethylcyclopentyl, cyclohexyl, 2-, 3-, and 4-methylcyclohexyl, 2-, 3-, and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3-, and 4-methylcycloheptyl, 2-, 3-, and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4-, and 5-methylcyclooctyl, 2-, 3-, 4- and 5-ethylcyclooctyl, and 3-, 4-, and 5-propylcyclooctyl.

Aryl for the purposes of the present invention embraces monocyclic or polycyclic aromatic hydrocarbon radicals which may be unsubstituted or substituted. Aryl is preferably phenyl, tolyl, xylyl, mesityl, duryl, naphthyl, fluorenyl, anthracenyl, phenanthrenyl or naphthyl, more preferably phenyl or naphthyl, it being possible for these aryl groups when substituted to carry generally 1, 2, 3, 4 or 5, preferably 1, 2 or 3, substituents selected from $C_1$-$C_{18}$ alkyl, $C_1$-$C_6$ alkoxy, cyano, $CONR^4R^{4a}$, $CO_2R^4$, arylazo, and heteroarylazo, with arylazo and heteroarylazo themselves being unsubstituted or carrying one or more radicals selected independently of one another from $C_1$-$C_{18}$ alkyl, $C_1$-$C_6$ alkoxy, and cyano.

Aryl, unsubstituted or carrying one or more radicals selected independently of one another from $C_1$-$C_{18}$ alkyl, $C_1$-$C_6$ alkoxy, and cyano, is, for example, 2-, 3-, and 4-methylphenyl, 2,4-, 2,5-, 3,5-, and 2,6-dimethylphenyl, 2,4,6-trimethylphenyl, 2-, 3-, and 4-ethylphenyl, 2,4-, 2,5-, 3,5-, and 2,6-diethylphenyl, 2,4,6-triethylphenyl, 2-, 3-, and 4-propylphenyl, 2,4-, 2,5-, 3,5-, and 2,6-dipropylphenyl, 2,4,6-tripropylphenyl, 2-, 3-, and 4-isopropylphenyl, 2,4-, 2,5-, 3,5-, and 2,6-diisopropylphenyl, 2,4,6-triisopropylphenyl, 2-, 3-, and 4-butylphenyl, 2,4-, 2,5-, 3,5-, and 2,6-dibutylphenyl, 2,4,6-tributylphenyl, 2-, 3-, and 4-isobutylphenyl, 2,4-, 2,5-, 3,5-, and 2,6-diisobutylphenyl, 2,4,6-triisobutylphenyl, 2-, 3-, and 4-sec-butylphenyl, 2,4-, 2,5-, 3,5-, and 2,6-di-sec-butylphenyl, 2,4,6-tri-sec-butylphenyl, 2-, 3-, and 4-tert-butylphenyl, 2,4-, 2,5-, 3,5-, and 2,6-di-tert-butylphenyl and 2,4,6-tri-tert-butylphenyl; 2-, 3-, and 4-methoxyphenyl, 2,4-, 2,5-, 3,5-, and 2,6-dimethoxyphenyl, 2,4,6-trimethoxyphenyl, 2-, 3-, and 4-ethoxyphenyl, 2,4-, 2,5-, 3,5-, and 2,6-diethoxyphenyl, 2,4,6-triethoxyphenyl, 2-, 3-, and 4-propoxyphenyl, 2,4-, 2,5-, 3,5-, and 2,6-dipropoxyphenyl, 2-, 3-, and 4-isopropoxyphenyl, 2,4-, 2,5-, 3,5-, and 2,6-diisopropoxyphenyl, 2-, 3-, and 4-butoxyphenyl; and 2-, 3-, and 4-cyanophenyl.

Heterocycloalkyl for the purposes of the present invention embraces nonaromatic, unsaturated or fully saturated, cycloaliphatic groups having generally 5 to 8 ring atoms, preferably 5 or 6 ring atoms, in which 1, 2 or 3 of the ring carbon atoms are replaced by heteroatoms selected from oxygen, nitrogen, sulfur, and a group —$NR^3$—, and being unsubstituted or substituted by one or more—for example, 1, 2, 3, 4, 5 or 6-$C_1$-$C_6$ alkyl groups. Examples that may be given of such heterocycloaliphatic groups include pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 1,2-oxazolin-5-yl, 1,3-oxazolin-2-yl, and dioxanyl.

Heteroaryl for the purposes of the present invention embraces substituted or unsubstituted, heteroaromatic, monocyclic or polycyclic groups, preferably the groups pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl, and carbazolyl, which when substituted can carry generally 1, 2 or 3 substituents. The substituents are selected from $C_1$-$C_6$ alkyl, $C_1$-$C_6$ alkoxy, hydroxyl, carboxyl, and cyano.

5- to 7-membered heterocycloalkyl or heteroaryl radicals bonded by a nitrogen atom and optionally containing further heteroatoms are, for example, pyrrolyl, pyrazolyl, imidazolyl, triazolyl, pyrrolidinyl, pyrazolinyl, pyrazolidinyl, imidazolinyl, imidazolidinyl, pyridinyl, pyridazinyl, pyrimidinyl, pyrazinyl, triazinyl, piperidinyl, piperazinyl, oxazolyl, isooxazolyl, thiazolyl, isothiazolyl, indolyl, quinolinyl, isoquinolinyl or quinaldinyl.

In accordance with the invention the radical $R^2$ includes at least one π electron system having a carbon atom and at least one further atom selected from carbon, oxygen, and nitrogen. It is understood in the context of the present invention to embrace π electron systems both with localized and with delocalized π bonds. The π electron systems with delocalized π bonds include aromatic compounds, heteroaromatic compounds, and polyenes. A π electron system is generally possible only in the case of polyatomic groups.

Examples of π electron systems made up of carbon atoms are groups having one or more C=C double bonds such as in alkenyl, cycloalkenyl or aryl, and groups having at least one C≡C triple bond such as in alkynyl or cycloalkynyl. Examples of groups with a π electron system having at least one carbon atom and at least one further atom selected from oxygen and nitrogen are aryloxy, corresponding heteroaryls, and the carbonyl group, for example, the keto group or aldehyde group, the carboxyl group, and also the carboxylate group, the ester group, the amide group, and the anhydride group, groups having a C=N double bond such as in imines, and groups having a C≡N triple bond as in nitrites. It will be appreciated that $R^2$ may contain two or more π electron systems selected independently of one another from the aforementioned groups.

Preferably $R^2$ contains only one π electron system. The π electron system is preferably in conjugation with the naphthalene skeleton.

The expression "in which $R^2$ is a radical which contains at least one π electron system having a carbon atom and at least one further atom selected from carbon, oxygen, and nitrogen, with the proviso that the radical contains at least one atom other than carbon" is understood in the context of the present invention to mean that $R^2$ has at least one non-carbon atom, i.e., at least one heteroatom—one or two heteroatoms, for example. The heteroatom may be an oxygen, nitrogen or sulfur atom, for example. The heteroatom may in principle be in any position within $R^2$. For example, the heteroatom may be part of the π electron system. The π electron system may also consist solely of carbon atoms, so that the heteroatom must be at a different position in $R^2$. $R^2$ may be bound to the naphthalene-1,8-dicarboxylic monoimide skeleton by way of a carbon atom or by way of a heteroatom, an oxygen atom for example.

One first preferred embodiment of the present invention relates to the use of at least one compound I in which
$R^1$ is $C_1$-$C_{30}$ alkyl whose carbon chain may be interrupted by one or more nonadjacent groups selected from —O—, —S—, —NR$^3$—, —CO— and/or —SO$_2$—, and/or which is unsubstituted or substituted one or more times by identical or different radicals selected from cyano, amino, hydroxyl, carboxyl, aryl, heterocycloalkyl, and heteroaryl, with aryl, heterocycloalkyl, and heteroaryl groups being unsubstituted or carrying one or more substituents selected independently of one another from $C_1$-$C_{18}$ alkyl and $C_1$-$C_6$ alkoxy; or
$R^1$ is $C_5$-$C_8$ cycloalkyl which is unsubstituted or carries one or more $C_1$-$C_6$ alkyl groups; or
$R^1$ is 5- to 8-membered heterocycloalkyl which is unsubstituted or carries one or more $C_1$-$C_6$ alkyl groups; or
$R^1$ is aryl or heteroaryl, with aryl or heteroaryl being unsubstituted or carrying one or more radicals selected independently of one another from $C_1$-$C_{18}$ alkyl, $C_1$-$C_6$ alkoxy, cyano, CONR$^4$R$^{4a}$, CO$_2$R$^4$, arylazo, and heteroarylazo, with arylazo and heteroarylazo in turn being unsubstituted or carrying one or more radicals selected independently of one another from $C_1$-$C_{18}$ alkyl, $C_1$-$C_6$ alkoxy, and cyano;
$R^3$ is hydrogen or $C_1$-$C_6$ alkyl; and
$R^4$ and $R^{4a}$ each independently are hydrogen, $C_1$-$C_{18}$ alkyl, aryl or heteroaryl, with aryl and heteroaryl in each case being unsubstituted or carrying one or more substituents selected from $C_1$-$C_6$ alkyl, $C_1$-$C_6$ alkoxy, hydroxyl, carboxyl and cyano.

Particular preference is given to compounds I wherein $R^1$ is $C_1$-$C_{12}$ alkyl, $C_5$-$C_8$ cycloalkyl or phenyl, the two last-mentioned radicals each being unsubstituted or carrying one, two, three, four or five $C_1$-$C_4$ alkyl groups. Especially preferred compounds I are those wherein $R^1$ is $C_1$-$C_{12}$ alkyl or $C_5$-$C_8$ cycloalkyl, especially cyclohexyl, which is unsubstituted or carries a $C_1$-$C_4$ alkyl group, or $R^1$ is phenyl which is unsubstituted or carries one, two or three $C_1$-$C_4$ alkyl groups. If phenyl carries two or three $C_1$-$C_4$ alkyl groups, then two of them are preferably attached in positions 2 and 6.

If $R^1$ is an alkyl radical having at least one heterocycloalkyl substituent or one heteroaryl substituent, the radical in question is preferably a 5- to 7-membered heterocycloalkyl which is attached to the alkyl radical via a nitrogen atom, or a 5- to 7-membered heteroaryl which is attached to the alkyl radical via a nitrogen atom.

$R^1$ is, for example, 2-ethylhexyl, cyclohexyl, 4-tert-butylcyclohexyl, phenyl, 2,6-diisopropylphenyl or 2,4,6-trimethylphenyl.

A characteristic feature of the compounds I is the radical $R^2$ with at least one π electron system and at least one heteroarom. The π electron system may contain one or more—for example, one or two—heteroatoms. In one preferred embodiment of the present invention the π electron system comprises at least one nitrogen and/or oxygen heteroatom. In that case the radical $R^2$ is preferably attached via a carbon atom of the π electron system to the naphthalene-1,8-dicarboxylic monoimide skeleton. The radical $R^2$ which characterizes the compound I is, in particular, cyano or —C(O)NR$^5$R$^{5a}$, where R$^5$ and R$^{5a}$ are as defined above. Preferably R$^5$ and R$^{5a}$ each independently of one another are hydrogen or $C_1$-$C_{18}$ alkyl, and in particular are each hydrogen.

Compounds I in which R$^2$ is cyano are referred to below sometimes as compounds I-A. Compounds I in which R$^2$ is —C(O)NR$^5$R$^{5a}$ where R$^5$ and R$^{5a}$ are as defined above are referred to below sometimes as compounds I-B.

In a further preferred embodiment of the present invention the π electron system is attached via a heteroatom to the naphthalene-1,8-dicarboxylic monoimide skeleton. A particularly suitable heteroatom is oxygen. In that case the radical $R^2$ is preferably phenoxy which carries one, two, three, four or five substituents. Substituents of the phenoxy radical are preferably selected from $C_1$-$C_{12}$ alkyl, $C_1$-$C_{12}$ alkoxy, —COOR$^6$, —SO$_3$R$^6$, halo, hydroxyl, carboxyl, cyano, —CONR$^5$R$^{5a}$, and —NHCOR$^5$, where R$^5$, R$^{5a}$, and R$^6$ are as defined above. Particularly preferred alkyl substituents are $C_1$-$C_{10}$ alkyl radicals, especially $C_3$-$C_{10}$ alkyl radicals. In particular the substituents on the phenyl ring are selected from substituents containing only carbon atoms, so that the radical R$^2$ contains only 1 heteroatom. In a further, especially preferred embodiment of the present invention the phenoxy group carries in position 4 a $C_1$-$C_{10}$ alkyl group, in particular $C_3$-$C_{10}$ alkyl group such as isopropyl, 1,1-dimethylpropyl (tert-pentyl) or 1,1,3,3-tetramethylbutyl(tert-octyl).

Compounds I in which R$^2$ is substituted phenoxy are referred below sometimes as compounds I-C.

Especially preferred among the naphthalene-1,8-dicarboxylic monoimides I are those in which R$^1$ and R$^2$ in combination have the definitions indicated below:
$R^1$ is $C_1$-$C_{12}$ alkyl, especially $C_1$-$C_{10}$ alkyl, $C_5$-$C_8$ cycloalkyl which is unsubstituted or carries a $C_1$-$C_4$ alkyl group, especially cyclohexyl which is unsubstituted or carries a $C_1$-$C_4$ alkyl group, or phenyl which is unsubstituted or carries one, two or three $C_1$-$C_4$ alkyl group(s), and
$R^2$ is cyano, —C(O)NH$_2$ or phenyloxy which carries a $C_1$-$C_{10}$ alkyl group, preferably a $C_3$-$C_{10}$ alkyl group.

Examples of suitable naphthalene-1,8-dicarboxylic monoimides I include 4-cyano-N-(cyclohexyl)naphthalene-1,8-dicarboximide, 4-cyano-N-(4-tert-butylcyclohexyl)-naphthalene-1,8-dicarboximide, 4-cyano-N-(2,6-diisopropylphenyl)naphthalene-1,8-dicarboximide, 4-cyano-N-(phenyl)-naphthalene-1,8-dicarboximide, 4-cyano-N-(2,4,6-trimethylphenyl)naphthalene-1,8-dicarboximide, 4-aminocarbonyl-N-(2,6-diisopropylphenyl)naphthalene-1,8-dicarboximide, N-(2,6-diisopropylphenyl)-4-(4-tert-octylphenoxy)naphthalene-1,8-dicarboximide, N-(2,6-diisopropylphenyl)-4-(4-isopropylphenoxy)naphthalene-1,8-dicarboximide, N-(2,6-diisopropylphenyl)-4-(4-tert-pentylphenoxy)naphthalene-1,8-dicarboximide, N-(phenyl)-4-(4-tert-octylphenoxy)-naphthalene-1,8-dicarboximide, N-(phenyl)-4-(4-isopropylphenoxy)-naphthalene-1,8-dicarboximide, N-(phenyl)-4-(4-tert-pentylphenoxy)naphthalene-1,8-dicarboximide, N-(2-ethylhexyl)-4-(4-tert-octylphenoxy)naphthalene-1,8-dicarboximide, N-(2-ethylhexyl)-4-(4-isopropylphenoxy)naphthalene-1,8-dicarboximide, N-(2-ethylhexyl)-4-(4-tert-pentylphenoxy)naphthalene-1,8-dicarboximide, and N-(2,4,6-trimethylphenyl)-4-(4-tert-octylphenoxy)naphthalene-1,8-dicarboximide.

The compounds of the formula I-A (I-A)

where
R¹ has the suitable and preferred definitions specified above can be prepared for example by reacting 4-halonaphthalene-1,8-dicarboximides II with copper(I) cyanide in accordance with scheme 1.

Scheme 1:

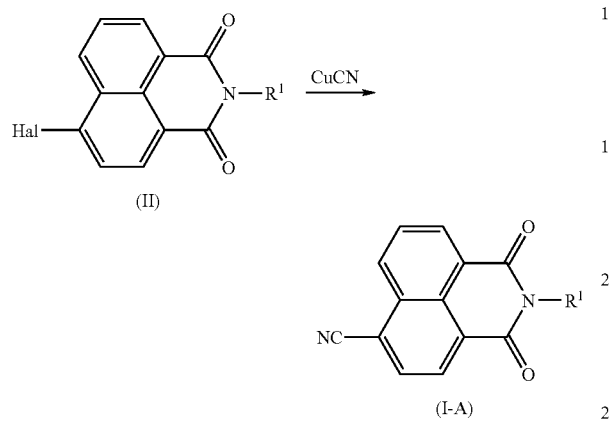

In scheme 1 Hal is halogen, such as fluorine, bromine, chlorine or iodine, particularly bromine or iodine. R¹ is as defined above. R¹ is preferably $C_1$-$C_{12}$ alkyl, $C_5$-$C_8$ cycloalkyl or phenyl, the two last-mentioned radicals each being unsubstituted or carrying one, two, three, four or five $C_1$-$C_4$ alkyl groups.

The reaction takes place normally in an organic solvent which contains nitrogen and is inert under the reaction conditions. Examples of suitable organic solvents which contain nitrogen include aromatic nitrogen heterocycles such as pyridine, 2-methylpyridine, 3-methylpyridine or 4-methylpyridine, quinoline or isoquinoline, N,N-dialkylcarboxamides such as N,N-dimethylformamide or N,N-dimethylacetamide, and N-alkyl lactams such as N-methylpyrrolidone.

The reaction takes place generally at a temperature between room temperature and the boiling temperature of the solvent, preferably at temperatures between 40° C. and the boiling temperature of the solvent, and in particular at the boiling temperature of the solvent.

The compound II and the copper(I) cyanide are normally employed in approximately equimolar amounts. It may also be of advantage, however, to use one of the two reactants in excess. In one preferred embodiment the copper(I) cyanide is used in excess, relative to the compound II.

It may also be of advantage to carry out the reaction in the presence of metal iodides, preferably transition metal iodides, and in particular copper(I) iodide.

The reaction mixture is worked up generally by diluting with water and the product is isolated by filtration. Where appropriate the product can be purified in a customary way, by crystallization or chromatography for example.

In order to remove the copper salts, particularly the copper (I) salts, from the product it may be advantageous to convert the salts into copper(II) salts by oxidation in aqueous solution, with hydrogen peroxide or iron(III) salts, for example, and then to isolate the product by extraction with an organic, water-immiscible solvent. Moreover, copper salts can be removed by treatment with aqueous solutions of complexing reagents, such as ammonia, organic monoamines or diamines, and soluble cyanide salts. An alternative option is to extract the product with organic solvents, e.g., chlorinated hydrocarbons such as dichloromethane or 1,2-dichloroethane or ketones such as acetone, with the aid, for example, of a Soxhlet apparatus, from the crude product.

The 4-halonaphthalene-1,8-dicarboximides II can be prepared for example by reacting 4-halonaphthalene-1,8-dicarboxylic anhydrides III with a primary amine IV in accordance with the reaction sequence depicted in scheme 2.

Scheme 2:

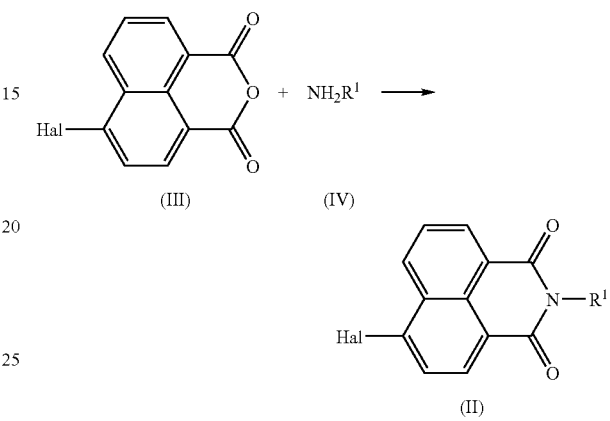

In scheme 2 Hal is halogen, such as fluorine, bromine, chlorine or iodine, particularly bromine or iodine, and R¹ is as defined above.

The reaction according to scheme 2 is carried out if desired in the presence of a catalyst. Examples of suitable catalysts are Lewis acids, such as metal ions in the form of their salts, Zn(II) acetate being one example, Brönstedt acids, such as organic carboxylic or sulfonic acids, examples being acetic acid, adipic acid, and p-toluenesulfonic acid, or mineral acids such as sulfuric acid, Brönstedt bases, such as tertiary amines, triethylamine being one example, or mixtures of Brönstedt bases and Brönstedt acids.

The reaction is normally carried out in an organic solvent which is inert under the reaction conditions. Examples of suitable inert organic solvents include solvents containing nitrogen, e.g. aromatic nitrogen heterocycles such as pyridine, 2-methylpyridine, 3-methylpyridine, 4-methylpyridine, quinoline or isoquinoline, N,N-dialkylcarboxamides such as N,N-dimethylformamide or N,N-dimethylacetamide, N-alkyl lactams such as N-methylpyrrolidone, or aromatic solvents such as toluene or xylene.

In general the reaction takes place at a temperature between room temperature and the boiling temperature of the solvent, preferably at elevated temperature, and in particular at the boiling temperature of the solvent.

It is normal to employ the compound III and the amine IV in approximately equimolar amounts. It may, however, also be of advantage to employ one of the two reactants in excess.

It can be advantageous to remove the water formed during the reaction from the reaction mixture, employing a water separator, for example.

The reaction mixture is worked up by cooling it, diluting it with water where appropriate, and isolating the product by filtration. The product can if desired be purified in a customary way, by crystaillization or chromatography for example.

The 4-halonaphthalene-1,8-dicarboxylic anhydrides III are known from the literature or can be prepared by known methods. For bromo derivatives see, for example, Graebe, Guinsbourg, *Justus Liebigs Ann. Chem.* 1903, 327, 86 or Rule, Thompson, *J. Chem. Soc.* 1937, 1764. For the chloro derivatives see, for example, Xuhong, Shengwu, *J. Chem. Eng. Data* 1988, 33, 528-529.

The compounds I-B

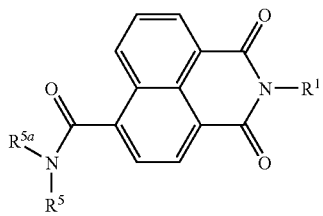

(I-B)

where $R^1$ is as defined above and $R^5$ and $R^{5a}$ each independently of one another are hydrogen, $C_1$-$C_{18}$ alkyl, aryl or heteroaryl, with aryl and heteroaryl in each case being unsubstituted or carrying one or more substituents selected from $C_1$-$C_6$ alkyl, $C_1$-$C_6$ alkoxy, hydroxyl, carboxyl, and cyano;

can be prepared for example by hydrolyzing the 4-cyanonaphthalene-1,8-dicarboxylic monoimides I-A. Where $R^5$ and $R^{5a}$ are radicals other than hydrogen, hydrolysis is followed by alkylation of the 4-aminocarbonyl compound I-B.

The hydrolysis can take place under atmospheric pressure or superatmospheric pressure. The hydrolysis can be accelerated by superatmospheric pressure, elevated temperature and/or addition of a catalyst. In one preferred embodiment the hydrolysis takes place in the presence of a catalyst. Suitable catalysts are transition metal oxides, such as iron oxides, concentrated acids such as sulfuric acid or phosphoric acid, or hydrogen peroxide in basic solution. Where concentrated acids are used as catalysts they may also act as solvents at the same time. Preference is given to using sulfuric acid as catalyst.

The hydrolysis normally takes place at temperatures between room temperature and the boiling point of the mixture: for example, at temperatures between 50 and 90° C.

Compounds of the formula I-B in which $R^5$ and/or $R^{5a}$ are other than hydrogen can be obtained for example by first subjecting a compound I-B in which $R^5$ and $R^{5a}$ are hydrogen to reaction (a) with an alkylating agent $R^5$-L    (V)

where $R^5$ is as defined above and L is a nucleophilically displaceable leaving group and, if desired, subsequently subjecting the monoalkylated reaction product obtained in step a to reaction (b) with an alkylating agent $R^{5a}$-L    (VI)

in which $R^{5a}$ is as defined above and L is a nucleophilically displaceable leaving group.

Examples of a suitable, nucleophilically displaceable leaving group L are halide, preferably chloride, bromide or iodide, sulfate, $C_1$-$C_{18}$ alkylsulfonyloxy, $C_1$-$C_{18}$ haloalkylsulfonyloxy, $C_1$-$C_{18}$ alkoxysulfonyloxy, or phenylsulfonyloxy, in which the phenyl radical is unsubstituted or substituted one or more times by halo, nitro or $C_1$-$C_6$ alkyl, such as phenylsulfonyloxy, p-toluenesulfonyloxy, p-chlorophenylsulfonyloxy, p-bromophenylsulfonyloxy or p-nitrophenylsulfonyloxy.

The alkylation is normally carried out in the presence of a base. Suitable bases include in principle any compounds capable of deprotonating the amide nitrogen atom. Examples of suitable bases include alkali metal and alkaline earth metal carbonates such as lithium carbonate, sodium carbonate, potassium carbonate, and cesium carbonate, or alkali metal and alkaline earth metal hydroxides such as sodium hydroxide, potassium hydroxide, and lithium hydroxide.

The base can be used in substoichiometric, superstoichiometric or equimolar amount, relative to the compound I-B. It is preferred to employ at least an equimolar amount of base, relative to the compound I-B.

The reaction of the compounds I-B where $R^5$ and $R^{5a}$=hydrogen with the alkylating agent (V) is advantageously carried out in the presence of a solvent. Solvents used for these reactions—depending on temperature range—are aliphatic, cycloaliphatic or aromatic hydrocarbons such as hexane, cyclohexane, toluene, and xylene, chlorinated aliphatic and aromatic hydrocarbons such as dichloromethane and chlorobenzene, open-chain dialkyl ethers such as diethyl ether, di-n-propyl ether, and methyl tert-butyl ether, cyclic ethers such as tetrahydrofuran and 1,4-dioxane, and glycol ethers such as dimethyl glycol ether, or mixtures of these solvents.

It can be advantageous to carry out the reaction in the presence of a phase transfer catalyst, especially when using inorganic bases whose solubility in the reaction medium is poor. Examples of suitable phase transfer catalysts in this context include quaternary ammonium salts or phosphonium salts. Suitable quaternary ammonium salts include tetra($C_1$-$C_{18}$ alkyl)ammonium chlorides, bromides, fluorides and tetrafluoroborates, such as tetraethylammonium chloride, tetrabutylammonium bromide, tetrabutylammonium iodide, and tetrabutylammonium tetrafluoroborate, benzyltri($C_1$-$C_{18}$ alkyl)ammonium chlorides, bromides, and fluorides, an example being benzyltriethylammmonium chloride. Suitable phosphonium salts are tetra($C_1$-$C_{18}$ alkyl)phosphonium chlorides or bromides such as tetrabutylphosphonium bromide or tetraphenylphosphonium chloride or bromide. Further suitable phase transfer catalysts are crown ethers, an example being 18-crown-6.

The reaction temperature is situated generally between room temperature and the boiling temperature of the solvent.

The reaction of the resultant compound I-B where $R^5$≠hydrogen with the alkylating agent VI for the preparation of compounds where $R^5$ and $R^{5a}$≠hydrogen takes place by a process analogous to that described above, for the preparation of compounds I-B where $R^5$≠hydrogen. With regard to suitable bases, solvents, and reaction temperatures, refer to the comments made above.

Compounds of the formula I-C

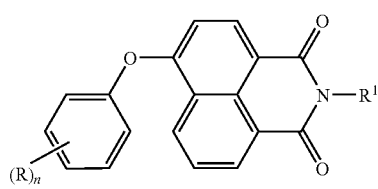

(I-C)

where $R^1$ is as defined above,

R stands for identical or different $C_1$-$C_{12}$ alkyl groups; and n is 1, 2, 3, 4 or 5 can be obtained for example by reacting a compound II with a phenol VII in accordance with the reaction sequence shown in scheme 3.

Scheme 3:

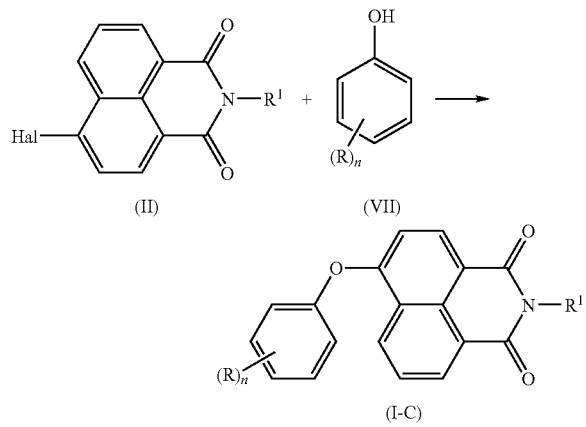

In scheme 3 Hal is halogen, such as fluorine, chlorine, bromine or iodine, preferably fluorine or chlorine. R, n and $R^1$ have the definitions given above, preferably the preferred definitions.

The reaction of the compound II with the compound VII is preferably carried out in the presence of a base. Examples of suitable inorganic bases are alkali metal and alkaline earth metal carbonates such as lithium carbonate, sodium carbonate, potassium carbonate or cesium carbonate, alkali metal and alkaline earth metal hydrogencarbonates such as lithium hydrogencarbonate, sodium hydrogencarbonate, potassium hydrogencarbonate or cesium hydrogencarbonate, alkali metal and alkaline earth metal hydroxides such as sodium hydroxide, potassium hydroxide, and lithium hydroxide, and alkali metal and alkaline earth metal hydrides such as sodium hydride and potassium hydride. Examples of suitable organic bases include tertiary amines such as trialkylamines, e.g. triethylamine, tri-n-propylamine, N-ethyldiisopropylamine, cycloaliphatic amines such as N,N-dimethylcyclohexylamine, cyclic amines such as N-methylpyrrolidine, N-ethylpiperidine, diazabicycloundecene, and diazabicyclooctane, and aromatic nitrogen heterocycles such as pyridine, α-, β- or γ-picoline, 2,4- and 2,6-lutidine, quinoline, quinazoline, quinoxaline, p-dimethylaminopyridine, pyrimidine and the like.

In the case of salts whose solubility in the reaction medium is poor it can be of advantage to carry out the reaction in the presence of a phase transfer catalyst. Examples of suitable phase transfer catalysts in this context include quaternary ammonium salts or phosphonium salts. Suitable quaternary ammonium salts include tetra($C_1$-$C_{18}$ alkyl)ammonium chlorides, bromides, fluorides and tetrafluoroborates, such as tetraethylammonium chloride, tetrabutylammonium bromide, tetrabutylammonium iodide, and tetrabutylammonium tetrafluoroborate, benzyltri($C_1$-$C_{18}$ alkyl)ammonium chlorides, bromides, and fluorides, an example being benzyltriethylammmonium chloride. Suitable phosphonium salts are tetra ($C_1$-$C_{18}$ alkyl)phosphonium chlorides or bromides such as tetrabutylphosphonium bromide or tetraphenylphosphonium chloride or bromide. Further suitable phase transfer catalysts are crown ethers, an example being 18-crown-6.

The reaction is normally carried out in an organic solvent. Examples of suitable organic solvents are solvents containing nitrogen, such as aromatic nitrogen heterocycles like pyridine, 2-methylpyridine, 3-methylpyridine, 4-methylpyridine, isoquinoline or quinoline, N,N-dialkylcarboxamides such as N,N-dimethylformamide or N,N-dimethylacetamide, N-alkyl lactams such as N-methylpyrrolidone, and aromatic solvents such as xylene or toluene.

Generally speaking, the reaction takes place at a temperature between room temperature and the boiling temperature of the solvent, preferably at elevated temperature, and in particular at the boiling temperature of the solvent.

The compound II and the phenol VII are normally employed in approximately equimolar amounts. It can, however, also be of advantage to use one of the two reactants in excess.

The reaction mixture is generally worked up by cooling it, diluting it where appropriate with water or a lower alcohol, and isolating the product by filtration. Where appropriate the product can be purified in a customary way, by crystallization or chromatography for example.

The naphthalene-1,8-dicarboxylic monoimides of the formula I are capable of absorbing in the wavelength range below 400 nm with preference, and below 390 nm in particular. The transmittance of the stabilized material for electromagnetic radiation with a wavelength between 340 nm and 380 nm is preferably not greater than 10%.

The naphthalene-1,8-dicarboxylic monoimides I used in accordance with the invention are suitable for protecting organic material. Organic material for the purposes of the present invention embraces both living organic material and inanimate organic material. Protection is meant in the sense both of stabilization, as obtained by mixing the material to be protected with at least one naphthalene-1,8-dicarboxylic monoimide of the formula I, and the protection of the materials which are least partly surrounded by a directly protected material (in the form of packaging, for example). An example of living organic material is skin and an example of inanimate organic material is hair. Examples of inanimate organic material also include, for example, foods, cleaning products, perfumes, textiles, paper, furniture, carpets, plastic moldings such as electrical housings, cosmetic preparations such as ointments, creams, gels, emulsions, and lotions, drug formulations such as drops, emulsions, solutions, pills, tablets, and suppositories, paints, photographic emulsions, photographic layers, and particularly plastics and polymer dispersions.

One preferred embodiment of the present invention relates to the use of at least one naphthalene-1,8-dicarboxylic monoimide of the formula I to protect inanimate organic material.

The naphthalene-1,8-dicarboxylic monoimides I are used in particular for protecting plastics. The naphthalene-1,8-dicarboxylic monoimides I used in accordance with the invention show themselves to be highly compatible with plastics, so that the optical properties of the polymer are unaffected. Moreover, many of the naphthalene-1,8-dicarboxylic monoimides I used in accordance with the invention display a weak fluorescence, so that additizing the plastic with at least one naphthalene-1,8-dicarboxylic monoimide I is capable of masking or reducing any intrinsic yellow coloration of the plastic. Preferred plastics are those which are transparent in the uncolored state in the visible wavelength range. These include not only homopolymers and copolymers but also physical blends of polymers (polymer mixtures). Copolymers for the purposes of the present invention are copolymers formed by (joint) copolymerization of two or more different monomers. It will be appreciated that copolymers such as polyesters may also include transesterification products, depending on their preparation and/or processing. As far as preparation and/or processing are concerned, in the case of copolymers it is also possible for grafting or graft transfer operations to take place.

Naphthalene-1,8-dicarboxylic monoimide I used in accordance with the invention protects plastic against the consequences of light exposure and in the case of transparent plastics also protects living and/or inanimate organic material at least partly surrounded by the directly protected plastic against the damaging effects of light.

One embodiment of the present invention relates to the use of naphthalene-1,8-dicarboxylic monoimides I in plastics used as packaging materials.

The plastics preferably comprise at least one polymer selected from polyesters, polycarbonates, polystyrene, copolymers of styrene or α-methylstyrene with dienes and/or acrylic derivatives, polyurethanes, polyvinyl acetals, polyolefins, polyacrylates, polymethacrylates, and physical blends of said polymers.

Preference is given to polymers and polymer mixtures (polymer blends) which can be processed to highly transparent, glass-clear packs or packaging materials.

In one preferred embodiment of the present invention the polyvinyl acetal is a polyvinyl butyral. In another preferred embodiment of the present invention the thermoplastic molding compound comprises at least one polycarbonate polymer selected from polycarbonates, polycarbonate copolymers, and physical blends based on polycarbonates with acrylonitrile-butadiene-styrene copolymers, acrylonitrile-styrene-acrylate copolymers, polymethyl methacrylates, polybutyl acrylates, polybutyl methacrylates, poly(butylene terephthalate)s, and polyethylene terephthalates. In a further preferred embodiment of the present invention the polyester is a polyethylene terephthalate. In another preferred embodiment of the present invention the polyolefin is a high-density polyethylene or a polypropylene. In another preferred embodiment of the present invention the copolymer of styrene with dienes and/or acrylic derivatives is an acrylonitrile-butadiene-styrene copolymer or a styrene-acrylonitrile copolymer.

In one preferred embodiment of the invention the plastic comprises as polymer at least one polyester, preferably at least one linear polyester. Suitable polyesters and copolyesters are described in EP-A-0678376, EP-A-0 595 413 and U.S. Pat. No. 6,096,854, hereby incorporated by reference. Polyesters, as is known, are condensation products of one or more polyols and one or more polycarboxylic acids. In linear polyesters the polyol is a diol and the polycarboxylic acid is a dicarboxylic acid. The diol component may be selected from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, and 1,3-cyclohexanedimethanol. Also suitable are diols whose alkylene chain is interrupted one or more times by nonadjacent oxygen atoms. Such diols include diethylene glycol, triethylene glycol, dipropylene glycol, tripropylene glycol, and the like. In general the diol contains from 2 to 18 carbon atoms, preferably 2 to 8 carbon atoms. Cycloaliphatic diols can be used in the form of their cis or trans isomer or as an isomer mixture. The acid component can be an aliphatic, alicyclic or aromatic dicarboxylic acid. the acid component of linear polyesters is generally selected from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalenedicarboxylic acid, and mixtures thereof. It will be appreciated that the functional derivatives of the acid component can also be used, such as esters, the methyl ester for example, anhydrides or halides, preferably chlorides. Preferred polyesters are polyalkylene terephthalates and polyalkylene naphthalates obtainable by condensing terephthalic acid or naphthalenedicarboxylic acid, respectively, with an aliphatic diol.

Particularly preferred polyalkylene terephthalates are polyethylene terephthalates (PET), which are obtained by condensing terephthalic acid with diethylene glycol. PET is also obtainable by transesterifying dimethyl terephthalate with ethylene glycol, with elimination of methanol, to form bis(2-hydroxyethyl)terephthalate, and subjecting the product to polycondensation, releasing ethylene glycol. Further preferred polyesters are polybutylene terephthalates (PBT), obtainable by condensing terephthalic acid with 1,4-butanediol, polyethylene 2,6-naphthalate (PEN), poly-1,4-cyclohexanedimethylene terephthalates (PCT), and also copolyesters of polyethylene terephthalate with cyclohexanedimethanol (PDCT) and of polybutylene terephthalate with cyclohexanedimethanol. Preference is likewise given to copolymers, transesterification products, and physical mixtures (blends) of the aforementioned polyalkylene terephthalates. Particularly suitable thermoplastic molding compounds are selected from polycondensates and copolycondensates of terephthalic acid, such as poly- or copolyethylene terephthalate (PET or CoPET or PETG), poly(ethylene 2,6-naphthalate)s (PEN) or PEN/PET copolymers and PEN/PET blends. Said copolymers and blends, depending on their preparation process, may also include fractions of transesterification products.

In further preferred embodiment of the invention the plastic comprises polycarbonates as polymers. Polycarbonates are formed, for example, by condensation of phosgene or carbonic esters such as diphenyl carbonate or dimethyl carbonate with dihydroxy compounds. Suitable dihydroxy compounds are aliphatic or aromatic dihydroxy compounds. Examples of aromatic dihydroxy compounds include bisphenols such as 2,2-bis(4-hydroxyphenyl)propane(bisphenol A), tetraalkylbisphenol A, 4,4-(meta-phenylenediisopropyl)diphenol(bisphenol M), 4,4-(para-phenylenediisopropyl)diphenol, 1,1-bis(4-hydroxyphenyl)-3,3,5-trimethylcyclohexane (BP-TMC), 2,2-bis(4-hydroxyphenyl)-2-phenylethane, 1,1-bis(4-hydroxyphenyl)cyclohexane (bisphenol Z) and, where appropriate, mixtures thereof. The polycarbonates may be branched by using small amounts of branching agents. Suitable branching agents include phloroglucinol, 4,6-dimethyl-2,4,6-tri(4-hydroxyphenyl)hept-2-ene, 4,6-dimethyl-2,4,6-tri(4-hydroxyphenyl)heptane; 1,3,5-tri(4-hydroxyphenyl)benzene; 1,1,1-tri(4-hydroxyphenyl)heptane; 1,3,5-tri(4-hydroxyphenyl)benzene; 1,1,1-tri(4-hydroxyphenyl)-ethane; tri(4-hydroxyphenyl)phenylmethane, 2,2-bis[4,4-bis(4-hydroxyphenyl)cyclohexyl]propane; 2,4-bis(4-hydroxyphenylisopropyl)phenol; 2,6-bis(2-hydroxy-5'-methylbenzyl)-4-methylphenol; 2-(4-hydroxyphenyl)-2-(2,4-dihydroxyphenyl)propane; hexa(4-(4-hydroxyphenylisopropyl)phenyl)orthoterephthalate; tetra(4-hydroxyphenyl)-methane; tetra(4-(4-hydroxyphenylisopropyl)phenoxy)methane; α,α',α''-tris(4-hydroxyphenyl)-1,3,5-triisopropylbenzene; 2,4-dihydroxybenzoic acid; trimesic acid; cyanuric chloride; 3,3-bis(3-methyl-4-hydroxyphenyl)-2-oxo-2,3-dihydroindole, 1,4-bis(4',4''-dihydroxytriphenyl)methyl)benzene, and, in particular, 1,1,1-Tri(4-hydroxyphenyl)ethane and bis(3-methyl-4-hydroxyphenyl)-2-oxo-2,3-dihydroindole.

For chain termination, suitability is possessed by, for example, phenols such as phenol, alkylphenols such as cresol and 4-tert-butylphenol, chlorophenol, bromophenol, cumylphenol or mixtures thereof. The fraction of chain terminators is generally from 1 to 20 mol %, per mole of dihydroxy compound.

In another suitable embodiment of the invention the plastic comprises polymers derived from α,β-unsaturated acids and derivatives thereof, e.g., poly(meth)acrylates such as polymethyl methacrylate (PMMA) and polyethyl methacrylate.

In a further suitable embodiment of the invention the plastic comprises as polymer a vinylaromatic homopolymer or copolymer such as polystyrene (PS) or copolymers of styrene or α-methylstyrene with dienes and/or acrylic derivatives, such as styrene-butadiene, styrene-acrylonitrile (SAN), styrene-ethyl methacrylate, styrene-butadiene-ethyl acrylate, styrene-acrylonitrile-methacrylate, acrylonitrile-butadiene-styrene (ABS) or methyl methacrylate-butadiene-styrene (MBS).

In a further suitable embodiment of the invention the plastic comprises polymers derived from unsaturated alcohols and amines or from their acrylic derivatives or acetates, such as polyvinyl acetate (PVAC) and polyvinyl alcohol (PVAL). The reaction of polyvinyl alcohol with an aldehyde forms polyvinyl acetals: for example, polyvinyl formals (PVFM) on reaction with formaldehyde, or the polyvinyl butyrals (PVB) with butyraldehyde.

In laminated glass, two or more sheets of glass are bonded together adhesively through polyvinyl butyral films. The polyvinyl butyral molding compound generally has an average molecular mass of more than 70 000, preferably from about 100 000 to 250 000. The polyvinyl butyral generally has a residual hydroxyl group content of less than 19.5%, preferably from about 17% to 19% by weight, calculated as polyvinyl alcohol, and a residual ester group content of from 0 to 10%, preferably from 0 to 3%, calculated as polyvinyl ester. An exemplary PVB is obtainable commercially under the name Butvar® from Solutia, Inc. of St. Louis, Mo. Any glass is suitable provided it is transparent for light in the visible wavelength range. Such glasses include normal clear soda-lime glass, IR-reflecting coated glass or IR-absorbing glass; see, e.g., U.S. Pat. No. 3,944,352 and U.S. Pat. No. 3,652,303. With respect to the configuration of laminated glass, the entirety of WO 02/077081, and in particular pages 28 to 32, is hereby incorporated by reference.

For the purposes of the present invention the term "polyolefin" embraces all polymers synthesized from olefins without further functionality, such as low or high density polyethylene, polypropylene, linear polybut-1-ene or polyisobutylene or polybutadiene, and also copolymers of monoolefins or diolefins. Preferred polyolefins are the homopolymers and copolymers of ethylene and also the homopolymers and copolymers of propylene.

Ethylene Polymers:

Suitable polyethylene (PE) homopolymers are, for example:

PE-LD (LD=low density), obtainable for example by the high-pressure process (ICI) at 1000 to 3000 bar and 150 to 300° C. with oxygen or peroxide catalysts in autoclaves or tube reactors. Highly branched with branches of different length, crystallinity 40 to 50%, density 0.915 to 0.935 g/cm$^3$, average molar mass up to 600 000 g/mol.

PE-LLD (LLD=linear low density), obtainable with metal complex catalysts in the low-pressure process from the gas phase, from a solution (e.g., mineral spirit), in a suspension or with a modified high-pressure process. Slight branching with side chains which are themselves unbranched, molar masses higher than for PE-LD.

PE-HD (HD=high density), obtainable by the medium-pressure (Phillips) and low-pressure (Ziegler) processes. According to Phillips at 30 to 40 bar, 85 to 180° C., chromium oxide catalyst, molar masses about 50 000 g/mol. According to Ziegler at 1 to 50 bar, 20 to 150° C., titanium halide, titanic ester or aluminum alkyl catalysts, molar mass about 200 000 to 400 000 g/mol. Carried out in suspension, solution, gas phase or bulk. Very slight branching, crystallinity 60 to 80%, density 0.942 to 0.965 g/cm$^3$.

PE-HD-HMW (HMW=high molecular weight), obtainable by Ziegler, Phillips or gas-phase method. High density and high molar mass.

PE-HD-UHMW (UHMW=ultra-high molecular weight) obtainable with modified Ziegler catalyst, molar mass 3 000 000 to 6 000 000 g/mol.

Particular suitability is possessed by polyethylene prepared in a gas-phase fluidized-bed process using (normally supported) catalysts, e.g., Lupolen® (Basell).

Particular preference is given to polyethylene prepared using metallocene catalysts. Polyethylene of this kind is available commercially as Luflexen® (Basell), for example.

Suitable ethylene copolymers include all commercially customary ethylene copolymers, examples being Luflexen® grades (Basell), Nordel®, and Engage® (Dow, DuPont). Examples of suitable comonomers include α-olefins having 3 to 10 carbon atoms, especially propylene, but-1-ene, hex-1-ene, and oct-1-ene, and also alkyl acrylates and methacrylates having 1 to 20 carbon atoms in the alkyl radical, especially butyl acrylate. Further suitable comonomers are dienes such as butadiene, isoprene, and octadiene, for example. Other suitable comonomers are cycloolefins, such as cyclopentene, norbornene, and dicyclopentadiene.

The ethylene copolymers are normally random copolymers or block or impact copolymers. Suitable block or impact copolymers of ethylene and comonomers are, for example, polymers for which in the first stage a homopolymer of the comonomer or a random copolymer of the comonomer is prepared, containing up to 15% by weight ethylene, for example, and then in the second stage a comonomer-ethylene copolymer with ethylene contents of 15 to 80% by weight is polymerized on. Ordinarily, sufficient of the comonomer-ethylene copolymer is polymerized on for the copolymer produced in the second stage to have a fraction of from 3 to 60% by weight in the end product.

The polymerization for preparing the ethylene-comonomer copolymers can take place by means of Ziegler-Natta catalyst system. It is, however, also possible to use catalyst systems based on metallocene compounds or based on polymerization-active metal complexes.

Propylene Polymers:

Polypropylene should be understood below to refer both to homopolymers and to copolymers of propylene. Copolymers of propylene contain minor amounts of monomers copolymerizable with propylene, examples being $C_2$-$C_8$ alk-1-enes such as ethylene, but-1-ene, pent-1-ene or hex-1-ene, among others. Two or more different comonomers can also be used.

Suitable polypropylenes include homopolymers of propylene or copolymers of propylene with up to 50% by weight of copolymerized other alk-1-enes having up to 8 carbon atoms. The copolymers of propylene are in this case random copolymers or block or impact copolymers. Where the copolymers of propylene are of random construction they contain generally up to 15% by weight, preferably up to 6% by weight, of other alk-1-enes having up to 8 carbon atoms, especially ethylene, but-1-ene or a mixture of ethylene and but-1-ene.

Suitable block or impact copolymers of propylene are, for example, polymers for which in the first stage a propylene homopolymer or a random copolymer of propylene with up to 15% by weight, preferably up to 6% by weight, of other alk-1-enes having up to 8 carbon atoms is prepared and then in the second stage a propylene-ethylene copolymer having ethylene contents of from 15 to 80% by weight is polymerized on, it being possible for the propylene-ethylene copolymer further to include other $C_4$-$C_8$ alk-1-enes. Ordinarily, sufficient of the propylene-ethylene copolymer is polymerized on that the copolymer produced in the second stage has a fraction of from 3 to 60% by weight in the end product.

The polymerization for the preparation of polypropylene can take place by means of a Ziegler-Natta catalyst system. Use is made in particular of catalyst systems which in addition to a solid component a) containing titanium also contain cocatalysts in the form of organic aluminum compounds b) and electron donor compounds c).

It is also possible, however, to use catalyst systems based on metallocene compounds or based on polymerization-active metal complexes.

The preparation of the polypropylenes is normally carried out by polymerization in at least one reaction zone or, frequently, in two or more reaction zones connected in series (a reactor cascade), in the gas phase, in a suspension, or in a liquid phase (bulk phase). The reactors used can be the normal reactors used for polymerizing $C_2$-$C_8$ alk-1-enes. Suitable reactors include continuous stirred tanks, loop reactors, powder bed reactors or fluidized bed reactors.

The polymerization for preparing the polypropylenes used is operated under normal reaction conditions at temperatures from 40 to 120° C., in particular from 50 to 100° C., and pressures from 10 to 100 bar, in particular from 20 to 50 bar. Suitable polypropylenes normally have a melt flow rate (MFR) in accordance with ISO 1133 of from 0.1 to 200 g/10 min., in particular from 0.2 to 100 g/10 min., at 230° C. and under a weight of 2.16 kg.

In another embodiment of the invention the plastic comprises at least one polyolefin. Preferred polyolefins contain at least one copolymerized monomer selected from ethylene, propylene, but-1-ene, isobutylene, 4-methyl-1-pentene, butadiene, isoprene, and mixtures thereof. Suitability is possessed by homopolymers, copolymers of the stated olefin monomers, and copolymers of at least one of said olefins as principal monomer, with other monomers (such as vinylaromatics, for example) as comonomers.

Preferred polyolefins are low density polyethylene homopolymers (PE-LD) and polypropylene homopolymers and polypropylene copolymers. Preferred polypropylenes are, for example, biaxially oriented polypropylene (BOPP) and crystallized polypropylene.

In another embodiment of the invention the plastic comprises as polymer at least one polyurethane. Polyurethanes are, generally speaking, addition products of at least one diisocyanate and at least one diol component, which may also contain higher polyfunctional isocyanates, triisocyanates for example, and higher polyfunctional polyols. Suitable isocyanates are aromatic diisocyanates such as 2,4- and 2,6-tolylene diisocyanate (TDI) and isomer mixtures thereof, tetramethylxylene diisocyanate (TMXDI), xylene diisocyanate (XDI), and diphenylmethane 4,4'-diisocyanate (MDI), and aliphatic diisocyanates, such as dicylohexylmethane 4,4'-diisocyanate ($H_{12}$MDI), tetramethylene diisocyanate, hexamethylene diisocyanate (HMDI), isophorone diisocyanate (IPDI), trimethylhexamethylene diisocyanate, and mixtures thereof. The preferred diisocyanates include hexamethylene diisocyanate (HMDI) and isophorone diisocyanate. Also suitable for preparing polyurethanes are triisocyanates, e.g. triphenylmethane 4,4',4"-triisocyanate, and the cyanurates and biurets of the aforementioned diisocyanates.

Suitable diols are glycols having preferably 2 to 25 carbon atoms. These include 1,2-ethanediol, 1,2-propanediol, 1,3-propanediol, 1,4-butanediol, 1,5-pentanediol, 1,6-hexanediol, 1,10-decanediol, diethylene glycol, 2,2,4-trimethylpentane-1,5-diol, 2,2-dimethylpropane-1,3-diol, 1,4-dimethylolcyclohexane, 1,6-dimethylolcyclohexane, 2,2-bis(4-hydroxyphenyl)propane(bisphenol A), 2,2-bis(4-hydroxyphenyl)butane(bisphenol B) or 1,1-bis(4-hydroxyphenyl)-3,3,5-trimethylcyclohexane(bisphenol C).

Polyols are also useful starting materials for preparing polyurethanes. By polyols are meant trivalent alcohols (known as triols) and higher polyfunctional alcohols. They have generally 3 to 25, preferably 3 to 18, carbon atoms. They include glycerol, trimethylolethane, trimethylolpropane, erythritol, pentaerythritol, sorbitol, and the alkoxylates thereof.

In one preferred embodiment of the present invention the plastic is a thermoplastic molding compound. The transmittance of the uncolored thermoplastic molding compound for electromagnetic radiation with a wavelength between 420 nm and 800 nm is preferably greater than 90%.

The present invention further provides for the use of at least one naphthalene-1,8-dicarboxylic monoimide I for preparing a layer which absorbs ultraviolet light. The absorbent layer is preferably transparent in the wavelength range between 420 and 800 nm.

The ultraviolet-absorbing, preferably transparent layer is based on a thermoplastic molding compound. Suitable thermoplastic molding compounds include thermoplastics comprising at least one polymer selected from polyesters, polycarbonates, polyolefins, polyvinyl acetals, polystyrene, copolymers of styrene or of α-methylstyrene with dienes and/or acrylic derivatives, and also hybrid forms of the aforementioned polymers.

In one preferred embodiment of the present invention the transparent layer is part of an architectural or automotive glazing system or is a sheet intended for adhesive bonding to glass or plastic for purposes of insulation or filtering; in particular it is part of a laminated window in automotive glazing. In one particularly preferred embodiment the plastic sheet comprises a polyvinyl acetal, in particular polyvinyl butyral.

The naphthalene-1,8-dicarboxylic monoimide I in the laminated glass acts as a UV absorber to protect living organic and inanimate organic material, so that, for example, the driver and the inanimate organic material present in the car interior are protected against the damaging effects of ultraviolet radiation. Examples of possible damage include erythema or sunburn in the case of living organic material and yellowing, discoloration, cracking or embrittlement in the case of inanimate organic material.

Optionally the plastic further comprises at least one other light stabilizer which absorbs light radiation in the UV-A and/or UV-B region, and/or further (co)stabilizers. The light stabilizer and, where appropriate, (co)stabilizers used additionally must of course be compatible with the naphthalene-1,8-dicarboxylic monoimide I. In the visible range they are preferably colorless or have only a slight inherent coloration. The light stabilizers and/or (co)stabilizers, where used, preferably have high migration fastness and temperature stability. Suitable light stabilizers and further (co)stabilizers are selected, for example, from groups a) to s):

a) 4,4-diarylbutadienes,
b) cinnamic esters,
c) benzotriazoles,
d) hydroxybenzophenones,
e) diphenylcyanacrylates, f) oxamides,
g) 2-phenyl-1,3,5-triazines;
h) antioxidants,
i) nickel compounds,
j) sterically hindered amines,
k) metal deactivators,
l) phosphites and phosphonites,
m) hydroxylamines,
n) nitrones,
o) amine oxides,
p) benzofuranones and indolinones,
q) thiosynergists,
r) peroxide-destroying compounds, and
s) basic costabilizers.

Group a) of the 4,4-diarylbutadienes includes for example compounds of the formula A.

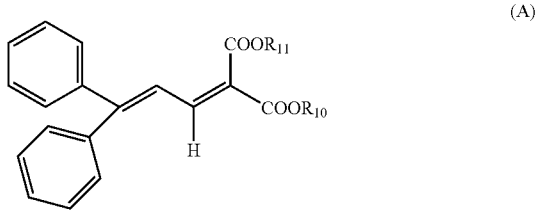

(A)

The compounds are known from EP-A-916 335. The substituents $R_{10}$ and/or $R_{11}$ are preferably $C_1$-$C_8$ alkyl and $C_5$-$C_8$ cycloalkyl.

Group b) of the cinnamic esters includes for example 2-isoamyl 4-methoxycinnamate, 2-ethylhexyl 4-methoxycinnamate, methyl α-methoxycarbonylcinnamate, methyl α-cyano-β-methyl-p-methoxycinnamate, butyl α-cyano-β-methyl-p-methoxycinnamate, and methyl α-methoxycarbonyl-p-methoxycinnamate.

Group c) of the benzotriazoles includes for example 2-(2'-hydroxyphenyl)-benzotriazoles such 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl) benzotriazole, 2-(2'-hydroxy-5'-(1,1,3,3-tetramethylbutyl) phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)-benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy) carbonylethyl]-2'-hydroxyphenyl)-5-chlorobenzotriazole, 2-(3'-tert-butyl-2'-hydroxy-5'-(2-methoxycarbonylethyl) phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxy-carbonylethyl) phenylbenzotriazole, 2,2'-methylenebis[4-(1,1,3,3-tetramethylbutyl)-6-benzotriazol-2-ylphenol]; the product of esterifying 2-[3'-tert-butyl-5'-(2-methoxycarbonylethyl)-2'-hydroxyphenyl]-2H-benzotriazole with polyethylene glycol 300; [R—$CH_2CH_2$—COO($CH_2$)$_3$]$_2$ where R=3'-tert-butyl-4'-hydroxy-5'-2H-benzotriazol-2-ylphenyl and mixtures thereof.

Group d) of the hydroxybenzophenones includes for example 2-hydroxybenzophenones such as 2-hydroxy-4-methoxybenzophenone, 2,2'-dihydroxy-4-methoxybenzophenone, 2,4-dihydroxybenzophenone, 2,2',4,4'-tetrahydroxybenzophenone, 2,2'-dihydroxy-4,4'-dimethoxybenzophenone, 2,2'-dihydroxy-4,4'-dimethoxybenzophenone, 2-hydroxy-4-(2-ethylhexyloxy) benzophenone, 2-hydroxy-4-(n-octyloxy)benzophenone, 2-hydroxy-4-methoxy-4'-methylbenzophenone, 2-hydroxy-3-carboxybenzophenone, 2-hydroxy-4-methoxybenzophenone-5-sulfonic acid and its sodium salt, and 2,2'-dihydroxy-4,4'-dimethoxybenzophenone-5,5'-bissulfonic acid and its sodium salt.

Group e) of the diphenylcyanoacrylates includes for example ethyl 2-cyano-3,3-diphenylacrylate, obtainable commercially for example under the name Uvinul® 3035 from BASF AG, Ludwigshafen, 2-ethylhexyl 2-cyano-3,3-diphenylacrylate, obtainable commercially for example as Uvinul® 3039 from BASF AG, Ludwigshafen, and 1,3-bis [(2'-cyano-3',3'-diphenylacryloyl)oxy]-2,2-bis{[2'-cyano-3', 3'-diphenyl-acryloyl)oxy]methyl}propane, obtainable commercially for example under the name Uvinul® 3030 from BASF AG, Ludwigshafen.

Group f) of the oxamides includes for example 4,4'-dioctyloxyoxanilide, 2,2'-di-ethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, and also mixtures of ortho-, para-methoxy-disubstituted oxanilides and mixtures of ortho- and para-ethoxy-disubstituted oxanilides.

Group g) of the 2-phenyl-1,3,5-triazines includes for example 2-(2-hydroxyphenyl)-1,3,5-triazines such 2,4,6-tris (2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2, 4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazin, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropoxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy) phenyl]-4,6-bis-(2,4-dimethylphenyl)-1,3,5-triazine, 2-(2-hydroxy-4-hexyloxyphenyl)-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy) phenyl]-1,3,5-triazine, and 2-(2-hydroxyphenyl)-4-(4-methoxyphenyl)-6-phenyl-1,3,5-triazine.

Group h) of the antioxidants comprises, for example:

h.1) Alkylated monophenols such as, for example, 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, unbranched or sidechain-branched nonylphenols such as, for example, 2,6-dinonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl)phenol, and mixtures thereof.

h.2) Alkylthiomethylphenols such as, for example, 2,4-dioctylthiomethyl-6-tert-butylphenol, 2,4-dioctylthiomethyl-6-methylphenol, 2,4-dioctylthiomethyl-6-ethylphenol and 2,6-didodecylthiomethyl-4-nonylphenol.

h.3) Hydroquinones and alkylated hydroquinones such as, for example, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, and bis-(3,5-di-tert-butyl-4-hydroxyphenyl)adipate.

h.4) Tocopherols, such as, for example, α-tocopherol, β-tocopherol, γ-tocopherol, δ-tocopherol, and mixtures thereof (vitamin E).

h.5) Hydroxylated thiodiphenyl ether such as, for example, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), and 4,4'-bis(2,6-dimethyl-4-hydroxyphenyl)disulfide.

h.6) Alkylidenebisphenols such as, for example, 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3-tert-butyl-4-hydroxyphenyl)butyrate], bis(3-tert-butyl-4-hydroxy-5-methyl-phenyl)dicyclopentadiene, bis[2-(3'-tert-butyl-2-hydroxy-5-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methylphenyl)pentane.

h.7) Benzyl compounds such as, for example, 3,5,3',5'-tetratert-butyl-4,4'-dihydroxydibenzyl ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl-4-hydroxybenzyl)amine, 1,3,5-tri(3,5-di-tert-butyl-4-hydroxybenzyl)-2,4,6-trimethylbenzene, di(3,5-di-tert-butyl-4-hydroxybenzyl)sulfide, isooctyl 3,5-di-tert-butyl-4-hydroxybenzylmercaptoacetate, bis(4-tert-butyl-3-hydroxy-2,6-dimethylbenzyl)dithiol terephthalate, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 3,5-di-tert-butyl-4-hydroxybenzyl-phosphoric acid dioctadecyl ester, and 3,5-di-tert-butyl-4-hydroxybenzyl-phosphoric acid monoethyl ester, calcium salt.

h.8) Hydroxybenzylated malonates such as, for example, dioctadecyl 2,2-bis(3,5-di-tert butyl-2-hydroxybenzyl)malonate, dioctadecyl-2-(3-tert-butyl-4-hydroxy-5-methylbenzyl)malonate, didodecyl mercaptoethyl-2,2-bis(3,5-di-tert-butyl-4-hydroxybenzyl)malonate, and bis[4-(1,1,3,3-tetramethylbutyl)phenyl]2,2-bis(3,5-di-tert-butyl-4-hydroxybenzyl)malonate.

h.9) Hydroxybenzyl aromatics such as, for example, 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, and 2,4,6-tris(3,5-di-tert-butyl-4-hydroxybenzyl)phenol.

h.10) Triazine compounds such as, for example, 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, and 1,3,5-tris(3,5-dicyclohexyl-4-hydroxybenzyl)isocyanurate.

h.11) Benzylphosphonates such as, for example, dimethyl 2,5-di-tert-butyl-4-hydroxybenzylphosphonate, diethyl 3,5-di-tert-butyl-4-hydroxybenzylphosphonate(diethyl(3,5-bis(1,1-dimethylethyl)-4-hydroxyphenyl)methylphosphonate, dioctadecyl 3,5-di-tert-butyl-4-hydroxybenzylphosphonate, dioctadecyl 5-tert-butyl-4-hydroxy-3-methylbenzylphosphonate, and the calcium salt of monoethyl 3,5-di-tert-butyl-4-hydroxybenzylphosphonate.

h.12) Acylaminophenols such as, for example, 4-hydroxylauranilide, 4-hydroxystearanilide, 2,4-bisoctylmercapto-6-(3,5-tert-butyl-4-hydroxyanilino)-s-triazine, and octyl N-(3,5-di-tert-butyl-4-hydroxyphenyl)carbamate.

h.13) Esters of β-(3,5-di-tert-butyl-4-hydroxyphenyl)propionic acid with monohydric or polyhydric alcohols, such as with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, and 4-hydroxymethyl-1-phospha-2,6,7-trioxabicyclo[2.2.2]octane.

h.14) Esters of β-(5-tert-butyl-4-hydroxy-3-methylphenyl) propionic acid with monohydric or polyhydric alcohols, such as with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, and 4-hydroxymethyl-1-phospha-2,6,7-trioxabicyclo[2.2.2]octane.

h.15) Esters of β-(3,5-dicyclohexyl-4-hydroxyphenyl)propionic acid with monohydric or polyhydric alcohols, such as with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, and 4-hydroxymethyl-1-phospha-2,6,7-trioxabicyclo[2.2.2]octane.

h.16) Esters of 3,5-di-tert-butyl-4-hydroxyphenylacetic acid with monohydric or polyhydric alcohols, such as with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, and 4-hydroxymethyl-1-phospha-2,6,7-trioxabicyclo[2.2.2]octane.

h.17) Amides of β-(3,5-di-tert-butyl-4-hydroxyphenyl)propionic acid, such as N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl] oxamide (e.g. Naugard® XL-1 from Uniroyal).

h.18) Ascorbic acid (vitamin C)

h.19) Amine antioxidants, such as, for example, N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl) diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example, p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl) amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane,1,2-bis (phenylamino)propane, o-tolyl biguanide, bis[4-(1',3'-dimethylbutyl)-phenyl]amine, tert-octylated N-phenyl-1-naphthylamine, a mixture o mono- and dialkylated tert-butyl/tert-octyldiphenylamines, a mixture of mono- and dialkylated nonyldiphenylamines, a mixture of mono- and dialkylated dodecyidiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperidin-4-yl)hexamethylenediamine, bis(2,2,6,6-tetramethylpiperidin-4-yl)sebacate, 2,2,6,6-tetramethylpiperidin-4-one, 2,2,6,6-tetramethylpiperidin-4-ol, the dimethyl succinate polymer with 4-hydroxy-2,2,6,6-tetramethyl-1-piperidineethanol [CAS number 65447-77-0], (for example, Tinuvin® 622 from Ciba Specialty Chemicals, Inc.), polymer of 2,2,4,4-tetramethyl-7-oxa-3,20-diazadispiro[5.1.11.2]heneicosan-21-one and epichlorohydrin [CAS No.: 202483-55-4], (for example Hostavin® 30 from Ciba Specialty Chemicals, Inc.).

Group i) of the nickel compounds includes for example nickel complexes of 2,2'-thiobis[4-(1,1,3,3-tetramethylbutyl) phenol], such as the 1:1 or 1:2 complex, with or without additional ligands such as n-butylamine, triethanolamine or N-cyclohexyldiethanolamine, nickel dibutyl dithiocarbamate, nickel salts of 4-hydroxy-3,5-di-tert-butylbenzylphosphonic acid monoalkyl esters such as of the methyl or ethyl esters, for example, nickel complexes of ketoximes such as, for example, of 2-hydroxy-4-methylphenyl undecyl ketoxime, and the nickel complex of 1-phenyl-4-lauroyl-5-hydroxypyrazole, with or without additional ligands.

Group j) of the sterically hindered amines includes for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl)n-butyl-3,5-di-tert-butyl-4-hydroxybenzylmalonate(n-butyl-3,5-di-tert-butyl-4-hydroxybenzylmalonic acid bis(1,2,2,6,6-pentamethylpiperidyl)ester), condensation product of 1-(2-hydroxyethyl)-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)1,2,3,4-butanetetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)2-n-butyl-2-(2-hydroxy-3,5-di-tert-butylbenzyl)malonate, 3-n-octyl-7,7,9,9-tetramethyl-1,3,8-triazaspiro[4.5] decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensation products of N,N'-bis(2,2,6,6-tetramethyl-4-piperidyl)hexamethylenediamine and 4-morpholino-2,6-dichloro-1,3,5-triazine, condensation product of N,N'-bis(2,2,6,6-tetramethyl-4-piperidyl)hexamethylenediamine and formic esters (CAS No. 124172-53-8, e.g., Uvinul® 4050H from BASF AG, Ludwigshafen), condensation product of 2-chloro-4,6-bis(4-n-butylamino-2,2,6,6-tetramethylpiperidyl)-1,3,5-triazine and 1,2-bis(3-aminopropylamino)ethane, condensation product of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, mixture of 4-hexadecyloxy- and 4-stearyloxy-2,2,6,6-tetramethylpiperidine, condensation product of N,N'-bis(2,2,6,6-tetramethyl-4-piperidyl)hexamethylenediamine and 4-cyclohexylamino-2,6-dichloro-1,3,5-triazine, condensation product of 1,2-bis(3-aminopropylamino)ethane and 2,4,6-trichloro-1,3,5-triazine and also 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro [4.5]decane, reaction product of 7,7,9,9-tetramethyl-2-cycloundecyl-1-oxa-3,8-diaza-4-oxospiro[4.5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, diester of 4-methoxymethylenemalonic acid with 1,2,2,6,6-pentamethyl-4-hydroxypiperidine, poly

[methylpropyl-3-oxo-4-(2,2,6,6-tetramethyl-4-piperidyl)] siloxane, reaction product of maleic anhydride-α-olefin copolymer and 2,2,6,6-tetramethyl-4-aminopiperidine or 1,2,2,6,6-pentamethyl-4-aminopiperidine, copolymers of (partially) N-piperidin-4-yl-substituted maleimide and a mixture of α-olefins such as Uvinul® 5050H (BASF AG), 1-(2-hydroxy-2-methylpropoxy)-4-octadecanoyloxy-2,2,6, 6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine and a carbon radical of t-amyl alcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4-yl)sebacate, bis(1-(2-hydroxy-2-methylpropoxy)-2,2,6,6-tetramethylpiperidin-4-yl)adipate, bis(1-(2-hydroxy-2-methylpropoxy)-2,2,6,6-tetramethylpiperidin-4-yl)succinate, bis(1-(2-hydroxy-2-methylpropoxy)-2,2,6,6-tetramethylpiperidin-4-yl) glutarate, 2,4-bis{N[1-(2-hydroxy-2-methylpropoxy)-2,2,6, 6-tetramethylpiperidin-4-yl]-N-butylamino}-6-(2-hydroxyethylamino)-s-triazine, N,N'-bisformyl-N,N'-bis(1, 2,2,6,6-pentamethyl-4-piperidyl)hexamethylenediamine, hexahydro-2,6-bis(2,2,6,6-tetramethyl-4-piperidyl)-1H,4H, 5H,8H-2,3a,4a,6,7a,8a-hexaazacyclopenta[def]fluorene-4, 8-dione (e.g. Uvinul® 4049 from BASF AG, Ludwigshafen), poly[[6-[(1,1,3,3-tetramethylbutyl)amino]-1,3,5-triazine-2, 4-diyl][(2,2,6,6-tetramethyl-4-piperidinyl)imino]-1,6-hexanediyl[(2,2,6,6-tetramethyl-4-piperidinyl)imino]]) [CAS No. 71878-19-8], 1,3,5-triazine-2,4,6-triamine, N,N'''-[1,2-ethanediylbis[[4,6-bis[butyl(1,2,2,6,6-pentamethyl-4-piperidinyl)amino]-1,3,5-triazin-2-yl]imino]-3,1-propanediyl]] bis[N',N''-dibutyl-N',N''-bis(1,2,2,6,6-pentamethyl-4-piperidinyl) (CAS No. 106990-43-6) (e.g., Chimassorb 119 from Ciba Specialty Chemicals, Inc.).

Group k) of the metal deactivators includes for example N,N'-diphenyloxalamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoylbisphenyl hydrazide, N,N'-diacetyladipic dihydrazide, N,N'-bis(salicyloyl)oxalic dihydrazide, and N,N'-bis(salicyloyl)thiopropionyl dihydrazide.

Group l) of the phosphites and phosphonites includes for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)pentaerythritol diphosphite, diisodecyloxy pentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl)4,4'-biphenylenediphosphonite, 6-isooctyloxy-2,4,8,10-tetra-tert-butyl-dibenzo[d,f][1,3,2]dioxaphosphepine, 6-fluoro-2,4,8,10-tetra-tert-butyl-12-methyl-dibenzo[d,g][1,3,2] dioxaphosphocine, bis(2,4-di-tert-butyl-6-methylphenyl) methyl phosphite, bis(2,4-di-tert-butyl-6-methylphenyl) ethyl phosphite, 2,2',2''-nitrilo[triethyl tris(3,3',5,5'-tetra-tert-butyl-1,1'-biphenyl-2,2'-diyl)phosphite], and 2-ethylhexyl 3,3',5,5'-tetra-tert-butyl-1,1'-biphenyl-2,2'-diyl phosphite.

Group m) of the hydroxylamines includes for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecyl-hydroxylamine, N-hexadecyl-N-octadecylhydroxylamine, N-heptadecyl-N-octa-decylhydroxylamine, N-methyl-N-octadecylhydroxylamine, and N,N-dialkylhydroxylamine from hydrogenated tallow fatty amines.

Group n) of the nitrones includes for example N-benzyl α-phenyl nitrone, N-ethyl α-methyl nitrone, N-octyl α-heptyl nitrone, N-lauryl α-undecyl nitrone, N-tetradecyl α-tridecyl nitrone, N-hexadecyl α-pentadecyl nitrone, N-octadecyl α-heptadecyl nitrone, N-hexadecyl α-heptadecyl nitrone, N-octadecyl α-pentadecyl nitrone, N-heptadecyl α-heptadecyl nitrone, N-octadecyl α-hexadecyl nitrone, N-methyl α-heptadecyl nitrone, and nitrones derived from N,N-dialkylhydroxylamines prepared from hydrogenated talc fatty amines.

Group o) of the amine oxides includes for example amine oxide derivatives as described in U.S. Pat. Nos. 5,844,029 and 5,880,191, didecylmethylamine oxide, tridecylamine oxide, tridodecylamine oxide and trihexadecylamine oxide.

Group p) of the benzofuranones and indolinones includes for example those described in U.S. Pat. Nos. 4,325,863; 4,338,244; 5,175,312; 5,216,052; 5,252,643; in DE-A-4316622; in DE-A-4316611; in DE-A-4316876; in EP-A-0589839 or EP-A-0591102, or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis [5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, Irganox® HP-136 from Ciba Specialty Chemicals, and 3-(2, 3-dimethylphenyl)-5,7-di-tert-butyl-benzofuran-2-one.

Group q) of the thiosynergists includes for example dilauryl thiodipropionate or distearyl thiodipropionate.

Group r) of the peroxide-destroying compounds includes for example esters of β-thiodipropionic acid, for example, the lauryl, stearyl, myristyl or tridecyl ester, mercaptobenzimidazole or the zinc salt of 2-mercaptobenzimidazole, zinc dibutyldithiocarbamate, dioctadecyl disulfide, and pentaerythritol tetrakis(β-dodecylmercapto)propionate.

Group s) of the basic costabilizers includes for example melamine, polyvinylpyrrolidone, dicyandiamide, triallylcyanurate, urea derivatives, hydrazine derivatives, amines, polyamides, polyurethanes, alkali metal and alkaline earth metal salts of higher fatty acids, for example, calcium stearate, zinc stearate, magnesium behenate, magnesium stearate, sodium ricinoleate, and potassium palmitate, antimony pyrocatecholate or zinc pyrocatecholate.

One preferred embodiment of the present invention uses at least one compound I together with at least one further light stabilizer having at least one absorption maximum in the wavelength range from 280 to 400 nm. The further light stabilizer is preferably selected from compounds of groups b), c), d), e), and g).

The light stabilizer in question in particular has at least one absorption maximum in the wavelength range from 280 to 320 nm. Accordingly, the light stabilizer employed additionally has at least one absorption maximum in the UVB range. Absorption maxima for the purposes of the present invention are the bands associated with the corresponding local or absolute maxima in the UV spectrum of the respective compounds, as measured in common organic solvents such as dichloromethane, acetonitrile or methanol at room temperature. The extinction of the UVB absorbers at the maximum, which is measured in solution, normally in dichloromethane, at a concentration of 1% by weight and a path length of 1 cm, is at least 100, in particular at least 200.

Examples of light stabilizers used additionally in particular are the aforementioned diphenylcyanoacrylates of group e).

In another preferred embodiment of the present invention at least one naphthalene-1,8-dicarboxylic monoimide I as defined above is used as sole light stabilizer from the group of the naphthalene derivatives having at least one absorption maximum in the wavelength range above 320 to 400 nm in order to protect organic material from the damaging effects of light. Typical representatives from the group of the naphthalene derivatives are the naphthalene-1,8-dicarboxylic monoimides I used in accordance with the invention and also naphthalenedicarboxylic acids, naphthalenedicarboxylic esters, naphthalenedicarboxylic anhydrides, naphthtalentetracarboxylic acids, naphthalenetetracarboxylic anhydrides, and naphthalentetracarbxylic esters.

In a further preferred embodiment of the present invention at least one naphthalene-1,8-dicarboxylic monoimide I as defined above is used as sole light stabilizer(s) to protect organic material from the damaging effects of light.

The plastic may further comprise other additives and auxiliaries. Suitable additives from the group t) are the customary additives, such as pigments, dyes, nucleating agents, fillers, reinforcing agents, antifogging agents, biocides, and antistats, for example.

Suitable pigments are inorganic pigments, examples being titanium dioxide in its three modifications—rutile, anatase or brookite; ultramarine blue, iron oxides, bismuth vanadates or carbon black, and also the class of the organic pigments, examples being compounds from the class of the phthalocyanines, perylenes, azo compounds, insoindolines, quinophthalones, diketopyrrolopyrroles, quinacridones, dioxazines, and indanthrones.

By dyes are meant all colorants which dissolve completely in the plastic used or are present in a molecularly disperse distribution and can therefore be used for the high-transparency, nonscattering coloring of polymers. Likewise regarded as dyes are organic compounds which exhibit a fluorescence in the visible part of the electromagnetic spectrum, such as fluorescent dyes.

Suitable nucleating agents include for example inorganic substances, examples being talc, metal oxides such as titanium dioxide or magnesium oxide, phosphates, carbonates or sulfates, preferably of alkaline earth metals; organic compounds such as monocarboxylic or polycarboxylic acids and also their salts, such as 4-tert-butylbenzoic acid, adipic acid, diphenylacetic acid, sodium succinate or sodium benzoate; and polymeric compounds, such as ionic copolymers ("ionomers"), for example.

Suitable fillers and reinforcing agents include for example calcium carbonate, silicates, talc, mica, kaolin, barium sulfate, metal oxides and metal hydroxides, carbon black, graphite, wood flour and flours or fibers of other natural products, and synthetic fibers. Further suitable examples of fibrous or pulverulent fillers include carbon or glass fibers in the form of glass fabrics, glass mats or filament glass rovings, chopped glass, glass beads, and wollastonite. Glass fibers can be incorporated either in the form of short glass fibers or in the form of continuous fibers (rovings).

Examples of suitable antistats include amine derivatives such as N,N-bis(hydroxy-alkyl)alkylamines or -alkylenamines, polyethylene glycol esters and ethers, ethoxylated carboxylic esters and carboxamides, and glyceryl mono- and distearates, and also mixtures thereof.

Normally the plastic is admixed with at least one naphthalene-1,8-dicarboxylic monoimide I in an amount of from 0.01 to 10% by weight, preferably from 0.01 to 5% by weight, and more preferably from 0.01 to 1.0% by weight, based on the total weight of the plastic. By the total weight of the plastic is meant the weight of the plastic addititized with the naphthalene-1,8-dicarboxylic monoimide I and, where appropriate, with further (co)stabilizers (plastic+sum of all (co)stabilizers+sum of all other additives). The light protection achieved is dependent on the path length in the plastic. This is illustrated by the Lambert-Beer law $E=\epsilon \cdot c \cdot d$ ($\epsilon$: molar extinction (absorbance) coefficient, c: concentration, d: path length). In thin layers of plastic, therefore, it is usual to use a higher proportion of UV absorber than in a thick layer of plastic.

The compounds from groups a) to s) are used, with the exception of the benzofuranones of group p), in customary amounts: for example, in amounts of from 0.0001 to 10% by weight, preferably from 0.01 to 1% by weight, based on the total weight of the plastic.

The additives of group t) are used in the customary amounts. They are normally used in an amount of from 0 to 60% by weight, based on the total weight of the plastic.

The naphthalene-1,8-dicarboxylic monoimide I used in accordance with the invention can also be added in the form of a premix (masterbatch or compound) containing at least one naphthalene-1,8-dicarboxylic monoimide I in a concentration of from 1 to 20% by weight to the materials that are to be stabilized, usually a plastic. The premix may further comprise the aforementioned compounds of groups a) to s) and other additives of group t).

The present invention additionally provides compositions comprising at least one naphthalene-1,8-dicarboxylic monoimide of the formula I as defined above in an amount providing protection from the damaging effects of light, and at least one organic material. The organic material is preferably a polymer selected from polyesters, polycarbonate polymers, polyolefins, polyvinyl acetals, polystyrene, copolymers of styrene or of α-methylstyrene with dienes and/or acrylic derivatives, and physical blends of the aforementioned polymers.

The text below relating to the compositions of the invention concerning suitable and preferred embodiments applies equally to the corresponding use of such a naphthalene-1,8-dicarboxylic monoimide in a thermoplastic molding compound of this kind.

A preferred embodiment of the present invention relates to a composition comprising:
  at least one naphthalene-1,8-dicarboxylic monoimide of the formula I as defined above;
  at least one polyvinyl butyral (PVB);
  at least one oligoalkylene glycol alkylcarboxylic diester as plasticizers;
  at least one aliphatic carboxylic salt to control the adhesion;
  if desired, at least one further UV absorber selected from benzotriazoles, 2-phenyl-1,3,5-triazines, hydroxybenzophenones, diphenylcyanoacrylates, and mixtures thereof, and
  if desired, at least one further components selected from fillers, dyes, pigments, and additional additives.

Particular preference is given to employing at least one naphthalene-1,8-dicarboxylic monoimide of the formula I in PVB sheets in laminated glass, for automotive glazing systems for example. With very particular preference the naphthalene-1,8-dicarboxylic monoimide of the formula I is selected from the naphthalene-1,8-dicarboxylic monoimides I-C.

With regard to the preparation of polyvinyl butyral, the text above is incorporated in its entirety by reference. The polyvinyl butyrals used in the polymer composition generally have an average molecular mass of more than 70 000, preferably from about 100 000 to 250 000. The polyvinyl butyral normally has a residual hydroxyl group content of less than 19.5%, preferably from about 17 to 19% by weight, calculated as polyvinyl alcohol, and a residual ester group content of from 0 to 10%, preferably from 0 to 3%, calculated as polyvinyl ester. An advantageous polyvinyl butyral is that obtainable under the name Butvar® from Solutia, Inc. of St. Louis, Mo. The polyvinyl butyral molding compound is normally used in the form of a sheet with a thickness of from 0.13 to 1.5 mm. The polyvinyl butyral can be shaped to the desired thickness on a sheet extrusion line, for example.

Suitable oligoalkylene glycol carboxylic diesters comprise the esters of aliphatic, unbranched or branched $C_2$-$C_{10}$ monocarboxylic acids, preferably $C_6$-$C_8$ monocarboxylic acids, with tri-$C_2$-$C_3$ alkylene glycols or tetra-$C_2$-$C_3$ alkylene glycols. Suitable plasticizers are, for example, triethylene glycol di(2-ethylbutyrate), triethylene glycol di(2-ethylhexanoate), triethylene glycol diheptanoate or tetraethylene glycol diheptanoate. The fraction of plasticizer is generally from 20 to 80% by weight, preferably from 25 to 45% by weight, based on the total weight of the polymer composition.

Suitable aliphatic carboxylic salts to control adhesion are, for example, the polyvalent metal salts of branched or unbranched $C_4$-$C_{22}$ monocarboxylic acids. Suitable metals include, for example, zinc, aluminum, lead or alkaline earth metals such as magnesium or calcium. A suitable example of an aliphatic carboxylic salt to control adhesion is, for example, the magnesium salt of 2-ethylbutyric acid. The salts lower the tack and viscosity of the polyvinyl butyral. The fraction of aliphatic carboxylic salt is generally from 0.0001 to 0.5% by weight, preferably from 0.0001 to 0.1% by weight, based on the total weight of the polymer composition.

The polyvinyl butyral polymer composition may further comprise at least one additional UV absorber, preferably selected from benzotriazoles, 2-phenyl-1,3,5-triazines, hydroxybenzophenones, diphenylcyanoacrylates, and mixtures thereof.

Examples of suitable benzotriazoles are 2-(2'-hydroxyphenyl)benzotriazoles, preferably those mentioned above. Particular preference is given to the following:

2-(3'-tert-butyl-2'-hydroxy-5'-methylphenyl)-5-chlorobenzotriazole [CAS No. 3896-11-5), available commerically for example as Tinuvin® 326 from Ciba Specialty Chemicals, Inc.;

2,4-di-tert-butyl-6-(5-chlorobenzotriazol-2-yl)phenol [CAS No. 3864-99-1], available commercially for example as Tinuvin® 327 from Ciba Specialty Chemicals, Inc.;

2-(2H-benzotriazol-2-yl)-4,6-di-tert-pentylphenol [CAS No. 25973-55-1], available commercially for example as Tinuvin® 328 from Ciba Specialty Chemicals, Inc.; and 2-benzotriazol-2-yl-4-methylphenol [CAS No. 2440-22-4], available commercially for example as Tinuvin® P from Ciba Specialty Chemicals, Inc.

Examples of suitable 2-phenyl-1,3,5-triazines are 2-(2'-hydroxyphenyl)-1,3,5-triazines, preferably those mentioned above. Particular preference is given to the following:

2-(4,6-diphenyl-1,3,5-triazin-2-yl)-5-hexyloxyphenol [CAS 147315-50-2], available commercially for example as Tinuvin® 1577 from Ciba Specialty Chemicals, Inc.; and 2,4-bis(2,4-dimethylphenyl)-6-(2-hydroxy-4-octyloxyphenyl)-1,3,5-triazine [CAS No. 2725-22-6], available commercially for example as Cyasorb® UV 1164 from Cytec.

Examples of suitable hydroxybenzophenones are 2-hydroxybenzophenones, preferably those mentioned above. Particular preference is given to the following:

2-hydroxy-4-n-octoxybenzophenone [CAS No. 1843-05-6], available commercially for example as Chimassorb® 81 from Ciba Specialty Chemicals, Inc.

Examples of suitable diphenylcyanoacrylates are those mentioned above. Particular preference is given to the following:

1,3-bis[(2'-cyano-3',3'-diphenylacryloyl)oxy]-2,2-bis{[2'-cyano-3',3'-diphenyl-acryloyl)oxy]methyl}propane [CAS No. 178671-584], available commercially for example under the name Uvinul® 3030 from BASF AG, Ludwigshafen;

ethyl 2-cyano-3,3-diphenylacrylate [CAS No. 5232-99-5], available commercially for example under the name Uvinul® 3035 from BASF AG, Ludwigshafen; and 2-ethylhexyl 2-cyano-3,3-diphenylcyanoacrylate [CAS 6197-304], available commercially for example under the name Uvinul® 3039 from BASF AG, Ludwigshafen.

Generally speaking, the fraction of further UV absorber, dependent on the thickness of the sheet used, is from 0.05 to 2% by weight, preferably from 0.1 to 1% by weight, based on the total weight of the polymer composition. In the case of thin polymer layers the fraction of UV absorber used is generally higher than in the case of thick polymer layers.

The polyvinyl butyral polymer composition may further comprise at least one additional component selected from fillers, dyes, pigments, and further additives. As regards suitable fillers, dyes, and pigments, the text above is incorporated in its entirety by reference.

Another preferred embodiment of the present invention relates to a composition comprising at least one naphthalene-1,8-dicarboxylic monoimide of the formula I as defined above;

at least one polycarbonate polymer selected from polycarbonates, polycarbonate copolymers, and physical blends of polycarbonates with acrylonitrile-butadiene-styrene copolymers, acrylonitrile-styrene-acrylate copolymers, polymethyl methacrylates, polybutyl acrylates, polybutyl methacrylates, poly(butylene terephthalate)s, and polyethylene terephthalates;

at least one stabilizer selected from phosphites, phosphonites, and mixtures thereof;

if desired, at least one further UV absorber selected from benzotriazoles, 2-phenyl-1,3,5-triazines, diphenylcyanoacrylates, and mixtures thereof;

if desired, at least one 2,6-dialkylated phenol antioxidant, and if desired, at least one further component selected from fillers, dyes, pigments, and other additives.

Likewise preferred is the use of at least one naphthalene-1,8-dicarboxylic monoimide of the formula I as defined above in a polycarbonate polymer composition.

For the purposes of the present invention the term "polycarbonate copolymers" embraces polycarbonates obtainable by condensing phosgene or carbonic esters with at least two different dihydroxy compounds: different bisphenols, for example. A fraction of halogenated bisphenols, tetrabromobisphenol for example, raises the flame retardancy; a fraction of bisphenol S (dihydroxydiphenyl sulfide) raises the notched impact strength. The polycarbonate copolymers include for example polycarbonate copolymers based on bisphenol A and bisphenol C, or polycarbonate copolymers based on bisphenol A and bisphenol TMC (trimethylcyclohexane). For the purposes of the present invention the term "polycarbonate copolymers" also includes polyester carbonates, which are obtainable for example by reacting bisphenols with phosgene and aromatic dicarbonyl dichlorides, and block copolymers comprising polycarbonate blocks and polyalkylene oxide blocks.

The polycarbonate polymer composition comprises at least one stabilizer selected from phosphites and phosphonites. As regards suitable phosphites and phosphonites, the remarks above are incorporated in their entirety by reference. Preferred phosphites and phosphonites are tris(2,4-di-tert-butylphenyl)phosphite [CAS No. 31570-04-4], which is available commercially for example as Irgafos® 168 from Ciba Specialty Chemicals, Inc., tetrakis(2,4-di-tert-butylphenyl)-4,4'-diyl bisphosphonite [CAS No. 119345-01-6], obtainable commercially for example as Irgafos® P-EPQ from Ciba Specialty Chemicals, Inc., and mixtures thereof. The fraction of phosphite and/or phosphonite is generally up to 2000 ppm, preferably from 500 to 1500 ppm, based on the total weight of the polymer composition.

The polycarbonate polymer composition may further comprise at least one other UV absorber. Suitable other UV absorbers are those mentioned above. The other UV absorbers are preferably selected from benzotriazoles, 2-phenyl-1,3,5-triazines, diphenylcyanoacrylates, and mixtures thereof.

Examples of suitable benzotriazoles are 2-(2'-hydroxyphenyl)benzotriazoles, preferably those mentioned above. Particular preference is given to the following:

2-(2H-benzotriazol-2-yl)-4,6-bis(1-methyl-1-phenylethyl)phenol [CAS No. 70321-86-7], available commercially for example as Tinuvin® 234 from Ciba Specialty Chemicals, Inc.;

2,4-di-tert-butyl-6-(5-chlorobenzotriazol-2-yl)phenol [CAS No. 3864-99-1], available commercially for example as Tinuvin® 327 from Ciba Specialty Chemicals, Inc.;

2-(2H-benzotriazol-2-yl)-4-(1,1,3,3-tetramethylbutyl) phenol [CAS No. 3147-75-9], available commercially for example as Tinuvin® 329 from Ciba Specialty Chemicals, Inc.;

2-(2H-benzotriazol-2-yl)-4-(tert-butyl)-6-(sec-butyl)phenol [CAS No. 36437-37-3], available commercially for example as Tinuvin® 350 from Ciba Specialty Chemicals, Inc.;

2,2'-methylenebis-(6-(2H-benzotriazol-2-yl)-4-1,1,3,3-tetramethylbutyl)phenol) [CAS No. 103597-45-1], available commercially for example as Tinuvin® 360 from Ciba Specialty Chemicals, Inc.; and transesterification products of methyl 3-(3-(2H-benzotriazol-2-yl)-5-tert-butyl-4-hydroxyphenyl)propionate with polyethylene glycol, obtainable for example as Tinuvin® 213 from Ciba Specialty Chemicals, Inc., (containing 52% of the compound R—COO—[(CH$_2$)$_2$—O]$_n$—H (molar mass: 637 g/mol) [CAS No. 104810-48-2], 35% of the compound of the formula R—COO—[(CH$_2$)$_2$—O]$_n$—CO—R (molar mass: 975 g/mol) [CAS No. 104810-47-1] with

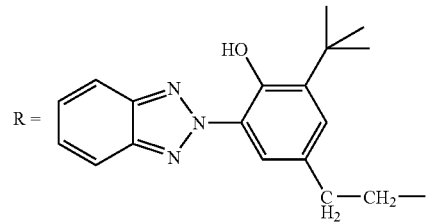

and 13% of the compound HO—[(CH$_2$)$_2$—O]$_n$—H [CAS No. 25322-68-3].

Examples of 2-phenyl-1,3,5-triazines are 2-(2'-hydroxyphenyl)-1,3,5-triazines, preferably those mentioned above. Particular preference is given to the following:

2-(4,6-diphenyl-1,3,5-triazin-2-yl)-5-hexyloxyphenol [CAS No. 147315-50-2], available commercially for example as Tinuvin® 1577 from Ciba Specialty Chemicals, Inc.

Examples of suitable diphenylcyanoacrylates are those mentioned above. Preference is given to the following:

1,3-bis[(2'-cyano-3',3'-diphenylacryloyl)oxy]-2,2-bis{[2'-cyano-3',3'-diphenyl-acryloyl)oxy]methyl}propane [CAS No. 178671-58-4], available commercially for example under the name Uvinul® 3030 from BASF AG, Ludwigshafen; and ethyl-2-cyano-3,3-diphenylacrylate [CAS No. 5232-99-5], available commercially for example under the name Uvinul® 3035 from BASF AG, Ludwigshafen.

In general the fraction of other UV absorbers is up to 10% by weight, preferably 0.001-10% by weight, in particular 0.05-10% by weight, very preferably 0.1-10% by weight, based on the total weight of the polymer composition. In the case of thin polymer layers the fraction of UV absorber used is generally higher than in the case of thick polymer layers.

The polycarbonate polymer composition may further comprise at least a 2,6-dialkylated phenol antioxidant. Suitable 2,6-dialkylated phenols are those mentioned above and, in particular, the esters of β-(3,5-di-tert-butyl-4-hydroxyphenyl)propionic acid with monohydric or polyhydric alcohols. Preferred esters of β-(3,5-di-tert-butyl-4-hydroxyphenyl) propionic acid with monohydric or polyhydric alcohols are pentaerythritol tetrakis[3-(3,5-di-tert-butyl-4-hydroxyphenyl)propionate] [CAS No. 6683-19-8], available commercially for example as Irganox® 1010 from Ciba Specialty Chemicals, Inc., octadecyl 3-(3,5-di-tert-butyl-4-hydroxyphenyl)propionate [CAS No. 2082-79-3], available commercially for example as Irganox® 1076 from Ciba Specialty Chemicals, Inc., and mixtures thereof. The fraction of antioxidant is generally up to 2000 ppm, preferably from 500 to 2000 ppm, based on the total weight of the polymer composition.

In a further preferred embodiment the polymer composition comprises not only at least one 2,6-dialkylated phenol antioxidant but also at least one phosphite and/or phosphonite stabilizer. The ratio of antioxidant to costabilizer is in that case generally in the range from 1:10 to 10:1.

One especially preferred embodiment of the present invention relates to a polymer composition which comprises at least one polycarbonate, at least one naphthalene-1,8-dicarboxylic monoimide of the formula I as defined above, and, as (a further component(s), the substance(s) indicated in a line of Table A (compositions 1.1 to 1.60). The naphthalene-1,8-dicarboxylic monoimide of the formula I is preferably selected from naphthalene-1,8-dicarboxylic monoimides of the formula I-C. The weight fractions of the individual constituents in the compositions 1.1 to 1.60 are situated within the ranges indicated above, based on the total weight of the polymer composition.

TABLE A

| Composition | Stabilizer CAS number | UV absorber CAS number | Antioxidant CAS number |
|---|---|---|---|
| 1.1 | 31570-04-4 | | |
| 1.2 | 31570-04-4 | Tinuvin ® 213 | |
| 1.3 | 31570-04-4 | 70321-86-7 | |
| 1.4 | 31570-04-4 | 3864-99-1 | |
| 1.5 | 31570-04-4 | 3147-75-9 | |
| 1.6 | 31570-04-4 | 36437-37-3 | |
| 1.7 | 31570-04-4 | 103597-45-1 | |
| 1.8 | 31570-04-4 | 147315-50-2 | |
| 1.9 | 31570-04-4 | 178671-58-4 | |
| 1.10 | 31570-04-4 | 5232-99-5 | |
| 1.11 | 31570-04-4 | | 6683-19-8 |
| 1.12 | 31570-04-4 | | 2082-79-3 |
| 1.13 | 31570-04-4 | Tinuvin ® 213 | 6683-19-8 |
| 1.14 | 31570-04-4 | 70321-86-7 | 6683-19-8 |
| 1.15 | 31570-04-4 | 3864-99-1 | 6683-19-8 |
| 1.16 | 31570-04-4 | 3147-75-9 | 6683-19-8 |
| 1.17 | 31570-04-4 | 36437-37-3 | 6683-19-8 |
| 1.18 | 31570-04-4 | 103597-45-1 | 6683-19-8 |
| 1.19 | 31570-04-4 | 147315-50-2 | 6683-19-8 |
| 1.20 | 31570-04-4 | 178671-58-4 | 6683-19-8 |
| 1.21 | 31570-04-4 | 5232-99-5 | 6683-19-8 |
| 1.22 | 31570-04-4 | Tinuvin ® 213 | 2082-79-3 |
| 1.23 | 31570-04-4 | 70321-86-7 | 2082-79-3 |
| 1.24 | 31570-04-4 | 3864-99-1 | 2082-79-3 |
| 1.25 | 31570-04-4 | 3147-75-9 | 2082-79-3 |
| 1.26 | 31570-04-4 | 36437-37-3 | 2082-79-3 |
| 1.27 | 31570-04-4 | 103597-45-1 | 2082-79-3 |
| 1.28 | 31570-04-4 | 147315-50-2 | 2082-79-3 |
| 1.29 | 31570-04-4 | 178671-58-4 | 2082-79-3 |
| 1.30 | 31570-04-4 | 5232-99-5 | 2082-79-3 |
| 1.31 | 119345-01-6 | | |
| 1.32 | 119345-01-6 | Tinuvin ® 213 | |
| 1.33 | 119345-01-6 | 70321-86-7 | |
| 1.34 | 119345-01-6 | 3864-99-1 | |
| 1.35 | 119345-01-6 | 3147-75-9 | |
| 1.36 | 119345-01-6 | 36437-37-3 | |
| 1.37 | 119345-01-6 | 103597-45-1 | |
| 1.38 | 119345-01-6 | 147315-50-2 | |
| 1.39 | 119345-01-6 | 178671-58-4 | |
| 1.40 | 119345-01-6 | 5232-99-5 | |
| 1.41 | 119345-01-6 | | 6683-19-8 |
| 1.42 | 119345-01-6 | | 2082-79-3 |
| 1.43 | 119345-01-6 | Tinuvin ® 213 | 6683-19-8 |
| 1.44 | 119345-01-6 | 70321-86-7 | 6683-19-8 |
| 1.45 | 119345-01-6 | 3864-99-1 | 6683-19-8 |
| 1.46 | 119345-01-6 | 3147-75-9 | 6683-19-8 |
| 1.47 | 119345-01-6 | 36437-37-3 | 6683-1 9-8 |
| 1.48 | 119345-01-6 | 103597-45-1 | 6683-19-8 |
| 1.49 | 119345-01-6 | 147315-50-2 | 6683-19-8 |
| 1.50 | 119345-01-6 | 178671-58-4 | 6683-19-8 |
| 1.51 | 119345-01-6 | 5232-99-5 | 6683-19-8 |
| 1.52 | 119345-01-6 | Tinuvin ® 213 | 2082-79-3 |
| 1.53 | 119345-01-6 | 70321-86-7 | 2082-79-3 |
| 1.54 | 119345-01-6 | 3864-99-1 | 2082-79-3 |
| 1.55 | 119345-01-6 | 3147-75-9 | 2082-79-3 |
| 1.56 | 119345-01-6 | 36437-37-3 | 2082-79-3 |
| 1.57 | 119345-01-6 | 103597-45-1 | 2082-79-3 |
| 1.58 | 119345-01-6 | 147315-50-2 | 2082-79-3 |
| 1.59 | 119345-01-6 | 178671-58-4 | 2082-79-3 |
| 1.60 | 119345-01-6 | 5232-99-5 | 2082-79-3 |

A further especially preferred embodiment of the present invention relates to a polymer composition 2.1 to 2.60, which differ from the corresponding compositions 1.1 to 1.60 only in that the polycarbonate is replaced by a polycarbonate copolymer.

A further especially preferred embodiment of the present invention relates to a polymer composition 3.1 to 3.60, which differ from the corresponding compositions 1.1 to 1.60 only in that the polycarbonate is replaced by a physical blend of polycarbonates with acrylonitrile-butadiene-styrene-copolymers.

A further especially preferred embodiment of the present invention relates to a polymer composition 4.1 to 4.60, which differ from the corresponding compositions 1.1 to 1.60 only in that the polycarbonate is replaced by a physical blend of polycarbonates with acrylonitrile-styrene-acrylate copolymers.

A further especially preferred embodiment of the present invention relates to a polymer composition 5.1 to 5.60, which differ from the corresponding compositions 1.1 to 1.60 only in that the polycarbonate is replaced by a physical blend of polycarbonates with polymethyl methacrylates.

A further especially preferred embodiment of the present invention relates to a polymer composition 6.1 to 6.60, which differ from the corresponding compositions 1.1 to 1.60 only in that the polycarbonate is replaced by a physical blend of polycarbonates with polybutyl acrylates.

A further especially preferred embodiment of the present invention relates to a polymer composition 7.1 to 7.60, which differ from the corresponding compositions 1.1 to 1.60 only in that the polycarbonate is replaced by a physical blend of polycarbonates with polybutyl methyacrylates.

A further especially preferred embodiment of the present invention relates to a polymer composition 8.1 to 8.60, which differ from the corresponding compositions 1.1 to 1.60 only in that the polycarbonate is replaced by a physical blend of polycarbonates with poly(butylene terephthalate)s.

A further especially preferred embodiment of the present invention relates to the use of at least one naphthalene-1,8-dicarboxylic monoimide of the formula I as defined above in a polymer composition 9.1 to 9.60, which differ from the corresponding compositions 1.1 to 1.60 only in that the polycarbonate is replaced by a physical blend of polycarbonates with polyethylene terephthalates.

The polycarbonate polymer composition can further comprise at least one additional component selected from dyes, pigments, and other additives.

Regarding suitable dyes and pigments, the remarks above are incorporated here in their entirety by reference. In one preferred embodiment the dye and/or the pigment is a bluing agent. Suitable bluing agents are, for example, ultramarine blue, phthalocyanines, anthraquinones, and indanthrones. When a bluing agent is used as well the fraction of bluing agent is up to 500 ppm (0.05% by weight), preferably 0.5-100 ppm, based on the total weight of the polymer composition.

Preferred applications for polycarbonate polymer compositions of the invention are as lenses for headlamp covers, as windshields in automobiles, and as other lens/glazing systems in automobiles and architecture.

A further preferred embodiment of the present invention relates to a composition comprising
   at least one naphthalene-1,8-dicarboxylic monoimide as defined above;
   at least one polyethylene terephthalate (PET);
   at least one 2,6-dialkylated phenol antioxidant;
   if desired, at least one costabilizer selected from phosphites, phosphonites, and mixtures thereof; and
   if desired, at least one further UV absorber selected from diphenylcyanoacrylates, phenyl-1,3,5-triazines, and benzotriazoles, and mixtures thereof.

Likewise preferred is the use of at least one naphthalene-1,8-dicarboxylic monoimide of the formula I as defined above in a PET composition. The naphthalene-1,8-dicarboxylic monoimide of the formula I is preferably selected from the naphthalene-1,8-dicarboxylic monoimides I-C.

Suitable 2,6-dialkylated phenol antioxidants are those mentioned above. Preference is given to the esters of β-(3,5-di-tert-butyl-4-hydroxyphenyl)propionic acid with monohydric or polyhydric alcohols and particularly pentaerythritol tetrakis[3-(3,5-di-tert-butyl-4-hydroxyphenyl)propionate] [CAS No. 6683-19-8], available commercially for example as Irganox® 1010 from Ciba Specialty Chemicals, Inc., hexamethylene-bis-(3-(3,5-di-tert-butyl-4-hydroxyphenyl)propionate [CAS No. 35074-77-2], available commercially for example as Irganox® 259 from Ciba Specialty Chemicals, Inc., and 3,5-dialkylated hydroxyphenylmethylphosphonic esters, preferably diethyl ((3,5-bis(1,1-dimethylethyl)-4-hydroxyphenyl)methyl)phosphonate [CAS No. 976-56-7], available commercially for example as Irganox® 1222 from Ciba Specialty Chemicals, Inc.

The fraction of antioxidant is generally up to 2000 ppm, preferably from 500 to 2000 ppm, based on the total weight of the polymer composition.

If desired, the polyethylene terephthalate polymer composition comprises at least one costabilizer selected from phosphites, phosphonites, and mixtures thereof. Suitable phosphites and phosphonites are those mentioned above. One preferred phosphite is tris(2,4-di-tert-butylphenyl)phosphite [CAS No. 31570-04-4], available commercially for example as Irgafos® 168 from Ciba Specialty Chemicals, Inc. The fraction of phosphite and/or phosphonite is generally up to 2000 ppm, preferably from 500 to 2000 ppm, in particular from 750 to 2000 ppm, based on the total weight of the polymer composition.

In a further preferred embodiment the polyethylene terephthalate polymer composition comprises not only at least one 2,6-dialkylated phenol, preferably at least one 3,5-dialkylated hydroxyphenylmethylphosphonic ester and/or at least one ester of β-(3,5-di-tert-butyl-4-hydroxyphenyl)propionic acid with monohydric or polyhydric alcohols, as antioxidant, but also at least one phosphite and/or phosphonite as costabilizer. The ratio of antioxidant to costabilizer is in that case in general in the range from 1:10 to 10:1.

The polyethylene terephthalate polymer composition may further comprise at least one other UV absorber. Suitable other UV absorbers are those mentioned above. The other UV absorbers are preferably selected from benzotriazoles, phenyl-1,3,5-triazines, diphenylcyanoacrylates, and mixtures thereof.

Examples of suitable benzotriazoles are 2-(2'-hydroxyphenyl)benzotriazoles, preferably those mentioned above. Particular preference is given to the following:

2-(2H-benzotriazol-2-yl)-4,6-bis(1-methyl-1-phenyl-ethyl)phenol [CAS No. 70321-86-7], available commercially for example as Tinuvin® 234 from Ciba Specialty Chemicals, Inc.;

2,4-di-tert-butyl-6-(5-chlorobenzotriazol-2-yl)phenol [CAS No. 3864-99-1], available commercially for example as Tinuvin® 327 from Ciba Specialty Chemicals, Inc.;

2,2'-methylenebis-(6-(2H-benzotriazol-2-yl)-4-1,1,3,3-tetramethylbutyl)phenol [CAS No. 103597-45-1], available commercially for example as Tinuvin® 360 from Ciba Specialty Chemicals, Inc.; and transesterification products of methyl 3-(3-(2H-benzotriazol-2-yl)-5-tert-butyl-4-hydroxyphenyl)propionate with polyethylene glycol, obtainable for example as Tinuvin® 213 from Ciba Specialty Chemicals, Inc.

Examples of suitable 2-phenyl-1,3,5-triazines are 2-(2'-hydroxyphenyl)-1,3,5-triazines, preferably those mentioned above. Particular preference is given to the following:

2-(4,6-diphenyl-1,3,5-triazin-2-yl)-5-hexyloxyphenol [CAS No. 147315-50-2], available commercially for example as Tinuvin® 1577 from Ciba Specialty Chemicals, Inc.

Examples of suitable diphenylcyanoacrylates are those mentioned above. Preference is given to the following:

1,3-bis[(2'-cyano-3',3'-diphenylacryloyl)oxy]-2,2-bis{[2'-cyano-3',3'-diphenyl-acryloyl)oxy]methyl}propane [CAS No. 178671-58-4], available commercially for example under the name Uvinul® 3030 from BASF AG, Ludwigshafen;

ethyl 2-cyano-3,3-diphenylacrylate [CAS No. 5232-99-5], available commercially for example under the name Uvinul® 3035 from BASF AG, Ludwigshafen; and 2-ethylhexyl 2-cyano-3,3-diphenylacrylate [CAS No. 6197-30-4], obtainable commercially for example under the name Uvinul® 3039 from BASF AG, Ludwigshafen.

In general the fraction of other UV absorbers is up to 2% by weight, preferably 0.01-5% by weight, in particular 0.1-0.15% by weight, based on the total weight of the polyethylene terephthalate polymer composition. In the case of thin polymer layers the fraction of UV absorber used is generally higher than in the case of thick polymer layers.

One especially preferred embodiment of the present invention relates to polyethylene terephthalate polymer compositions which comprise at least one naphthalene-1,8-dicarboxylic monoimide of the formula I as defined above, and, as (a) further component(s), the substance(s) indicated in a line of Table B (compositions 10.1 to 10.54). The naphthalene-1,8-dicarboxylic monoimide of the formula I is preferably selected from naphthalene-1,8-dicarboxylic monoimides of the formula I-C. The weight fractions of the individual constituents in the compositions 10.1 to 10.54 are situated within the ranges indicated above, based on the total weight of the polymer composition.

TABLE B

| Composition | Antioxidant CAS number | Costabilizer CAS number | UV Absorber CAS number |
|---|---|---|---|
| 10.1 | 6683-19-8 | | |
| 10.2 | 6683-19-8 | 31570-04-4 | |
| 10.3 | 6683-19-8 | | Tinuvin ® 213 |
| 10.4 | 6683-19-8 | | 70321-86-7 |
| 10.5 | 6683-19-8 | | 3864-99-1 |
| 10.6 | 6683-19-8 | | 103597-45-1 |
| 10.7 | 6683-19-8 | | 147315-50-2 |
| 10.8 | 6683-19-8 | | 178671-58-4 |
| 10.9 | 6683-19-8 | | 5232-99-5 |
| 10.10 | 6683-19-8 | | 6197-30-4 |
| 10.11 | 6683-19-8 | 31570-04-4 | Tinuvin ® 213 |
| 10.12 | 6683-19-8 | 31570-04-4 | 70321-86-7 |
| 10.13 | 6683-19-8 | 31570-04-4 | 3864-99-1 |
| 10.14 | 6683-19-8 | 31570-04-4 | 103597-45-1 |
| 10.15 | 6683-19-8 | 31570-04-4 | 147315-50-2 |
| 10.16 | 6683-19-8 | 31570-04-4 | 178671-58-4 |
| 10.17 | 6683-19-8 | 31570-04-4 | 5232-99-5 |
| 10.18 | 6683-19-8 | 31570-04-4 | 6197-30-4 |
| 10.19 | 35074-77-2 | | |
| 10.20 | 35074-77-2 | 31570-04-4 | |
| 10.21 | 35074-77-2 | | Tinuvin ® 213 |
| 10.22 | 35074-77-2 | | 70321-86-7 |
| 10.23 | 35074-77-2 | | 3864-99-1 |
| 10.24 | 35074-77-2 | | 103597-45-1 |
| 10.25 | 35074-77-2 | | 147315-50-2 |
| 10.26 | 35074-77-2 | | 178671-58-4 |
| 10.27 | 35074-77-2 | | 5232-99-5 |
| 10.28 | 35074-77-2 | | 6197-30-4 |
| 10.29 | 35074-77-2 | 31570-04-4 | Tinuvin ® 213 |
| 10.30 | 35074-77-2 | 31570-04-4 | 70321-86-7 |
| 10.31 | 35074-77-2 | 31570-04-4 | 3864-99-1 |
| 10.32 | 35074-77-2 | 31570-04-4 | 103597-45-1 |

TABLE B-continued

| Composition | Antioxidant CAS number | Costabilizer CAS number | UV Absorber CAS number |
|---|---|---|---|
| 10.33 | 35074-77-2 | 31570-04-4 | 147315-50-2 |
| 10.34 | 35074-77-2 | 31570-04-4 | 178671-58-4 |
| 10.35 | 35074-77-2 | 31570-04-4 | 5232-99-5 |
| 10.36 | 35074-77-2 | 31570-04-4 | 6197-30-4 |
| 10.37 | 976-56-7 | | |
| 10.38 | 976-56-7 | 31570-04-4 | |
| 10.39 | 976-56-7 | | Tinuvin ® 213 |
| 10.40 | 976-56-7 | | 70321-86-7 |
| 10.41 | 976-56-7 | | 3864-99-1 |
| 10.42 | 976-56-7 | | 103597-45-1 |
| 10.43 | 976-56-7 | | 147315-50-2 |
| 10.44 | 976-56-7 | | 178671-58-4 |
| 10.45 | 976-56-7 | | 5232-99-5 |
| 10.46 | 976-56-7 | | 6197-30-4 |
| 10.47 | 976-56-7 | 31570-04-4 | Tinuvin ® 213 |
| 10.48 | 976-56-7 | 31570-04-4 | 70321-86-7 |
| 10.49 | 976-56-7 | 31570-04-4 | 3864-99-1 |
| 10.50 | 976-56-7 | 31570-04-4 | 103597-45-1 |
| 10.51 | 976-56-7 | 31570-04-4 | 147315-50-2 |
| 10.52 | 976-56-7 | 31570-04-4 | 178671-58-4 |
| 10.53 | 976-56-7 | 31570-04-4 | 5232-99-5 |
| 10.54 | 976-56-7 | 31570-04-4 | 6197-30-4 |

In a further preferred embodiment of the present invention the polyethylene terephthalate is an amorphous polyethene terephthalate and the polyethylene terephthalate polymer composition further comprises at least one acetaldehyde scavenger. An example of a suitable acetaldehyde scavenger is anthranilamide [CAS No. 88-68-6].

A further particularly preferred embodiment of the present invention relates to polyethylene terephthalate polymer compositions 11.1 to 11.54, which differ from the corresponding compositions 10.1 to 10.54 only in that the polyethylene terephthalate is an amorphous polyethylene terephthalate and the composition additionally includes an acetaldehyde scavenger. In particular the naphthalene-1,8-dicarboxylic monoimide of the formula I is a naphthalene-1,8-dicarboxylic monoimide of the formula I-C.

The polymer composition comprising the amorphous polyethylene terephthalate may additionally include at least one further component, selected from reheating agents, dyes, pigments, and other additives.

For the purposes of the present invention a reheating agent is a substance which by absorbing energy accelerates the plasticization of the polymer and so allows the polymer mass to be shaped by downstream assemblies (a bottle blowing mold, for example). Carbon black is an example of a suitable reheating agent. Carbon black can be used in the form of powder or granules. The fraction of reheating agent is generally from 0.1 to 2% by weight, based on the total weight of the polymer composition. Suitable dyes, pigments, and other additives are those mentioned above.

Particular preference is given to the use of at least one naphthalene-1,8-dicarboxylic monoimide of the formula I in compositions comprising an amorphous polyethylene terephthalate, at least one 2,6-dialkylated phenol antioxidant, and at least one acetaldehyde scavenger for packing materials such as bottles or containers. The naphthalene-1,8-dicarboxylic monoimide of the formula I is preferably selected from naphthalene-1,8-dicarboxylic monoimides of the formula I-C.

In another preferred embodiment of the present invention the polyethylene terephthalate is a partially crystalline polyethylene terephthalate and the polymer composition additionally includes at least one nucleating agent. Suitable nucleating agents are those mentioned above. The fraction of nucleating agent is generally from 0.05 to 1% by weight, based on the total weight of the polymer composition.

A further particularly preferred embodiment of the present invention relates to polyethylene terephthalate polymer compositions 12.1 to 12.54, which differ from the corresponding compositions 10.1 to 10.54 only in that the polyethylene terephthalate is a partially crystalline polyethylene terephthalate and the composition additionally includes at least one nucleating agent. The naphthalene-1,8-dicarboxylic monoimide of the formula I is preferably selected from naphthalene-1,8-dicarboxylic monoimides of the formula I-C.

Areas of application for polymer compositions comprising partially crystalline polyethylene terephthalate are optical films for displays, for example. In particular the naphthalene-1,8-dicarboxylic monoimide of the formula I is a naphthalene-1,8-dicarboxylic monoimide of the formula I-C.

A further particularly preferred embodiment of the present invention relates to compositions comprising
  at least one naphthalene-1,8-dicarboxylic monoimide as defined above;
  at least one high-density polyethylene or one polypropylene;
  at least one 2,6-dialkylated phenol antioxidant;
  if desired, at least one costabilizer selected from phosphites, phosphonites, and mixtures thereof;
  if desired, at least one further UV absorber, selected from diphenyl cyanoacrylates, hydroxybenzophenones, phenyl-1,3,5-triazines, benzotriazoles, and mixtures thereof;
  if desired, at least one sterically hindered amine; and
  if desired, a further component selected from dyes, pigments, and other additives.

Likewise preferred is the use of at least one naphthalene-1,8-dicarboxylic monoimide of the formula I as defined above in a composition comprising a high-density polyethylene or a polypropylene. The naphthalene-1,8-dicarboxylic monoimide of the formula I is preferably selected from the naphthalene-1,8-dicarboxylic monoimides I-C.

Examples of suitable 2,6-dialkylated phenols are those specified above, preferably the esters of β-(3,5-di-tert-butyl-4-hydroxyphenyl)propionic acid with monohydric or polyhydric alcohols, particularly pentaerythritol tetrakis[3-(3,5-di-tert-butyl-4-hydroxyphenyl)propionate] [CAS No. 6683-19-8], available commercially for example as Irganox® 1010 from Ciba Specialty Chemicals, Inc., and octadecyl 3-(3,5-di-tert-butyl-4-hydroxyphenyl)propionate [CAS No. 2082-79-3], available commercially for example as Irganox® 1076 from Ciba Specialty Chemicals, Inc., and mixtures thereof. The fraction of antioxidant is generally up to 4000 ppm, preferably from 1000 to 4000 ppm, based on the total weight of the polymer composition.

If desired the composition includes a costabilizer selected from phosphites, phosphonites, and mixtures thereof. Regarding suitable phosphites and phosphonites, the text above is incorporated in its entirety by reference. Preferred phosphites and phosphonites are tris(2,4-di-tert-butylphenyl)phosphite [CAS No. 31570-04-4], available commercially for example as Irgafos® 168 from Ciba Specialty Chemicals, Inc., and tetrakis(2,4-di-tert-butylphenyl)(1,1-biphenyl)-4,4'-diylbisphosphonite [CAS No. 119345-01-6], available commercially for example as Irgafos® P-EPQ from Ciba Specialty Chemicals, Inc., and mixtures thereof. The fraction of phosphite and/or phosphonite is generally up to 2000 ppm, preferably from 500 to 2000 ppm, in particular from 750 to 2000 ppm, based on the total weight of the polymer composition.

In a further preferred embodiment the polymer composition comprises not only at least one 2,6-dialkylated phenol antioxidant but also at least one phosphite and/or phosphonite costabilizer. The ratio of antioxidant to costabilizer is in that case generally in the range from 1:10 to 10:1.

The polymer composition may further comprise at least one other UV absorber. Suitable other UV absorbers are those mentioned above. The other UV absorbers are preferably selected from diphenylcyanoacrylates, hydroxybenzophenones, phenyl-1,3,5-triazines, benzotriazoles, and mixtures thereof.

Examples of suitable benzotriazoles are 2-(2'-hydroxyphenyl)benzotriazoles, preferably those mentioned above. Particular preference is given to the following:

- 2-(2H-benzotriazol-2-yl)-4,6-bis(1-methyl-1-phenylethyl)phenol [CAS No. 70321-86-7], available commercially for example as Tinuvin® 234 from Ciba Specialty Chemicals, Inc.;
- 2,4-di-tert-butyl-6-(5-chlorobenzotriazol-2-yl)phenol [CAS No. 3864-99-1], available commercially for example as Tinuvin® 327 from Ciba Specialty Chemicals, Inc.;
- 2-(2H-benzotriazol-2-yl)-4-(1,1,3,3-tetramethylbutyl)phenol [CAS No. 3147-75-9], available commercially for example as Tinuvin® 329 from Ciba Specialty Chemicals, Inc.;
- 2-(2H-benzotriazol-2-yl)-4-(tert-butyl)-6-(sec-butyl)phenol [CAS No. 36437-37-3], available commercially for example as Tinuvin® 350 from Ciba Specialty Chemicals, Inc.;
- 2,2'-methylenebis-(6-(2H-benzotriazol-2-yl)-4-1,1,3,3-tetramethylbutyl)phenol) [CAS No. 103597-45-1], available commercially for example as Tinuvin® 360 from Ciba Specialty Chemicals, Inc.; and
- transesterification products of methyl 3-(3-(2H-benzotriazol-2-yl)-5-tert-butyl-4-hydroxyphenyl)propionate with polyethylene glycol, obtainable for example as Tinuvin® 213 from Ciba Specialty Chemicals, Inc.

Examples of suitable 2-phenyl-1,3,5-triazines are 2-(2'-hydroxyphenyl)-1,3,5-triazines, preferably those mentioned above. Particular preference is given to the following:

- 2-(4,6-diphenyl-1,3,5-triazin-2-yl)-5-hexyloxyphenol [CAS No. 147315-50-2], available commercially for example as Tinuvin® 1577 from Ciba Specialty Chemicals, Inc.; and
- 2,4-Bis(2,4-dimethylphenyl)-6-(2-hydroxy-4-octyloxyphenyl)-1,3,5-triazine [CAS No. 2725-22-6], available commercially for example as Cyasorb® UV 1164 from Cytec.

Examples of suitable hydroxybenzophenones are 2-hydroxybenzophenones, preferably those mentioned above. Particular preference is given to:

- 2-hydroxy-4-n-octoxybenzophenone [CAS No. 1843-05-6], available commercially for example as Chimassorb® 81 from Ciba Specialty Chemicals, Inc.

Examples of suitable diphenylcyanoacrylates are those mentioned above. Preference is given to the following:

- 1,3-bis{[(2'-cyano-3',3'-diphenylacryloyl)oxy]-2,2-bis{[2'-cyano-3',3'-diphenyl-acryloyl)oxy]methyl}propane [CAS No. 178671-58-4], available commercially for example under the name Uvinul® 3030 from BASF AG, Ludwigshafen; and
- ethyl-2-cyano-3,3-diphenylacrylate [CAS No. 5232-99-5], available commercially for example under the name Uvinul® 3035 from BASF AG, Ludwigshafen.

In general the fraction of other UV absorbers is up to 2% by weight, preferably from 0.01 to 1.5% by weight, and in particular from 0.05-1% by weight, based on the total weight of the polymer composition. In the case of thin polymer layers the fraction of UV absorber used is generally higher than in the case of thick polymer layers.

The polymer composition comprising a high-density polyethylene or a polypropylene may further comprise at least one sterically hindered amine.

Suitable sterically hindered amines (HALS) are oligomeric and monomeric sterically hindered amines, examples being those mentioned above. Preferred sterically hindered amines are:

copolymers of (partially) N-piperidin-4-yl-substituted maleimide and a mixture of α-olefins, obtainable for example as Uvinul® 5050H [CAS 152261-33-1] (molar mass approximately 3500 g/mol) of the formula

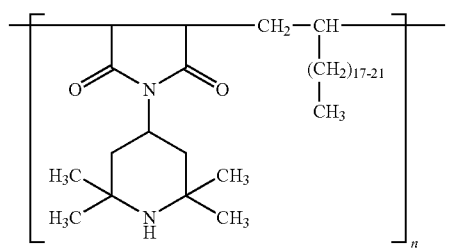

from BASF AG, Ludwigshafen;

the sterically hindered amine of the formula [CAS No. 124172-53-8]

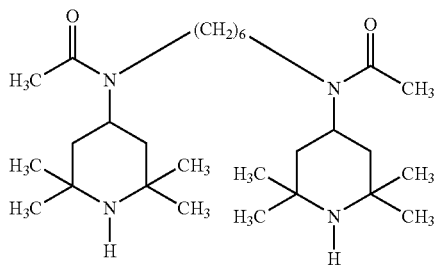

which is obtainable for example under the name Uvinul® 4050 H from BASF AG, Ludwigshafen;

poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]]) [CAS No. 71878-19-8], available commercially for example as Chimassorb® 944 (molar mass: 2000 to 3100 g/mol) from Ciba Specialty Chemicals, Inc.;

the dimethyl succinate polymer with 4-hydroxy-2,2,6,6-tetramethyl-1-piperidinoethanol [CAS number 65447-77-0], available commercially for example as Tinuvin® 622 (molar mass: 3100-4100 g/mol) from Ciba Specialty Chemicals, Inc.;

bis(2,2,6,6-tetramethyl-4-piperidyl)sebacate [CAS No. 52829-07-9], available commercially for example as Tinuvin® 770 from Ciba Specialty Chemicals, Inc.; and the polymer of 2,2,4,4-tetramethyl-7-oxa-3,20-diazadispiro[5.1.11.2]heneicosan-21-one and epichlorohydrin of the formula

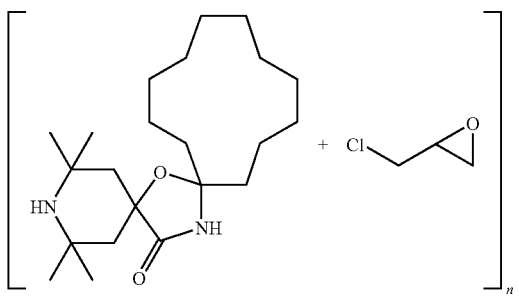

[CAS No. 202483-55-4], available commercially for example as Hostavin® N30 from Ciba Specialty Chemicals, Inc.

In general the fraction of sterically hindered amine is up to 2% by weight, preferably 0.1-2% by weight, in particular 0.1-0.15% by weight, very preferably 0.1-1% by weight, based on the total weight of the polymer composition. In the case of thin polymer layers the fraction of sterically hindered amine used is generally higher than in the case of thick polymer layers.

The polymer composition may additionally comprise at least one further component selected from dyes, pigments, and other additives. Suitable dyes and pigments are those mentioned above.

One especially preferred embodiment of the present invention relates to compositions which comprise at least one high-density polyethylene or one polypropylene, at least one naphthalene-1,8-dicarboxylic monoimide of the formula I as defined above, and, as (a) further component(s), the substance(s) indicated in a line of Table C (compositions 13.1 to 13.108). The naphthalene-1,8-dicarboxylic monoimide of the formula I is preferably selected from naphthalene-1,8-dicarboxylic monoimides of the formula I-C. The weight fractions of the individual constituents in the compositions 13.1 to 13.108 are situated within the ranges indicated above, based on the total weight of the polymer composition.

TABLE C

| Composition | Antioxidant CAS number | Costabilizer CAS number | Further light stabilizers (UV absorbers/HALS) CAS number |
|---|---|---|---|
| 13.1 | 6683-19-8 | | |
| 13.2 | 6683-19-8 | 31570-04-4 | |
| 13.3 | 6683-19-8 | | Tinuvin ® 213 |
| 13.4 | 6683-19-8 | | 70321-86-7 |
| 13.5 | 6683-19-8 | | 3864-99-1 |
| 13.6 | 6683-19-8 | | 3147-75-9 |
| 13.7 | 6683-19-8 | | 36437-37-3 |
| 13.8 | 6683-19-8 | | 103597-45-1 |
| 13.9 | 6683-19-8 | | 147315-50-2 |
| 13.10 | 6683-19-8 | | 1843-05-6 |
| 13.11 | 6683-19-8 | | 2725-22-6 |
| 13.12 | 6683-19-8 | | 178671-58-4 |
| 13.13 | 6683-19-8 | | 5232-99-5 |
| 13.14 | 6683-19-8 | | 71878-19-8 |
| 13.15 | 6683-19-8 | | 124172-53-8 |
| 13.16 | 6683-19-8 | | 152261-33-1 |
| 13.17 | 6683-19-8 | | 52829-07-9 |
| 13.18 | 6683-19-8 | | 65447-77-0 |
| 13.19 | 6683-19-8 | | 202483-55-4 |
| 13.20 | 6683-19-8 | 31570-04-4 | Tinuvin ® 213 |
| 13.21 | 6683-19-8 | 31570-04-4 | 70321-86-7 |
| 13.22 | 6683-19-8 | 31570-04-4 | 3864-99-1 |
| 13.23 | 6683-19-8 | 31570-04-4 | 3147-75-9 |
| 13.24 | 6683-19-8 | 31570-04-4 | 36437-37-3 |
| 13.25 | 6683-19-8 | 31570-04-4 | 103597-45-1 |
| 13.26 | 6683-19-8 | 31570-04-4 | 147315-50-2 |
| 13.27 | 6683-19-8 | 31570-04-4 | 1843-05-6 |
| 13.28 | 6683-19-8 | 31570-04-4 | 2725-22-6 |
| 13.29 | 6683-19-8 | 31570-04-4 | 178671-58-4 |
| 13.30 | 6683-19-8 | 31570-04-4 | 5232-99-5 |
| 13.31 | 6683-19-8 | 31570-04-4 | 71878-19-8 |
| 13.32 | 6683-19-8 | 31570-04-4 | 124172-53-8 |
| 13.33 | 6683-19-8 | 31570-04-4 | 152261-33-1 |
| 13.34 | 6683-19-8 | 31570-04-4 | 52829-07-9 |
| 13.35 | 6683-19-8 | 31570-04-4 | 65447-77-0 |
| 13.36 | 6683-19-8 | 31570-04-4 | 202483-55-4 |
| 13.37 | 6683-19-8 | 119345-01-6 | |
| 13.38 | 6683-19-8 | 119345-01-6 | Tinuvin ® 213 |
| 13.39 | 6683-19-8 | 119345-01-6 | 70321-86-7 |
| 13.40 | 6683-19-8 | 119345-01-6 | 3864-99-1 |
| 13.41 | 6683-19-8 | 119345-01-6 | 3147-75-9 |
| 13.42 | 6683-19-8 | 119345-01-6 | 36437-37-3 |
| 13.43 | 6683-19-8 | 119345-01-6 | 103597-45-1 |
| 13.44 | 6683-19-8 | 119345-01-6 | 147315-50-2 |
| 13.45 | 6683-19-8 | 119345-01-6 | 1843-05-6 |
| 13.46 | 6683-19-8 | 119345-01-6 | 2725-22-6 |
| 13.47 | 6683-19-8 | 119345-01-6 | 178671-58-4 |
| 13.48 | 6683-19-8 | 119345-01-6 | 5232-99-5 |
| 13.49 | 6683-19-8 | 119345-01-6 | 71878-19-8 |
| 13.50 | 6683-19-8 | 119345-01-6 | 124172-53-8 |
| 13.51 | 6683-19-8 | 119345-01-6 | 152261-33-1 |
| 13.52 | 6683-19-8 | 119345-01-6 | 52829-07-9 |
| 13.53 | 6683-19-8 | 119345-01-6 | 65447-77-0 |
| 13.54 | 6683-19-8 | 119345-01-6 | 202483-55-4 |
| 13.55 | 2082-79-3 | | |
| 13.56 | 2082-79-3 | 31570-04-4 | |
| 13.57 | 2082-79-3 | | Tinuvin ® 213 |
| 13.58 | 2082-79-3 | | 70321-86-7 |
| 13.59 | 2082-79-3 | | 3864-99-1 |
| 13.60 | 2082-79-3 | | 3147-75-9 |
| 13.61 | 2082-79-3 | | 36437-37-3 |
| 13.62 | 2082-79-3 | | 103597-45-1 |
| 13.63 | 2082-79-3 | | 147315-50-2 |
| 13.64 | 2082-79-3 | | 1843-05-6 |
| 13.65 | 2082-79-3 | | 2725-22-6 |
| 13.66 | 2082-79-3 | | 178671-58-4 |
| 13.67 | 2082-79-3 | | 5232-99-5 |
| 13.68 | 2082-79-3 | | 71878-19-8 |
| 13.69 | 2082-79-3 | | 124172-53-8 |
| 13.70 | 2082-79-3 | | 152261-33-1 |
| 13.71 | 2082-79-3 | | 52829-07-9 |
| 13.72 | 2082-79-3 | | 65447-77-0 |
| 13.73 | 2082-79-3 | | 202483-55-4 |
| 13.74 | 2082-79-3 | 31570-04-4 | Tinuvin ® 213 |
| 13.75 | 2082-79-3 | 31570-04-4 | 70321-86-7 |
| 13.76 | 2082-79-3 | 31570-04-4 | 3864-99-1 |
| 13.77 | 2082-79-3 | 31570-04-4 | 3147-75-9 |
| 13.78 | 2082-79-3 | 31570-04-4 | 36437-37-3 |
| 13.79 | 2082-79-3 | 31570-04-4 | 103597-45-1 |
| 13.80 | 2082-79-3 | 31570-04-4 | 147315-50-2 |
| 13.81 | 2082-79-3 | 31570-04-4 | 1843-05-6 |
| 13.82 | 2082-79-3 | 31570-04-4 | 2725-22-6 |
| 13.83 | 2082-79-3 | 31570-04-4 | 178671-58-4 |
| 13.84 | 2082-79-3 | 31570-04-4 | 5232-99-5 |
| 13.85 | 2082-79-3 | 31570-04-4 | 71878-19-8 |
| 13.86 | 2082-79-3 | 31570-04-4 | 124172-53-8 |
| 13.87 | 2082-79-3 | 31570-04-4 | 152261-33-1 |
| 13.88 | 2082-79-3 | 31570-04-4 | 52829-07-9 |
| 13.89 | 2082-79-3 | 31570-04-4 | 65447-77-0 |
| 13.90 | 2082-79-3 | 31570-04-4 | 202483-55-4 |
| 13.91 | 2082-79-3 | 119345-01-6 | |
| 13.92 | 2082-79-3 | 119345-01-6 | Tinuvin ® 213 |
| 13.93 | 2082-79-3 | 119345-01-6 | 70321-86-7 |
| 13.94 | 2082-79-3 | 119345-01-6 | 3864-99-1 |
| 13.95 | 2082-79-3 | 119345-01-6 | 3147-75-9 |
| 13.96 | 2082-79-3 | 119345-01-6 | 36437-37-3 |
| 13.97 | 2082-79-3 | 119345-01-6 | 103597-45-1 |
| 13.98 | 2082-79-3 | 119345-01-6 | 147315-50-2 |
| 13.99 | 2082-79-3 | 119345-01-6 | 1843-05-6 |

TABLE C-continued

| Composition | Antioxidant CAS number | Costabilizer CAS number | Further light stabilizers (UV absorbers/HALS) CAS number |
|---|---|---|---|
| 13.100 | 2082-79-3 | 119345-01-6 | 2725-22-6 |
| 13.101 | 2082-79-3 | 119345-01-6 | 178671-58-4 |
| 13.102 | 2082-79-3 | 119345-01-6 | 5232-99-5 |
| 13.103 | 2082-79-3 | 119345-01-6 | 71878-1 9-8 |
| 13.104 | 2082-79-3 | 119345-01-6 | 124172-53-8 |
| 13.105 | 2082-79-3 | 119345-01-6 | 152261-33-1 |
| 13.106 | 2082-79-3 | 119345-01-6 | 52829-07-9 |
| 13.107 | 2082-79-3 | 119345-01-6 | 65447-77-0 |
| 13.108 | 2082-79-3 | 119345-01-6 | 202483-55-4 |

Particular preference is given to the use of at least one naphthalene-1,8-dicarboxylic monoimide of the formula I in polymer compositions comprising at least one high-density polyethylene or one polypropylene for packing materials such as bottles or containers. The naphthalene-1,8-dicarboxylic monoimide of the formula I is preferably selected from naphthalene-1,8-dicarboxylic monoimides of the formula I-C.

A further particularly preferred embodiment of the present invention relates to compositions comprising
  at least one naphthalene-1,8-dicarboxylic monoimide of the formula I as defined above;
  at least one polystyrene;
  at least one 2,6-dialkylated phenol antioxidant;
  if desired, at least one costabilizer selected from phosphites, phosphonites, and mixtures thereof;
  if desired, at least one further UV absorber, selected from benzotriazoles, diphenylcyanoacrylates, and mixtures thereof;
  if desired, at least one sterically hindered amine; and
  if desired, at least one further component selected from dyes, pigments, and other additives.

Likewise preferred is the use of at least one naphthalene-1,8-dicarboxylic monoimide of the formula I as defined above in a polystyrene polymer composition. The naphthalene-1,8-dicarboxylic monoimide of the formula I is preferably selected from the naphthalene-1,8-dicarboxylic monoimides I-C.

Examples of suitable 2,6-dialkylated phenols are those specified above. Preferred 2,6-dialkylated phenols are the esters of β-(3,5-di-tert-butyl-4-hydroxyphenyl)propionic acid with monohydric or polyhydric alcohols, particularly pentaerythritol tetrakis[3-(3,5-di-tert-butyl-4-hydroxyphenyl)propionate] [CAS No. 6683-19-8], available commercially for example as Irganox® 1010 from Ciba Specialty Chemicals, Inc., and octadecyl 3-(3,5-di-tert-butyl-4-hydroxyphenyl)propionate [CAS No. 2082-79-3], available commercially for example as Irganox® 1076 from Ciba Specialty Chemicals, Inc., and mixtures thereof. The fraction of antioxidant is generally up to 2000 ppm, preferably from 500 to 2000 ppm, based on the total weight of the polymer composition.

Regarding suitable phosphites and phosphonites, the text above is incorporated in its entirety by reference. A preferred phosphite is tris(2,4-di-tert-butylphenyl)phosphite [CAS No. 31570-044], available commercially for example as Irgafos® 168 from Ciba Specialty Chemicals, Inc. The fraction of phosphite and/or phosphonite is generally up to 2000 ppm, preferably from 500 to 2000 ppm, based on the total weight of the polymer composition.

Preference is likewise given to mixtures comprising at least one 2,6-dialkylated phenol, preferably an ester of β-(3,5-di-tert-butyl-4-hydroxyphenyl)propionic acid with monohydric or polyhydric alcohols, as antioxidant, and also a phosphite and/or phosphonite as costabilizer. In that case the ratio of costabilizer to antioxidant is generally in the range from 10:1 to 1:10. Among such mixtures, particular preference is given to those comprising as costabilizer tris(2,4-di-tert-butylphenyl)phosphite [CAS No. 31570-04-4], available commercially for example as Irgafos® 168 from Ciba Specialty Chemicals, Inc., and as antioxidant pentaerythritol tetrakis[3-(3,5-di-tert-butyl-4-hydroxyphenyl)propionate] [CAS No. 6683-19-8], available commercially for example as Irganox® 1010 from Ciba Specialty Chemicals, Inc., or octadecyl 3-(3,5-di-tert-butyl-4-hydroxyphenyl)propionate [CAS No. 2082-79-3], available commercially for example as Irganox® 1076 from Ciba Specialty Chemicals, Inc. A preferred mixture is, for example, a mixture of 1 part octadecyl 3-(3,5-di-tert-butyl-4-hydroxyphenyl)propionate and 4 parts tris(2,4-di-tert-butylphenyl)phosphite, this mixture being available commercially for example as Irganox B900 from Ciba Specialty Chemicals, Inc.

The polystyrene polymer composition may further comprise at least one other UV absorber. Suitable other UV absorbers are those mentioned above. The other UV absorber is preferably selected from benzotriazoles, diphenylcyanoacrylates, and mixtures thereof.

Examples of suitable benzotriazoles are 2-(2'-hydroxyphenyl)benzotriazoles, preferably those mentioned above. Particular preference is given to the following:

2-(2H-benzotriazol-2-yl)-4,6-di-tert-pentylphenol [CAS No. 25973-55-1], available commercially for example as Tinuvin® 328 from Ciba Specialty Chemicals, Inc.; and 2-benzotriazol-2-yl-4-methylphenol [CAS No. 2440-22-4], available commercially for example as Tinuvin® P from Ciba Specialty Chemicals, Inc., and mixtures thereof.

Examples of suitable diphenylcyanoacrylates are those mentioned above. Preference is given to the following:

1,3-bis[(2'-cyano-3',3'-diphenylacryloyl)oxy]-2,2-bis{[2'-cyano-3',3'-diphenyl-acryloyl)oxy]methyl}propane [CAS No. 178671-58-4], available commercially for example under the name Uvinul® 3030 from BASF AG, Ludwigshafen; and ethyl-2-cyano-3,3-diphenylacrylate [CAS No. 5232-99-5], available commercially for example under the name Uvinul® 3035 from BASF AG, Ludwigshafen.

In general the fraction of other UV absorbers is up to 2% by weight, preferably from 0.01-1.5% by weight, and in particular from 0.05-1% by weight, based on the total weight of the polymer composition. In the case of thin polymer layers the fraction of UV absorber used is generally higher than in the case of thick polymer layers.

The polystyrene polymer composition may further comprise at least one sterically hindered amine.

Suitable sterically hindered amines are those mentioned above. The sterically hindered amine is preferably a compound of the formula

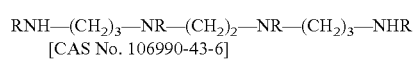
[CAS No. 106990-43-6]

where

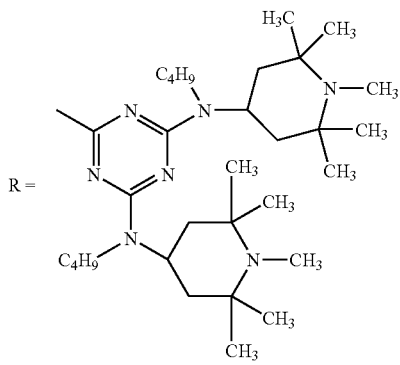

which is available commercially for example as Chimassorb® 119 from Ciba Specialty Chemicals, Inc., bis(2,2,6,6-tetramethyl-4-piperidyl)sebacate [CAS No. 52829-07-9], available commercially for example as Tinuvin® 770 from Ciba Specialty Chemicals, Inc., or mixtures thereof.

In general the fraction of sterically hindered amine is up to 2% by weight, preferably 0.1-1.5% by weight, in particular 0.1-0.5% by weight, based on the total weight of the polymer composition.

The polystyrene polymer composition may additionally comprise at least one further component selected from dyes, pigments, and other additives. Suitable dyes and pigments are those mentioned above.

One especially preferred embodiment of the present invention relates to polystyrene polymer compositions comprising at least one naphthalene-1,8-dicarboxylic monoimide of the formula I as defined above, and, as further components, the substances indicated in a line of Table D (compositions 14.1 to 14.45). The naphthalene-1,8-dicarboxylic monoimide of the formula I is preferably selected from naphthalene-1,8-dicarboxylic monoimides of the formula I-C. The weight fractions of the individual constituents in the compositions 14.1 to 14.45 are situated within the ranges indicated above, based on the total weight of the polymer composition.

TABLE D

| Composition | Costabilizer/antioxidant CAS No. | UV absorber CAS No. | sterically hindered amine CAS No. |
|---|---|---|---|
| 14.1 | 6683-19-8 | | |
| 14.2 | 6683-19-8 | 25973-55-1 | |
| 14.3 | 6683-19-8 | 2440-22-4 | |
| 14.4 | 6683-19-8 | 178671-58-4 | |
| 14.5 | 6683-19-8 | 5232-99-5 | |
| 14.6 | 6683-19-8 | | 106990-43-6 |
| 14.7 | 6683-19-8 | | 52829-07-9 |
| 14.8 | 6683-19-8 | 25973-55-1 | 106990-43-6 |
| 14.9 | 6683-19-8 | 2440-22-4 | 106990-43-6 |
| 14.10 | 6683-19-8 | 178671-58-4 | 106990-43-6 |
| 14.11 | 6683-19-8 | 5232-99-5 | 106990-43-6 |
| 14.12 | 6683-19-8 | 25973-55-1 | 52829-07-9 |
| 14.13 | 6683-19-8 | 2440-22-4 | 52829-07-9 |
| 14.14 | 6683-19-8 | 178671-58-4 | 52829-07-9 |
| 14.15 | 6683-19-8 | 5232-99-5 | 52829-07-9 |
| 14.16 | 2082-79-3 | | |
| 14.17 | 2082-79-3 | 25973-55-1 | |
| 14.18 | 2082-79-3 | 2440-22-4 | |
| 14.19 | 2082-79-3 | 178671-58-4 | |
| 14.20 | 2082-79-3 | 5232-99-5 | |
| 14.21 | 2082-79-3 | | 106990-43-6 |
| 14.22 | 2082-79-3 | | 52829-07-9 |
| 14.23 | 2082-79-3 | 25973-55-1 | 106990-43-6 |
| 14.24 | 2082-79-3 | 2440-22-4 | 106990-43-6 |
| 14.25 | 2082-79-3 | 178671-58-4 | 106990-43-6 |
| 14.26 | 2082-79-3 | 5232-99-5 | 106990-43-6 |
| 14.27 | 2082-79-3 | 25973-55-1 | 52829-07-9 |
| 14.28 | 2082-79-3 | 2440-22-4 | 52829-07-9 |
| 14.29 | 2082-79-3 | 178671-58-4 | 52829-07-9 |
| 14.30 | 2082-79-3 | 5232-99-5 | 52829-07-9 |
| 14.31 | 1 part 2082-79-3 and 4 parts 31570-04-4 | | |
| 14.32 | 1 part 2082-79-3 and 4 parts 31570-04-4 | 25973-55-1 | |
| 14.33 | 1 part 2082-79-3 and 4 parts 31570-04-4 | 2440-22-4 | |
| 14.34 | 1 part 2082-79-3 and 4 parts 31570-04-4 | 178671-58-4 | |
| 14.35 | 1 part 2082-79-3 and 4 parts 31570-04-4 | 5232-99-5 | |
| 14.36 | 1 part 2082-79-3 and 4 parts 31570-04-4 | | 106990-43-6 |
| 14.37 | 1 part 2082-79-3 and 4 parts 31570-04-4 | | 52829-07-9 |
| 14.38 | 1 part 2082-79-3 and 4 parts 31570-04-4 | 25973-55-1 | 106990-43-6 |
| 14.39 | 1 part 2082-79-3 and 4 parts 31570-04-4 | 2440-22-4 | 106990-43-6 |
| 14.40 | 1 part 2082-79-3 and 4 parts 31570-04-4 | 178671-58-4 | 106990-43-6 |
| 14.41 | 1 part 2082-79-3 and 4 parts 31570-04-4 | 5232-99-5 | 106990-43-6 |
| 14.42 | 1 part 2082-79-3 and 4 parts 31570-04-4 | 25973-55-1 | 52829-07-9 |
| 14.43 | 1 part 2082-79-3 and 4 parts 31570-04-4 | 2440-22-4 | 52829-07-9 |
| 14.44 | 1 part 2082-79-3 and 4 parts 31570-04-4 | 178671-58-4 | 52829-07-9 |
| 14.45 | 1 part 2082-79-3 and 4 parts 31570-04-4 | 5232-99-5 | 52829-07-9 |

Particular preference is given to the use of at least one naphthalene-1,8-dicarboxylic monoimide of the formula I in polystyrene polymer compositions for packaging such as yogurt pots and casings of electrical instruments. The naphthalene-1,8-dicarboxylic monoimide of the formula I is preferably selected from naphthalene-1,8-dicarboxylic monoimides of the formula I-C.

A further particularly preferred embodiment of the present invention relates to compositions comprising
    at least one naphthalene-1,8-dicarboxylic monoimide as defined above;
    at least one acrylonitrile-butadiene-styrene copolymer or styrene-acrylonitrile copolymer;
    at least one 2,6-dialkylated phenol antioxidant;
    if desired, at least one costabilizer selected from phosphites, phosphonites, and mixtures;
    if desired, at least one further UV absorber, selected from benzotriazoles, hydroxybenzophenones, diphenylcyanoacrylates, and mixtures thereof;
    if desired, at least one sterically hindered amine; and
    if desired, a further component selected from dyes, pigments, and other additives.

Likewise preferred is the use of at least one naphthalene-1,8-dicarboxylic monoimide of the formula I as defined above in an acrylonitrile-butadiene-styrene copolymer or styrene-acrylonitrile copolymer composition. The naphthalene-1,8-dicarboxylic monoimide of the formula I is preferably selected from the naphthalene-1,8-dicarboxylic monoimides I-C.

Examples of suitable 2,6-dialkylated phenols are the esters of β-(3,5-di-tert-butyl-4-hydroxyphenyl)propionic acid with monohydric or polyhydric alcohols and in particular octadecyl 3-(3,5-di-tert-butyl-4-hydroxyphenyl)propionate [CAS No. 2082-79-3], available commercially for example as Irganox® 1076 from Ciba Specialty Chemicals, Inc. The fraction of antioxidant is generally up to 2000 ppm, preferably from 500 to 2000 ppm, based on the total weight of the polymer composition.

Regarding suitable phosphites and phosphonites, the text above is incorporated in its entirety by reference. Preferred phosphites and phosphonites are tris(2,4-di-tert-butylphenyl)phosphite [CAS No. 31570-04-4], available commercially for example as Irgafos® 168 from Ciba Specialty Chemicals, Inc., and tetrakis(2,4-di-tert-butylphenyl)[1,1-biphenyl]-4,4'-diylbisphosphonite [CAS No. 119345-01-6], available commercially for example as Irgafos® P-EPQ from Ciba Specialty Chemicals, Inc., and mixtures thereof. The fraction of phosphite and/or phosphonite is generally up to 2000 ppm, preferably from 500 to 2000 ppm, based on the total weight of the polymer composition.

In another preferred embodiment the polymer composition comprises not only at least one 2,6-dialkylated phenol, preferably an ester of β-(3,5-di-tert-butyl-4-hydroxyphenyl)propionic acid with monohydric or polyhydric alcohols, as antioxidant, but also at least one phosphite and/or phosphonite as costabilizer. In that case the ratio of antioxidant to costabilizer is generally in the range from 1:10 to 10:1.

The polymer composition which comprises at least one acrylonitrile-butadiene-styrene copolymer or one styrene-acrylonitrile copolymer may additionally comprise at least one further UV absorber. Suitable other UV absorbers are those mentioned above. The other UV absorbers are preferably selected from benzotriazoles, hydroxybenzophenones, diphenylcyanoacrylates, and mixtures thereof.

Examples of suitable benzotriazoles are 2-(2'-hydroxyphenyl)benzotriazoles, preferably those mentioned above. Particular preference is given to the following:

2,4-di-tert-butyl-6-(5-chlorobenzotriazol-2-yl)phenol [CAS No. 3864-99-1], available commercially for example as Tinuvin® 327 from Ciba Specialty Chemicals, Inc., 2-benzotriazol-2-yl-4-methylphenol [CAS No. 2440-22-4], available commercially for example as Tinuvin® P from Ciba Specialty Chemicals, Inc.

Examples of suitable hydroxybenzophenones are 2-hydroxybenzophenones. Particular preference is given to 2-hydroxy-4-n-octoxybenzophenone [CAS No. 1843-05-6], available commercially for example as Chimassorb® 81 from Ciba Specialty Chemicals, Inc.

Examples of suitable diphenylcyanoacrylates are:

1,3-bis[(2'-cyano-3',3'-diphenylacryloyl)oxy]-2,2-bis{[2'-cyano-3',3'-diphenyl-acryloyl)oxy]methyl}propane [CAS No. 178671-58-4], available commercially for example under the name Uvinul® 3030 from BASF AG, Ludwigshafen; and ethyl-2-cyano-3,3-diphenylacrylate [CAS No. 5232-99-5], available commercially for example under the name Uvinul® 3035 from BASF AG, Ludwigshafen.

In general the fraction of other UV absorbers is up to 2% by weight, preferably from 0.01-1.5% by weight, and in particular from 0.05-1% by weight, based on the total weight of the polymer composition. In the case of thin polymer layers the fraction of UV absorber used is generally higher than in the case of thick polymer layers.

The acrylonitrile-butadiene-styrene copolymer or styrene-acrylonitrile copolymer composition may further comprise at least one sterically hindered amine. Suitable sterically hindered amines are those mentioned above. The sterically hindered amine is preferably a compound of the formula

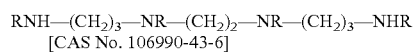
[CAS No. 106990-43-6]

where

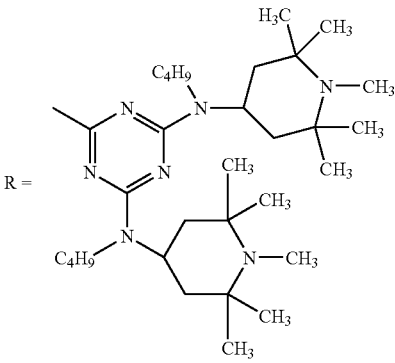

which is available commercially for example as Chimassorb® 119 from Ciba Specialty Chemicals, Inc., bis(2,2,6,6-tetramethyl-4-piperidyl)sebacate [CAS No. 52829-07-9], available commercially for example as Tinuvin® 770 from Ciba Specialty Chemicals, Inc., or mixtures thereof.

In general the fraction of sterically hindered amine is up to 2% by weight, preferably 0.1-1.5% by weight, in particular 0.1-1% by weight, very preferably 0.1-0.5% by weight, based on the total weight of the polymer composition.

The acrylonitrile-butadiene-styrene copolymer or styrene-acrylonitrile copolymer composition may additionally comprise at least one further component selected from dyes, pigments, and other additives. Suitable dyes and pigments are those mentioned above.

One especially preferred embodiment of the present invention relates to acrylonitrile-butadiene-styrene copolymer or styrene-acrylonitrile copolymer compositions comprising at least one naphthalene-1,8-dicarboxylic monoimide of the formula I as defined above, and, as further components, the substances indicated in a line of Table E (compositions 15.1 to 15.54). The naphthalene-1,8-dicarboxylic monoimide of the formula I is preferably selected from naphthalene-1,8-dicarboxylic monoimides of the formula I-C. The weight fractions of the individual constituents in the compositions 15.1 to 15.54 are situated within the ranges indicated above, based on the total weight of the polymer composition.

TABLE E

| Composition | Antioxidant/costabilizer CAS No. | UV absorber CAS No. | Sterically hindered amine CAS No. |
|---|---|---|---|
| 15.1 | 2082-79-3 | | |
| 15.2 | 2082-79-3 and 31570-04-4 | | |
| 15.3 | 2082-79-3 | 3864-99-1 | |
| 15.4 | 20 82-79-3 | 1843-05-6 | |

TABLE E-continued

| Composition | Antioxidant/costabilizer CAS No. | UV absorber CAS No. | Sterically hindered amine CAS No. |
|---|---|---|---|
| 15.5 | 2082-79-3 | 2440-22-2 | |
| 15.6 | 2082-79-3 | 178671-58-4 | |
| 15.7 | 2082-79-3 | 5232-99-5 | |
| 15.8 | 2082-79-3 | | 106990-43-6 |
| 15.9 | 2082-79-3 | | 52829-07-9 |
| 15.10 | 2082-79-3 | 3864-99-1 | 106990-43-6 |
| 15.11 | 2082-79-3 | 1843-05-6 | 106990-43-6 |
| 15.12 | 2082-79-3 | 2440-22-2 | 106990-43-6 |
| 15.13 | 2082-79-3 | 178671-58-4 | 106990-43-6 |
| 15.14 | 2082-79-3 | 5232-99-5 | 106990-43-6 |
| 15.15 | 2082-79-3 | 3864-99-1 | 52829-07-9 |
| 15.16 | 2082-79-3 | 1843-05-6 | 52829-07-9 |
| 15.17 | 2082-79-3 | 2440-22-2 | 52829-07-9 |
| 15.18 | 2082-79-3 | 178671-58-4 | 52829-07-9 |
| 15.19 | 2082-79-3 | 5232-99-5 | 52829-07-9 |
| 15.20 | 2082-79-3 and 31570-04-4 | 3864-99-1 | 106990-43-6 |
| 15.21 | 2082-79-3 and 31570-04-4 | 1843-05-6 | 106990-43-6 |
| 15.22 | 2082-79-3 and 31570-04-4 | 2440-22-2 | 106990-43-6 |
| 15.23 | 2082-79-3 and 31570-04-4 | 178671-58-4 | 106990-43-6 |
| 15.24 | 2082-79-3 and 31570-04-4 | 5232-99-5 | 106990-43-6 |
| 15.25 | 2082-79-3 and 31570-04-4 | 3864-99-1 | 52829-07-9 |
| 15.26 | 2082-79-3 and 31570-04-4 | 1843-05-6 | 52829-07-9 |
| 15.27 | 2082-79-3 and 31570-04-4 | 2440-22-2 | 52829-07-9 |
| 15.28 | 2082-79-3 and 31570-04-4 | 178671-58-4 | 52829-07-9 |
| 15.29 | 2082-79-3 and 31570-04-4 | 5232-99-5 | 52829-07-9 |
| 15.30 | 2082-79-3 and 119345-01-6 | | |
| 15.31 | 2082-79-3 and 119345-01-6 | 3864-99-1 | 106990-43-6 |
| 15.32 | 2082-79-3 and 119345-01-6 | 1843-05-6 | 106990-43-6 |
| 15.33 | 2082-79-3 and 119345-01-6 | 2440-22-2 | 106990-43-6 |
| 15.34 | 2082-79-3 and 119345-01-6 | 178671-58-4 | 106990-43-6 |
| 15.35 | 2082-79-3 and 119345-01-6 | 5232-99-5 | 106990-43-6 |
| 15.36 | 2082-79-3 and 119345-01-6 | 3864-99-1 | 52829-07-9 |
| 15.37 | 2082-79-3 and 119345-01-6 | 1843-05-6 | 52829-07-9 |
| 15.38 | 2082-79-3 and 119345-01-6 | 2440-22-2 | 52829-07-9 |
| 15.39 | 2082-79-3 and 119345-01-6 | 178671-58-4 | 52829-07-9 |
| 15.40 | 2082-79-3 and 119345-01-6 | 5232-99-5 | 52829-07-9 |
| 15.41 | 2082-79-3 and 31570-04-4 | 3864-99-1 | |
| 15.42 | 2082-79-3 and 31570-04-4 | 1843-05-6 | |
| 15.43 | 2082-79-3 and 31570-04-4 | 2440-22-2 | |
| 15.44 | 2082-79-3 and 31570-04-4 | 178671-58-4 | |
| 15.45 | 2082-79-3 and 31570-04-4 | 5232-99-5 | |
| 15.46 | 2082-79-3 and 31570-04-4 | | 106990-43-6 |
| 15.47 | 2082-79-3 and 31570-04-4 | | 52829-07-9 |
| 15.48 | 2082-79-3 and 119345-01-6 | 3864-99-1 | |
| 15.49 | 2082-79-3 and 119345-01-6 | 1843-05-6 | |
| 15.50 | 2082-79-3 and 119345-01-6 | 2440-22-2 | |
| 15.51 | 2082-79-3 and 119345-01-6 | 178671-58-4 | |
| 15.52 | 2082-79-3 and 119345-01-6 | 5232-99-5 | |
| 15.53 | 2082-79-3 and 119345-01-6 | | 106990-43-6 |
| 15.54 | 2082-79-3 and 119345-01-6 | | 52829-07-9 |

Particular preference is given to the use of at least one naphthalene-1,8-dicarboxylic monoimide of the formula I in acrylonitrile-butadiene-styrene copolymer or styrene-acrylonitrile copolymer compositions in components for automobiles and casings of electrical instruments. The naphthalene-1,8-dicarboxylic monoimide of the formula I is preferably selected from naphthalene-1,8-dicarboxylic monoimides of the formula I-C.

The present invention further provides a process for protecting organic material against the damaging effects of light, which involves adding to said material at least one naphthalene-1,8-dicarboxylic monoimide of the formula I as defined above.

The present invention further provides a process for protecting inanimate organic material against ultraviolet radiation, which involves producing the packaging using a plastic comprising at least one naphthalene-1,8-dicarboxylic monoimide I.

The present invention additionally provides for the use of a UV radiation absorbing layer to protect organic material from ultraviolet radiation.

The naphthalene-1,8-dicarboxylic monoimide I used in accordance with the invention and, where present, the compounds of groups a) to s) and/or the other additives of group t) are added to the plastic. Addition is made in a customary way, by blending with the plastic, for example. Thus the naphthalene-1,8-dicarboxylic monoimide I used in accordance with the invention and, where appropriate, the further stabilizers may also be added to the starting monomers, and the mixture of monomers and stabilizers can be polymerized. It is also possible to add the naphthalene-1,8-dicarboxylic monoimide I used in accordance with the invention and, where appropriate, the compounds of groups a) to s) and/or the other additives of group t) to the monomers during the polymerization. A precondition for addition before or during polymerization is that the naphthalene-1,8-dicarboxylic monoimide I used in accordance with the invention and, where appropriate, the compounds of groups a) to s) and/or the other additives of group t) are stable under the polymerization conditions: that is, that they exhibit little or no decomposition.

It is preferred to add the naphthalene-1,8-dicarboxylic monoimide I used in accordance with the invention and, where present, the compounds of groups a) to s) and/or the other additives of group t) to the finished plastic. This is effected in a usual fashion by mixing methods which are known per se: for example, with melting at temperatures from 150 to 300° C. However, the components can also be mixed "cold", without melting, and the powderous or granular mixture is not melted and homogenized until during processing.

It will be appreciated that the naphthalene-1,8-dicarboxylic monoimide I used in accordance with the invention and, where present, the compounds of groups a) to s) and/or the other additives of group t) can be added together or separately from one another, all at once, in portions, or continuously, at a constant rate or along a gradient. For example, part of the naphthalene-1,8-dicarboxylic monoimide used in accordance with the invention can be added to the monomers during the actual polymerization, and the remainder can be added only to the finished polymer, or all of the naphthalene-1,8-dicarboxylic monoimide can be added to the finished polymer.

Blending takes place preferably in a customary extruder, with the components being able to be introduced into the extruder as a mixture or individually, completely for example, by way of a hopper or else introduced proportionally at a later point in the extruder to the melt or solid product in the extruder. For melt extrusion particular suitability is possessed by, for example, single-screw or twin-screw extruders. A twin-screw extruder is preferred.

The mixtures obtained can be pelletized or granulated, for example, or processed by methods which are common knowledge: for example, by extrusion, injection molding, foaming with blowing agents, thermoforming, hollow body blowing or calendering.

The plastics can preferably be used to produce moldings (including semifinished products, films, sheets, and foams) of all kinds, examples being packaging and films, for textiles for example, particularly packaging for cosmetics, perfumes, and pharmaceutical products, and packaging and films for foods, beverage bottles, or packaging for cleaning products. It is also possible to produce stretch films from thermoplastic molding compounds.

Any product may in principle be protected by a packaging which comprises the naphthalene-1,8-dicarboxylic monoimide used in accordance with the invention. The product to be protected is preferably selected from cosmetics, drugs, perfumes, foods, and cleaning products. Suitable cosmetics include soap, body lotion, skin cream, shower gel, bubble bath, body spray, makeup, eyeliner, mascara, rouge, lipstick, shampoo, hair conditioner, hair gel, hair wax, hair lotion, nail varnish, nail varnish remover, etc. Suitable pharmaceutical products include pharmaceutical compositions or drugs in the form of tablets, pills, film-coated tablets, suppositories, solutions, concentrates, suspensions, and the like. Suitable foodstuffs include carbonated and noncarbonated beverages, examples being carbonated beverages such as lemonade, beer, carbonated fruit juice drinks, carbonated water, noncarbonated beverages such as wine, fruit juice, tea or coffee, fruit, meat, sausage, dairy products such as milk, yogurt, butter or cheese, animal and vegetable fats, bakery products, pasta, seasonings, sauces, pastes, pestos, stocks, purees, ketchups, dressings, etc. Suitable cleaning products include household cleaners and industrial cleaners.

The naphthalene-1,8-dicarboxylic monoimide I to be employed in accordance with the invention is used with particular preference in thermoplastic molding compounds comprising polyolefins for agricultural films and packaging films, in biaxially oriented polypropylene for stretch-wrap films, in polyethylene terephthalate or polyethylene naphthalate for bottles and other container packs, in polyvinyl butyral for laminated glass, in polystyrene for blister packs and other packaging containers, in polycarbonate for bottles, flasks and other packaging containers and moldings, in polyvinyl chloride for packaging containers and films, or in polyvinyl alcohol for producing films.

Where appropriate, the films of different polymers can be combined with one another by lamination or in the form of extrusion laminates to form composite films. By monoaxial or biaxial stretching it is possible where appropriate to improve the properties. This is utilized, for example, in order to produce shrink films. Shrink films can be produced from polyethylene terephthalate, polyethylene, polyvinylidene chloride or polyvinyl chloride, for example.

The materials stabilized using at least one naphthalene-1,8-dicarboxylic monoimide I exhibit particular quality features in comparison to unstabilized materials and to materials stabilized with prior art stabilizers. The materials stabilized in accordance with the invention feature an extended exposure time, since light-induced damage does not begin until later. Moreover, the material stabilized using at least one naphthalene-1,8-dicarboxylic monoimide protects not only the material to be stabilized but also the packaged contents.

The examples below are intended to illustrate the invention, though without restricting it.

I. PREPARATION EXAMPLES

Example 1

Preparation of 4-cyano-N-(2,6-diisopropylphenyl) naphthalene-1,8-dicarboximide (compound I-A.1)

1.1 Preparation of 4-bromo-N-(2,6-diisopropylphenyl)-naphthalene-1,8-dicarboximide 27.7 g of 4-bromonaphthalene-1,8-dicarboxylic anhydride, 19.0 g of 2,6-diisopropylaniline and 9.2 g of anhydrous zinc acetate in 65 ml of N-methylpyrrolidone were heated at 200° C. for 3 hours. After cooling, the precipitate formed was filtered off, washed and dried to give 26.2 g of 4-bromo-N-(2,6-diisopropylphenyl)naphthalene-1,8-dicarboximide having a melting point of 277° C.

1.2 Preparation of 4-cyano-N-(2,6-diisopropylphenyl)naphthalene-1,8-dicarboximide 24.8 g of 4-bromo-N-(2,6-diisopropylphenyl)naphthalene-1,8-dicarboximide and 7.5 g of copper(I) cyanide in 150 ml of N-methylpyrrolidone were heated at 210° C. for 4 hours. After cooling, water was added to the reaction mixture, producing a precipitate. The precipitate was filtered off, washed and dried. Column chromatography of the precipitate on silica gel (eluent: dichloromethane) gave 15.6 g of 4-cyano-N-(2,6-diisopropylphenyl)naphthalene-1,8-dicarboximide having a melting point of 291° C.

Elemental analysis: $C_{25}H_{22}N_2O_2$ (382.5 g/mol): calc.: C, 78.5; H, 5.8; N, 7.3; O 8.4. found: C, 78.5; H, 5.9; N, 7.0; O 8.4;

UV (dichloromethane): $\lambda_{max}$ (lg $\epsilon$) 352 nm (4.16).

Following the method described in Example 1, in Examples 2 to 5 the 4-cyano-substituted naphthalene-1,8-dicarboxylic monoimides I-A.2 to I-A.5 were prepared. The melting points and spectroscopic properties of the 4-cyano-substituted naphthalene-1,8-dicarboxylic monoimides I-A.1 to I-A.5 are summarized in Table 1. Dichloromethane was used as solvent for the UV spectroscopy.

TABLE 1

(I-A)

| Example | R¹ | Compound | m.p. [° C.] | $\lambda_{max}$ [nm] | lg ε |
|---|---|---|---|---|---|
| 1 | 2,6-diisopropylphenyl | I-A.1 | 291 | 352 | 4.16 |
| 2 | Cyclohexyl | I-A.2 | 258 | 354 | 4.10 |
| 3 | 4-tert-butylcyclohexyl (cis and trans) | I-A.3 | 213 | 354 | 4.05 |
| 4 | Phenyl | I-A.4 | >300 | 354 | 4.15 |
| 5 | 2,4,6-trimethylphenyl | I-A.5 | 305 | 352 | 4.17 |

Example 6

Preparation of 4-aminocarbonyl-N-(2,6-diisopropylphenyl)naphthalene-1,8-dicarboximide (compound I-B.1)

8 g of 4-cyano-N-(2,6-diisopropylphenyl)naphthalene-1,8-dicarboximide from Example 1 in 130 ml of concentrated sulfuric acid were heated at 80° C. for 3 hours. The reaction mixture was subsequently poured into ice-water and the precipitate formed was filtered off, washed and dried. This gave 5.1 g of 4-aminocarbonyl-N-(2,6-diisopropylphenyl)-naphthalene-1,8-dicarboximide having a melting point of 233° C.

UV (dichloromethane): $\lambda_{max}$ (lg ε): 336 nm (4.18).

Example 7

Preparation of N-(2,6-diisopropylphenyl)-4-(4-tert-octylphenoxy)-naphthalene-1,8-dicarboximide (compound I-C.1)

7.1 Preparation of 4-chloro-N-(2,6-diisopropylphenyl)naphthalene-1,8-dicarboximide A mixture of 23.3 g of 4-chloronaphthalene-1,8-dicarboxylic anhydride, 19.0 g of 2,6-diisopropylaniline and 9.2 g of anhydrous zinc acetate in 65 ml of N-methylpyrrolidone was heated at 200° C. for 3 hours. After cooling, the precipitate formed was filtered off, washed and dried. This gave 22.4 g of 4-chloro-N-(2,6-diisopropylphenyl)naphthalene-1,8-dicarboximide having a melting point of 289° C.

7.2 Preparation of N-(2,6-diisopropylphenyl)-4-(4-tert-octylphenoxy)naphthalene-1,8-dicarboximide A mixture of 5.0 g of 4-chloro-N-(2,6-diisopropylphenyl) naphthalene-1,8-dicarboximide from 7.1, 3.5 g of 4-(1,1,3,3-tetramethylbutyl)phenol(tert-octylphenol) and 1.2 g of potassium carbonate in 60 ml of N-methylpyrrolidone was heated at 80° C. for 24 hours. It was cooled and methanol and water were added to the reaction mixture, producing a precipitate. The precipitate thus obtained was filtered off, washed and dried to give 6.2 g of N-(2,6-diisopropylphenyl)-4-(4-tert-octylphenoxy)naphthalene-1,8-dicarboximide having a melting point of 217° C.

¹H-NMR (DMSO-d₆): δ [ppm]: 0.78 (s, 9H), 1.12 (t, J=7.3 Hz, 6H), 1.42 (s, 6 H), 1.80 (s, 2H), 2.75 (sept, J=6.8 Hz, 2H), 6.93 (d, J=8.5 Hz, 1H), 7.15 (d, J=8.5 Hz, 2H), 7.32 (d, J=7.5 Hz, 2H), 7.48 (t, J=7.5 Hz, 1H), 7.52 (d, J=9.0 Hz, 2H), 7.82 (dd, J=8.0, 7.0 Hz, 1H), 8.48 (d, J=9.5 Hz, 1H), 8.68 (dd, J=7.0, 1.0 Hz, 1H), 8.80 (dd, J=8.5, 1.5Hz, 1H);

¹³C-NMR (DMSO-d₆): δ[ppm]: 24.1 (q), 29.4 (d); 31.8 (q), 31.9 (q), 32.6 (s), 38.8 (s), 57.4 (t), 110.6 (d), 116.6 (s), 120.4 (d), 123.0 (s), 124.3 (d), 124.5 (d), 126.8 (d), 128.6 (d), 129.3 (d), 129.6 (d), 130.7 (s) 132.0 (s), 135.5 (d), 133.6 (d), 146.5 (s), 148.2 (s), 152.6 (s), 161.0 (s), 164.2 (s), 164.8 (s);

UV (dichloromethane): $\lambda_{max}$ (lg ε) 364 nm (4.22).

Following the method described in Example 7, in Examples 8 to 16 the 4-phenoxy-substituted naphthalene-1,8-dicarboxylic monoimides I-C.2 to I-C.10 were prepared. The melting points and spectroscopic properties of the 4-phenoxy-substituted naphthalene-1,8-dicarboxylic monoimides I-C.1 to I-C.10 are summarized in Table 2. Dichloromethane was used as solvent for the UV spectroscopy.

TABLE 2

(I-C)

| Example | R¹ | R | Compound | m.p. [° C.] | $\lambda_{max}$ [nm] | lg ε |
|---|---|---|---|---|---|---|
| 7 | 2,6-diisopropylphenyl | tert-octyl | I-C.1 | 217 | 364 | 4.22 |
| 8 | 2,6-diisopropylphenyl | isopropyl | I-C.2 | 200 | 364 | 4.21 |
| 9 | 2,6-diisopropylphenyl | tert-pentyl | I-C.3 | 256 | 364 | 4.22 |
| 10 | phenyl | tert-octyl | I-C.4 | 222 | 364 | 4.21 |
| 11 | phenyl | isopropyl | I-C.5 | 193 | 364 | 4.24 |

TABLE 2-continued (I-C)

[Structure: naphthalene-1,8-dicarboximide with N–R¹ on the imide nitrogen and an O-phenyl ether substituent (phenyl bearing R) at the peri position]

| Example | R¹ | R | Compound | m.p. [°C.] | $\lambda_{max}$ [nm] | lg ε |
|---|---|---|---|---|---|---|
| 12 | phenyl | tert-pentyl | I-C.6 | 196 | 364 | 4.18 |
| 13 | 2-ethylhexyl | tert-octyl | I-C.7 | 124 | 364 | 4.19 |
| 14 | 2-ethylhexyl | isopropyl | I-C.8 | 94 | 362 | 4.20 |
| 15 | 2-ethylhexyl | tert-pentyl | I-C.9 | 120 | 364 | 4.15 |
| 16 | 2,4,6-trimethylphenyl | tert-octyl | I-C.10 | 221 | 364 | 4.22 |

II. USE EXAMPLES

Examples 17-20

Incorporation of the UV Absorbers into Polyethylene Terephthalate (PET) Film

A mixture of a polyethylene terephthalate (Polyclear T94 from Ter Hell & Co GmbH, Hamburg) and the concentration of compound I stated in Table 3 was homogenized in a Berstorff twin-screw extruder (melt temperature: 275° C.) and then granulated. The resultant granules were subsequently extruded in a Weber single-screw extruder through a slot die (melt temperature: 225° C.) and pressed to a thickness of 300 µm via a roll takeoff.

The results are summarized in Table 3. The parameters reported are the wavelengths below which less than 10% or 20% of the radiation passes through the film. A value below and preferably close to 400 nm signifies that the material beneath the film is effectively protected against UV radiation.

TABLE 3

| Example | Compound | Concentration [%] | Wavelength 10%ᵃ [nm] | Wavelength 20%ᵇ [nm] |
|---|---|---|---|---|
| 17 | I-A.1 | 0.4 | 371 | 372 |
| 18 | I-B.1 | 0.2 | 355 | 362 |
| 19 | I-B.1 | 0.4 | 369 | 371 |
| 20 | I-C.1 | 0.2 | 388 | 394 |
| 21 | Without UV absorber (PET alone) | | 318 | 319 |

ᵃMaximum wavelength with a transmittance of less than 10%.
ᵇMaximum wavelength with a transmittance of less than 20%

The examples show that the naphthalene-1,8-dicarboxylic monoimide I used in accordance with the invention can be incorporated effectively into the PET films. The naphthalene-1,8-dicarboxylic monoimides I used in accordance with the invention filter the major part of the damaging UV radiation from the spectrum and are therefore suitable as effective UV filters.

Example 22

Exposure of an Additized PET Film

The PET film from Example 17 (containing 0.4% of compound I-A.1) was exposed for 1000 hours in accordance with DIN 54004. The transmittance profile of the film was measured at regular intervals and is shown in Table 4.

TABLE 4

| Exposure time [h] | Wavelength 10%ᵃ [nm] | Wavelength 20%ᵇ [nm] |
|---|---|---|
| 0 | 371 | 372 |
| 200 | 371 | 372 |
| 400 | 371 | 372 |
| 600 | 371 | 372 |
| 1000 | 370 | 372 |

ᵃMaximum wavelength with a transmittance of less than 10%.
ᵇMaximum wavelength with a transmittance of less than 20%

Example 23

Exposure of an Additized PET Film

The PET film from Example 20 (containing 0.2% of compound I-C.1) was exposed for 1000 hours in accordance with DIN 54004. The transmittance profile of the film was measured at regular intervals and is shown in Table 5.

TABLE 5

| Exposure time [h] | Wavelength 10%ᵃ [nm] | Wavelength 20%ᵇ [nm] |
|---|---|---|
| 0 | 389 | 394 |
| 1000 | 388 | 393 |

ᵃMaximum wavelength with a transmittance of less than 10%.
ᵇMaximum wavelength with a transmittance of less than 20%

Examples 22 and 23 show that the naphthalene-1,8-dicarboxylic monoimides I are photostable, i.e., are not broken down. Accordingly the naphthalene-1,8-dicarboxylic monoimides I are suitable long-term UV filter substances.

Examples 24 to 30

Production of PET Moldings (Thickness: 1 mm)

As described in Examples 17 to 20, in Examples 24 to 28 granules of PET and the concentration of compound I indicated in Table 6, and, in Examples 29 and 30 (comparative), granules of PET and the concentration indicated in Table 6 of a commercially customary UV absorber (2-(2H-benzotriazol-2-yl)-4,6-bis(1-methyl-1-phenylethyl)phenol (CAS number 70321-86-7), available commercially for example under the name Tinuvin® 234 from Ciba Specialty Chemicals) were produced. Thereafter injection moldings with a thickness of 1 mm were produced in an Arburg 220M injection molding machine. In Example 24 (control) the PET molding contained no UV absorber. In Example 28 the PET molding contains an additional 0.1% by weight of a further UV absorber, namely 1,3-bis[(2'-cyano-3',3'-diphenylacryloyl)oxy]-2,2-bis{[2'-cyano-3',3'-diphenylacryloyl)oxy]methyl}propane [CAS No. 178671-58-4], available commercially for example under the name Uvinul® 3030 from BASF AG, Ludwigshafen.

The yellowness indices (YI, in accordance with DIN 6167) of the injection moldings of Examples 24 to 30 are reported in Table 6. A yellowness index of zero means that the specimen is pure white. Negative YI values mean that the specimen is bluish (the more negative YI, the bluer). Positive YI values indicate that the specimen is yellowish. The more positive the YI, the yellower the specimen appears to the viewer. Addition of a UV absorber to a plastic generally entails an increase in YI.

solution is protected by a naphthalene-1,8-dicarboxylic monoimide I used in accordance with the invention.

Examples 32 to 37

Production of Polycarbonate Moldings

As described in Examples 17 to 20, in Examples 32 to 35 granules of polycarbonate (Makrolon 2800 from Bayer AG, Leverkusen) and the concentration of compound I-C.1 indicated in Table 7, and, in Examples 36 and 37 (comparative), granules of polycarbonate (Makrolon 2800 from Bayer AG, Leverkusen) and the concentration indicated in Table 7 of a commercially customary UV absorber (2-(2H-benzotriazol-2-yl)-4,6-bis(1-methyl-1-phenylethyl)phenol (CAS number 70321-86-7), available commercially for example under the name Tinuvin® 234 from Ciba Specialty Chemicals) were produced. Thereafter injection moldings with a thickness of 1 mm were produced in an Arburg 220M injection molding machine. In Example 32 (control) the polycarbonate molding contains no UV absorber. In Example 35 the polycarbonate molding contains an additional 0.1% by weight of a further UV absorber, namely 1,3-bis[(2'-cyano-3',3'-diphenylacryloyl)oxy]-2,2-bis{[2'-cyano-3',3'-diphenyl-acryloyl)oxy]methyl}propane [CAS No. 178671-58-4], available commercially for example under the name Uvinul® 3030 from BASF AG, Ludwigshafen.

The yellowness indices (YI, in accordance with DIN 6167) and the transmittance properties of the moldings of Examples 32-37 are reported in Table 7 below.

TABLE 6

| Ex. | UV absorber | Concentration [% by weight] | Wavelength 10%[a] [nm] | Wavelength 20%[b] [nm] | YI |
|---|---|---|---|---|---|
| 24 (control) | none | — | 324 | 328 | 2.5 |
| 25 | I-A.1 | 0.2 | 374 | 377 | 4.2 |
| 26 | I-C.1 | 0.2 | 400 | 402 | −4.1 |
| 27 | I-C.1 | 0.1 | 392 | 396 | 0.4 |
| 28 | I-C.1/CAS No. 178671-58-4 (1:1) | 0.2 | 397 | 400 | 0.2 |
| 29 (comparative) | CAS No. 70321-86-7 | 0.1 | 383 | 387 | 7.8 |
| 30 (comparative) | CAS No. 70321-86-7 | 0.2 | 386 | 389 | 4.9 |

[a]Maximum wavelength with a transmittance of less than 10%.
[b]Maximum wavelength with a transmittance of less than 20%.

Example 31

Protection of Vitamin A

An ethanolic solution of vitamin A ($c=10^{-5}$ mol/l) was exposed in a cuvette to a xenon lamp. PET plaques from Examples 24-26 were placed in the beam path of the xenon lamp. During irradiation, the remaining concentration of vitamin A was measured from its absorbance at 323 nm. FIG. 1 shows the filter effect of the compounds I used in accordance with the invention, as a graph. Since the emissions spectrum of a xenon lamp is similar to that of the sun, FIG. 1 forcefully demonstrates the filter effect of the naphthalene-1,8-dicarboxylic monoimides I used in accordance with the invention. Without the protection of naphthalene-1,8-dicarboxylic monoimides I a vitamin A solution is rapidly broken down by light. In contrast, there is only slight breakdown of the vitamin A solution under the effect of light if the vitamin A

TABLE 7

| Ex. | UV absorber | Concentration [% by weight] | Wavelength 10%*[a] [nm] | Wavelength 20%* [nm] | YI |
|---|---|---|---|---|---|
| 32 (control) | none | — | —[c] | 298 | 3.0 |
| 33 | I-C.1 | 0.1 | 390 | 393 | −2.3 |
| 34 | I-C.1 | 0.2 | 395 | 398 | −2.3 |
| 35 | I-C.1/CAS No. 178671-58-4 (1:1) | 0.2 | 387 | 391 | 0.8 |
| 36 (comparative) | CAS No. 70321-86-7 | 0.1 | 380 | 384 | 4.8 |

Examples 38-43

Production of Polystyrene Moldings

As described in Examples 17-20, in Examples 38 to 41 granules of polystyrene (Polystyrol 144C from BASF AG, Ludwigshafen) and the concentration of compound I-C.1 indicated in Table 8, and, in Examples 42 and 43 (comparative), granules of polystyrene (Polystyrol 144C from BASF AG, Ludwigshafen) and the concentration indicated in Table 8 of a commercially customary UV absorber (2-(2H-benzotriazol-2-yl)-4,6-bis(1-methyl-1-phenylethyl)phenol (CAS number 70321-86-7), available commercially for example under the name Tinuvin® 234 from Ciba Specialty Chemicals) were produced. Thereafter injection moldings with a thickness of 1 mm were produced in an Arburg 220M injection molding machine. In Example 38 (control) the polystyrene molding contains no UV absorber. In Example 41 the polystyrene molding contains an additional 0.1% by weight of a further UV absorber, namely 1,3-bis[(2'-cyano-3',3'-diphenylacryloyl)oxy]-2,2-bis{[2'-cyano-3',3'-diphenylacryloyl)oxy]methyl}propane [CAS No. 178671-58-4], available commercially for example under the name Uvinul® 3030 from BASF AG, Ludwigshafen.

The yellowness indices (YI, in accordance with DIN 6167) and the transmittance properties of the moldings of Examples 38-43 are reported in Table 8 below.

TABLE 8

| Ex. | UV absorber | Concentration [% by weight] | Wavelength 10%$^a$ [nm] | Wavelength 20%$^b$ [nm] | YI |
|---|---|---|---|---|---|
| 38 (control) | none | — | —$^c$ | —$^c$ | 0.4 |
| 39 | I-C.1 | 0.1 | 373 | 385 | −3.7 |
| 40 | I-C.1 | 0.2 | 391 | 393 | −5.5 |
| 41 | I-C.1/CAS No. 178671-58-4 (1:1) | 0.2 | 391 | 393 | −3.5 |
| 42 (comparative) | CAS No. 70321-86-7 | 0.1 | 379 | 383 | 1.1 |
| 43 (comparative) | CAS No. 70321-86-7 | 0.2 | 383 | 387 | 2.8 |

$^a$Maximum wavelength with a transmittance of less than 10%.
$^b$Maximum wavelength with a transmittance of less than 20%.
$^c$The transmittance of the molding does not fall below the corresponding value for the wavelengths measured (250-1000 nm).

Examples 44-49

Production of Acrylonitrile-Butadiene-Styrene Copolymer Moldings

As described in Examples 17-20, in Examples 44 to 47 granules of acrylonitrile-butadiene-styrene copolymer (Terluran GP22 from BASF AG, Ludwigshafen) and the concentration of compound I-C.1 indicated in Table 9, and, in Examples 48 and 49 (comparative), granules of acrylonitrile-butadiene-styrene copolymer (Terluran GP22 from BASF AG, Ludwigshafen) and the concentration indicated in Table 9 of a commercially customary UV absorber (2-(2H-benzotriazol-2-yl)-4,6-bis(1-methyl-1-phenylethyl)phenol (CAS number 70321-86-7), available commercially for example under the name Tinuvin® 234 from Ciba Specialty Chemicals) were produced. Thereafter injection moldings with a thickness of 1 mm were produced in an Arburg 220M injection molding machine. In Example 44 (control) the ABS molding contains no UV absorber. In Example 47 the ABS molding contains an additional 0.1% by weight of a further UV absorber in a ratio of 1:1, namely 1,3-bis[(2'-cyano-3',3'-diphenylacryloyl)oxy]-2,2-bis{[2'-cyano-3',3'-diphenylacryloyl)oxy]methyl}propane [CAS No. 178671-58-4], available commercially for example under the name Uvinul® 3030 from BASF AG, Ludwigshafen.

The yellowness indices (YI, in accordance with DIN 6167) and the transmittance properties of the moldings of Examples 44-49 are reported in Table 9 below.

TABLE 9

| Ex. | UV absorber | Concentration [% by weight] | Wavelength 10%$^a$ [nm] | Wavelength 20%$^b$ [nm] | YI |
|---|---|---|---|---|---|
| 44 (control) | none | — | 373 | 386 | 18.9 |
| 45 | I-C.1 | 0.1% | 401 | 407 | 20.3 |
| 46 | I-C.1 | 0.2% | 404 | 409 | 4.6 |
| 47 | I-C.1/ CAS No. 178671-58-4 (1:1) | 0.2% | 403 | 408 | 8.5 |
| 48 (comparative) | CAS No. 70321-86-7 | 0.1 | 393 | 400 | 22.4 |
| 49 (comparative) | CAS No. 70321-86-7 | 0.2 | 397 | 404 | 25.1 |

$^a$Maximum wavelength with a transmittance of less than 10%.
$^b$Maximum wavelength with a transmittance of less than 20%.
$^c$The transmittance of the molding does not fall below the corresponding value for the wavelengths measured (250-1000 nm).

Examples 25 to 49 show that the naphthalene-1,8-dicarboxylic monoimides of the formula I used in accordance with the invention can be incorporated effectively into a variety of polymers. Mixtures with UVB absorbers are likewise highly compatible with the polymers. The injection moldings comprising the absorbers of the invention filter out the major part of the damaging UV radiation and yet for the most part have a much lower yellowness index than injection moldings without absorber. The samples stabilized with the naphthalene-1, 8-dicarboxylic monoimide of the formula I in particular

---

TABLE 7-continued

| Ex. | UV absorber | Concentration [% by weight] | Wavelength 10%$^{*a}$ [nm] | Wavelength 20%* [nm] | YI |
|---|---|---|---|---|---|
| 37 (comparative) | CAS No. 70321-86-7 | 0.2 | 389 | | 3.3 |

$^a$Maximum wavelength with a transmittance of less than 10%.
$^b$Maximum wavelength with a transmittance of less than 20%.
$^c$The transmittance of the molding does not fall below the corresponding value for the wavelengths measured (250-1000 nm).

showed a much lower yellow coloration than the samples stabilized with a commercially customary stabilizer.

Examples 50 to 54

Transmittance Profiles of Glass Laminates Comprising an Additized Polyvinyl Butyral Film A polyvinyl butyral film 0.76 mm thick was prepared as described in Example 6 of WO 02/077081 and was then used to produce a glass laminate—there was deviation from Example 6 of WO 02/077081 in that no IR absorber was used, and the Tinuvin benzotriazole derivative (15.8 g (0.5% by weight)) was replaced by:

(a) a mixture of 0.1% by weight 1,3-bis[(2'-cyano-3',3'-diphenylacryloyl)oxy]-2,2-bis{[2'-cyano-3',3'-diphenylacryloyl)oxy]methyl}propane and 0.1% by weight I-C.1 (Example 50), (b) a mixture of 0.1% by weight 2-(3'-tert-butyl-2'-hydroxy-5'-methylphenyl)-5-chlorobenzotriazole and 0.1% by weight I-C.1 (Example 51), (c) a mixture of 0.1% by weight 2-hydroxy-4-n-octoxybenzophenone and 0.1% by weight I-C.1 (Example 52), or (d) 0.2% by weight I-C.1 (Example 53).

For comparison, in Example 54 a 0.76 mm polyvinyl butyral film was produced in the same way, and a glass laminate was produced from it, using neither an IR absorber nor a UV absorber.

The transmittance profiles of the glass laminates produced in Examples 50 to 54 are reported in Table 10.

TABLE 10

| Example | Wavelength 10%$^a$ [nm] | Wavelength 20%$^b$ [nm] |
|---|---|---|
| 50 | 390 | 394 |
| 51 | 392 | 396 |
| 52 | 389 | 394 |
| 53 | 393 | 396 |
| 54 (no UV absorber) | 288 | 289 |

$^a$Maximum wavelength with a transmittance of less than 10%.
$^b$Maximum wavelength with a transmittance of less than 20%.

Examples 50 to 54 show that a glass laminate comprising the naphthalene-1,8-dicarboxylic monoimides I used in accordance with the invention or mixtures of the naphthalene-1,8-dicarboxylic monoimides I used in accordance with the invention with shortwave-absorbing UV absorbers is capable of absorbing UV radiation almost completely and hence of effectively protecting the area lying behind it against the effects of said radiation.

The invention claimed is:

1. A process for protecting organic material from the damaging effect of light, comprising adding an organic material in need of protection from the damaging effect of light to at least one naphthalene-1,8-dicarboxylic monoimide of the formula I

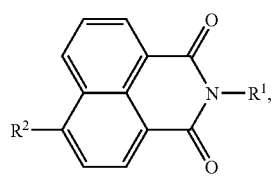

(I)

in which
R$^1$ is hydrogen, alkyl, alkenyl, cycloalkyl, cycloalkenyl, heterocycloalkyl, aryl or heteroaryl and
R$^2$ is cyano, —C(O)NR$^5$R$^{5a}$ or phenyloxy which carries one or more substituents selected from C$_1$-C$_{12}$ alkyl, C$_1$-C$_{12}$ alkoxy, —COOR$^6$, —SO$_3$R$^6$, halogen, hydroxyl, carboxyl, cyano, —CONR$^5$R$^{5a}$, and —NH-COR$^5$;
R$^5$ and R$^{5a}$ each independently of one another are hydrogen, C$_1$-C$_{18}$ alkyl, aryl or heteroaryl, aryl and heteroaryl each being unsubstituted or carrying one or more substituents selected from C$_1$-C$_6$ alkyl, C$_1$-C$_6$ alkoxy, hydroxyl, carboxyl, and cyano; and
R$^6$ is hydrogen or C$_1$-C$_6$ alkyl.

2. The process as claimed in claim 1, wherein
R$^1$ is C$_1$-C$_{30}$ alkyl whose carbon chain may be interrupted by one or more nonadjacent groups selected from —O—, —S—, —NR$^3$—, —CO— and/or —SO$_2$—, and/or which is unsubstituted or substituted one or more times by identical or different radicals selected from cyano, amino, hydroxyl, carboxyl, aryl, heterocycloalkyl, and heteroaryl, with aryl, heterocycloalkyl, and heteroaryl groups being unsubstituted or carrying one or more substituents selected independently of one another from C$_1$-C$_{18}$ alkyl and C$_1$-C$_6$ alkoxy; or
R$^1$ is C$_5$-C$_8$ cycloalkyl which is unsubstituted or carries one or more C$_1$-C$_6$ alkyl groups; or
R$^1$ is 5- to 8-membered heterocycloalkyl which is unsubstituted or carries one or more C$_1$-C$_6$ alkyl groups; or
R$^1$ is aryl or heteroaryl, with aryl or heteroaryl being unsubstituted or carrying one or more radicals selected independently of one another from C$_1$-C$_{18}$ alkyl, C$_1$-C$_6$ alkoxy, cyano, CONR$^4$R$^{4a}$, CO$_2$R$^4$, arylazo, and heteroarylazo, with arylazo and heteroarylazo in turn being unsubstituted or carrying one or more radicals selected independently of one another from C$_1$-C$_{18}$ alkyl, C$_1$-C$_6$ alkoxy, and cyano;
R$^3$ is hydrogen or C$_1$-C$_6$ alkyl; and
R$^4$ and R$^{4a}$ each independently are hydrogen, C$_1$-C$_{18}$ alkyl, aryl or heteroaryl, with aryl and heteroaryl in each case being unsubstituted or carrying one or more substituents selected from C$_1$-C$_6$ alkyl, C$_1$-C$_6$ alkoxy, hydroxyl, carboxyl and cyano.

3. The process as claimed in claim 1, wherein R$^1$ is phenyl which is unsubstituted or carries one, two or three C$_1$-C$_4$ alkyl groups.

4. The process as claimed in claim 1, wherein the organic material for protection is selected from plastics, polymer dispersions, paints, photographic emulsions, photographic layers, paper, human or animal skin, human or animal hair, cosmetic products, pharmaceutical products, cleaning products, and foodstuffs.

5. The process as claimed in claim 4, wherein the organic material for protection is a plastic that comprises at least one polymer selected from polyesters, polycarbonates, polyolefins, polyvinyl acetals, polystyrene, copolymers of styrene or of α-methylstyrene with dienes and/or acrylic derivatives, polyurethanes, polyacrylates, polymethacrylates, and physical blends of the aforementioned polymers.

6. The process as claimed in claim 1, wherein the at least one naphthalene-1,8-dicarboxylic monoimide is used for preparing a layer which absorbs ultraviolet light.

7. The process as claimed in claim 6, wherein the layer is composed of a thermoplastic molding compound, that comprises at least one polymer selected from polyesters, polycarbonates, polyolefins, polyvinyl acetals, polystyrene, copolymers of styrene or of α-methylstyrene with dienes and/or acrylic derivatives, and physical blends of the aforementioned polymers.

8. The process as claimed in claim 1, wherein the organic material contains at least one naphthalene-1,8-dicarboxylic monoimide I in an amount of from 0.01 to 10% by weight, based on the total weight of the material.

9. A composition comprising at least one naphthalene-1,8-dicarboxylic monoimide of the formula I as defined in claim 1, in an amount which provides protection from the damaging effects of light, and at least one organic material, wherein the organic material comprises a polymer selected from polyesters, polycarbonate polymers, polyolefins, polyvinyl acetals, polystyrene, copolymers of styrene or of α-methylstyrene with dienes and/or acrylic derivatives, and physical blends of the aforementioned polymers.

10. The composition as claimed in claim 9, wherein the polyvinyl acetal is a polyvinyl butyral.

11. The composition as claimed in claim 9, wherein the polycarbonate polymer is selected from polycarbonates, polycarbonate copolymers, and physical blends of polycarbonates with acrylonitrile-butadiene-styrene copolymers, acrylonitrile-styrene-acrylate copolymers, polymethyl methacrylates, polybutyl acrylates, polybutyl methacrylates, poly(butylene terephthalates, and polyethylene terephthalates.

12. The composition as claimed in claim 9, wherein the polyester is a polyethylene terephthalate.

13. The composition as claimed in claim 9, wherein the polyolefin is a high-density polyethylene or a polypropylene.

14. The composition as claimed in claim 9, wherein the copolymer of styrene with dienes and/or acrylic derivatives is an acrylonitrile-butadiene-styrene copolymer or a styrene-acrylonitrile copolymer.

15. The composition as claimed in claim 10, comprising
the at least one naphthalene-1,8-dicarboxylic monoimide of the formula I;
at least one polyvinyl butyral;
at least one oligoalkylene glycol alkylcarboxylic diester plasticizer;
at least one aliphatic carboxylic salt for controlling the adhesion;
if desired, at least one further UV absorber selected from benzotriazoles, 2-phenyl-1,3,5-triazines, hydroxybenzophenones, diphenylcyanoacrylates, and mixtures thereof; and
if desired, at least one further component selected from fillers, dyes, pigments, and additional additives.

16. The composition as claimed in claim 11, comprising
the at least one naphthalene-1,8-dicarboxylic monoimide of the formula I;
at least one polycarbonate polymer selected from polycarbonates, polycarbonate copolymers, and physical blends of polycarbonates with acrylonitrile-butadiene-styrene copolymers, acrylonitrile-styrene-acrylate copolymers, polymethyl methacrylates, polybutyl acrylates, polybutyl methacrylates, poly(butylene terephthalate)s, and polyethylene terephthalates;
at least one stabilizer selected from phosphites, phosphonites, and mixtures thereof;
if desired, at least one further UV absorber selected from benzotriazoles, 2-phenyl-1,3,5-triazines, diphenylcyanoacrylates, and mixtures thereof;
if desired, at least one 2,6-dialkylated phenol antioxidant; and
if desired, at least one further component selected from fillers, dyes, pigments, and other additives.

17. The composition as claimed in claim 12, comprising
the at least one naphthalene-1,8-dicarboxylic monoimide of the formula I;
at least one polyethylene terephthalate;
at least one 2,6-dialkylated phenol antioxidant;
at least one costabilizer selected from phosphites, phosphonites, and mixtures thereof; and
if desired, at least one further UV absorber selected from diphenylcyanoacrylates, phenyl-1,3,5-triazines, and benzotriazoles, and mixtures thereof.

18. The composition as claimed in claim 17, wherein the polyethylene terephthalate is an amorphous polyethylene terephthalate and the composition additionally includes at least one acetaldehyde scavenger.

19. The composition as claimed in claim 17, wherein the composition additionally includes at least one further component selected from reheating agents, dyes, pigments, and further additives.

20. The composition as claimed in claim 17, wherein the polyethylene terephthalate is a partially crystalline polyethylene terephthalate and the composition additionally includes at least one nucleating agent.

21. The composition as claimed in claim 13, comprising
the at least one naphthalene-1,8-dicarboxylic monoimide of the formula I;
at least one high-density polyethylene or one polypropylene;
at least one 2,6-dialkylated phenol antioxidant;
at least one costabilizer selected from phosphites, phosphonites, and mixtures thereof;
if desired, at least one further UV absorber selected from diphenylcyanoacrylates, hydroxybenzophenones, phenyl-1,3,5-triazines, and benzotriazoles, and mixtures thereof;
if desired, at least one sterically hindered amine; and
if desired, a further component selected from dyes, pigments, and further additives.

22. The composition as claimed in claim 9, comprising
the at least one naphthalene-1,8-dicarboxylic monoimide of the formula I;
at least one polystyrene;
at least one 2,6-dialkylated phenol antioxidant;
at least one costabilizer selected from phosphites, phosphonites, and mixtures thereof;
if desired, at least one further UV absorber selected from benzotriazoles, diphenylcyanoacrylates, and mixtures thereof;
if desired, at least one sterically hindered amine; and
if desired, at least one further component selected from dyes, pigments, and further additives.

23. The composition as claimed in claim 14, comprising
the at least one naphthalene-1,8-dicarboxylic monoimide of the formula I;
at least one acrylonitrile-butadiene-styrene copolymer or styrene-acrylonitrile copolymer;
at least one 2,6-dialkylated phenol antioxidant;
at least one costabilizer selected from phosphites, phosphonites, and mixtures thereof;
if desired, at least one further UV absorber selected from benzotriazoles, hydroxybenzophenones, diphenylcyanoacrylates, and mixtures thereof;
if desired, at least one sterically hindered amine; and
if desired, a further component selected from dyes, pigments, and further additives.

24. Compounds of the formula I

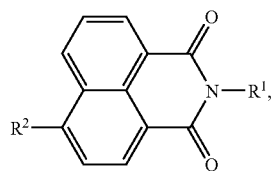

in which
R¹ is hydrogen, alkenyl, cycloalkyl, cycloalkenyl, heterocycloalkyl, aryl or heteroaryl; and
R² is cyano, or phenyloxy which carries one, two, three, four or five $C_1$-$C_{12}$ alkyl groups.

25. Compounds of the formula I as claimed in claim 24, wherein R¹ is $C_5$-$C_8$ cycloalkyl or phenyl, $C_5$-$C_8$ cycloalkyl or phenyl each being unsubstituted or carrying one, two, three, four or five $C_1$-$C_4$ alkyl groups.

26. Compounds of the formula I as claimed in claim 24, wherein R² is cyano.

27. The process as claimed in claim 1, wherein
R¹ is hydrogen, alkenyl, cycloalkyl, cycloalkenyl, heterocycloalkyl, aryl or heteroaryl; and
R² is cyano, or phenyloxy which carries one, two, three, four or five $C_1$-$C_{12}$ alkyl groups.

28. The process as claimed in claim 27, wherein R² is cyano.

* * * * *